US 6,717,035 B2

(12) United States Patent
Petell et al.

(10) Patent No.: US 6,717,035 B2
(45) Date of Patent: Apr. 6, 2004

(54) TRANSGENIC PLANTS EXPRESSING PHOTORHABDUS TOXIN

(75) Inventors: James K. Petell, Grass Valley, CA (US); Donald J. Merlo, Carmel, IN (US); Rod A. Herman, New Ross, IN (US); Jean L. Roberts, Arcadia, IN (US); Lining Guo, Chapel Hill, NC (US); Barry W. Schafer, Cicero, IN (US); Kitisri Sukhapinda, Zionsville, IN (US); Ann Owens Merlo, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 10/435,835

(22) Filed: May 12, 2003

(65) Prior Publication Data

US 2003/0182685 A1 Sep. 25, 2003

Related U.S. Application Data

(62) Division of application No. 09/637,048, filed on Aug. 11, 2000, now Pat. No. 6,590,142.
(60) Provisional application No. 60/148,356, filed on Aug. 11, 1999.

(51) Int. Cl.$^7$ .......................... A01H 5/00; C07H 21/04; C12N 5/10; C12N 15/31; C12N 15/82
(52) U.S. Cl. .................... 800/302; 435/418; 435/419; 536/23.7; 800/320.1; 800/320.2; 800/317.3; 800/288
(58) Field of Search .................... 435/418, 419; 536/23.7; 800/288, 317.3, 302, 320.1, 320.2

(56) References Cited

U.S. PATENT DOCUMENTS

| 6,281,413 B1 | 8/2001 | Kramer et al. ............... 800/302 |
| 6,528,484 B1 | 3/2003 | Ensign et al. ................. 514/12 |

FOREIGN PATENT DOCUMENTS

WO     WO 98/08932    *   3/1998

* cited by examiner

Primary Examiner—David T. Fox
Assistant Examiner—David H Kruse
(74) Attorney, Agent, or Firm—Donald R. Stuart

(57) ABSTRACT

Novel polynucleotide sequences that encode insect toxins TcdA and TcbA have base compositions that differ substantially from the native genes, making them more similar to plant genes. The new sequences are suitable for use for high expression in both monocots and dicots. Transgenic plants with a genome comprising the nucleic acid of SEQ ID NO:4 are insect resistant.

7 Claims, No Drawings

TRANSGENIC PLANTS EXPRESSING PHOTORHABDUS TOXIN

RELATED APPLICATION

This application is a divisional application of application Ser. No. 09/637,048, filed Aug. 11, 2000, now U.S. Pat. No. 6,590,142, which claims benefit of U.S. Provisional Patent Application No. 60/148,356, filed Aug. 11, 1999.

BACKGROUND OF THE INVENTION

As reported in WO98/08932, protein toxins from the genus Photorhabdus have been shown to have oral toxicity against insects. The toxin complex produced by *Photorhabdus luminescens* (W-14), for example, has been shown to contain ten to fourteen proteins, and it is known that these are produced by expression of genes from four distinct genomic regions: tca, tcb, tcc, and tcd. WO98/08932 discloses nucleotide sequences for the native toxin genes.

Of the separate toxins isolated from *Photorhabdus luminescens* (W-14), those designated Toxin A and Toxin B are especially potent against target insect species of interest, for example corn rootworm. Toxin A is comprised of two different subunits. The native gene tcdA (SEQ ID NO:1) encodes protoxin TcdA (see SEQ ID NO:1). As determined by mass spectrometry, TcdA is processed by one or more proteases to provide Toxin A. More specifically, TcdA is an approximately 282.9 kDA protein (2516 aa) that is processed to provide TcdAii, an approximately 208.2 kDA (1849 aa) protein encoded by nucleotides 265–5811 of SEQ ID NO:1, and TcdAiii, an approximately 63.5 kDA (579 aa) protein encoded by nucleotides 5812–7551 of SEQ ID NO:1.

Toxin B is similarly comprised of two different subunits. The native gene tcbA (SEQ ID NO:2) encodes protoxin TcbA (see SEQ ID NO:2). As determined by mass spectrometry, TcbA is processed by one or more proteases to provide Toxin B. More specifically, TcbA is an approximately 280.6 kDA (2504 aa) protein that is processed to provide TcbAii, an approximately 207.7 kDA (1844 aa) protein encoded by nucleotides 262–5793 of SEQ ID NO:2 and TcbAiii, an approximately 62.9 kDA (573 aa) protein encoded by nucleotides 5794–7512 of SEQ ID NO:2.

The native tcdA and tcbA genes are not well suited for high level expression in plants. They encode multiple destabilization sequences, mRNA splice sites, polyA addition sites and other possibly detrimental sequence motifs. In addition, the codon compositions are not like those of plant genes. WO98/08932 gives general guidance on how the toxin genes could be reengineered to more efficiently expressed in the cytoplasm of plants, and describes how plants can be transformed to incorporate the Photorhabdus toxin genes into their genomes.

SUMMARY OF THE INVENTION

In a preferred embodiment, the invention provides novel polynucleotide sequences that encode TcdA and TcbA. The novel sequences have base compositions that differ substantially from the native genes, making them more similar to plant genes. The new sequences are suitable for use for high expression in both monocots and dicots, and this feature is designated by referring to the sequences as the "hemicot" criteria, which is set forth in detail hereinafter. Other important features of the sequences are that potentially deleterious sequences have been eliminated, and unique restriction sites have been built in to enable adding or changing expression elements, organellar targeting signals, engineered protease sites and the like, if desired.

In a particularly preferred embodiment, the invention provides polynucleotide sequences that satisfy hemicot criteria and that comprise a sequence encoding an endoplasmic reticulum signal or similar targeting sequence for a cellular organelle in combination with a sequence encoding TcdA or TdbA.

More broadly, the invention provides engineered nucleic acids encoding functional Photorhabdus toxins wherein the sequences satisfy hemicot criteria.

The invention also provides transgenic plants with genomes comprising a novel sequence of the invention that imparts functional activity against insects.

BRIEF DESCRIPTION OF SEQUENCES

SEQ ID NO:1 is the native tcdA DNA sequence together with the corresponding encoded amino acid sequence for TcdA.

SEQ ID NO:2 is the native tcbA DNA sequence together with the corresponding encoded amino acid sequence for TcbA.

SEQ ID NO:3 is an artificial sequence encoding TcdA that is suitable for expression in monocot and dicot plants.

SEQ ID NO:4 is an artificial sequence encoding TcbA that is suitable for expression in monocot and dicot plants.

SEQ ID NO:5 is an artificial hemicot sequence that encodes the 21 amino acid ER signal peptide of 15 kDa zein from Black Mexican Sweet maize.

SEQ ID NO:6 is an artificial hemicot sequence that encodes for the full-length native TcdA protein (amino acids 22–2537) fused to the modified 15 kDa zein endoplasmic reticulum signal peptide (amino acids 1–21).

DETAILED DESCRIPTION

The native Photorhabdus toxins are protein complexes that are produced and secreted by growing bacteria cells of the genus Photorhabdus. Of particular interest are the proteins produced by the species *Photorhabdus luminescens*. The protein complexes have a molecular size of approximately 1,000 kDa and can be separated by SDS-PAGE gel analysis into numerous component proteins. The toxins contain no hemolysin, lipase, type C phospholipase, or nuclease activities. The toxins exhibit significant toxicity upon ingestion by a number of insects.

A unique feature of Photorhabdus is its bioluminescence. Photorhabdus may be isolated from a variety of sources. One such source is nematodes, more particularly nematodes of the genus Heterorhabditis. Another such source is from human clinical samples from wounds, see Farmer et al. 1989 J. Clin. Microbiol. 27 pp. 1594–1600. These saprohytic strains are deposited in the American Type Culture Collection (Rockville, Md.) ATCC #s 43948, 43949, 43950, 43951, and 43952, and are incorporated herein by reference. It is possible that other sources could harbor Photorhabdus bacteria that produce insecticidal toxins. Such sources in the environment could be either terrestrial or aquatic based.

The genus Photorhabdus is taxonomically defined as a member of the Family Enterobacteriaceae, although it has certain traits a typical of this family. For example, strains of this genus are nitrate reduction negative, yellow and red pigment producing and bioluminescent. This latter trait is otherwise unknown within the Enterobacteriaceae. Photorhabdus has only recently been described as a genus separate from the Xenorhabdus (Boemare et al., 1993 Int. J. Syst. Bacteriol. 43, 249–255). This differentiation is based on DNA—DNA hybridization studies, phenotypic differences (e.g., presence (Photorhabdus) or absence (Xenorhabdus) of catalase and bioluminescence) and the Family of the nematode host (Xenorhabdus; Steinernematidae, Photorhabdus; Heterorhabditidae). Comparative, cellular fatty-acid analyses (Janse et al. 1990, Lett. Appl. Microbiol 10, 131–135; Suzuki et al. 1990, J. Gen. Appl. Microbiol., 36, 393–401) support the separation of Photorhabdus from Xenorhabdus.

Currently, the bacterial genus Photorhabdus is comprised of a single defined species, *Photorhabdus luminescens* (ATCC Type strain #29999, Poinar et al., 1977, Nematologica 23, 97–102). A variety of related strains have been described in the literature (e.g., Akhurst et al. 1988 J. Gen. Microbiol., 134, 1835–1845; Boemare et al. 1993 Int. J. Syst. Bacteriol. 43 pp. 249–255; Putz et al. 1990, Appl. Environ. Microbiol., 56, 181–186).

The following toxin producing Photorhabdus strains have been deposited:

| strain | accession number | date of deposit |
| --- | --- | --- |
| W-14 | ATCC 55397 | Mar. 5, 1993 |
| WX1 | NRRL B-21710 | Apr. 29, 1997 |
| WX2 | NRRL B-21711 | Apr. 29, 1997 |
| WX3 | NRRL B-21712 | Apr. 29, 1997 |
| WX4 | NRRL B-21713 | Apr. 29, 1997 |
| WX5 | NRRL B-21714 | Apr. 29, 1997 |
| WX6 | NRRL B-21715 | Apr. 29, 1997 |
| WX7 | NRRL B-21716 | Apr. 29, 1997 |
| WX8 | NRRL B-21717 | Apr. 29, 1997 |
| WX9 | NRRL B-21718 | Apr. 29, 1997 |
| WX10 | NRRL B-21719 | Apr. 29, 1997 |
| WX11 | NRRL B-21720 | Apr. 29, 1997 |
| WX12 | NRRL B-21721 | Apr. 29, 1997 |
| WX14 | NRRL B-21722 | Apr. 29, 1997 |
| WX15 | NRRL B-21723 | Apr. 29, 1997 |
| H9 | NRRL B-21727 | Apr. 29, 1997 |
| Hb | NRRL B-21726 | Apr. 29, 1997 |
| Hm | NRRL B-21725 | Apr. 29, 1997 |
| HP88 | NRRL B-21724 | Apr. 29, 1997 |
| NC-1 | NRRL B-21728 | Apr. 29, 1997 |
| W30 | NRRL B-21729 | Apr. 29, 1997 |
| WIR | NRRL B-21730 | Apr. 29, 1997 |
| B2 | NRRL B-21731 | Apr. 29, 1997 |
| ATCC 43948 | ATCC 55878 | Nov. 5, 1996 |
| ATCC 43949 | ATCC 55879 | Nov. 5, 1996 |
| ATCC 43950 | ATCC 55880 | Nov. 5, 1996 |
| ATCC 53951 | ATCC 55881 | Nov. 5, 1996 |
| ATCC 43952 | ATCC 55882 | Nov. 5, 1996 |
| DEPI | NRRL B-21707 | Apr. 29, 1997 |
| DEP2 | NRRL B-21708 | Apr. 29, 1997 |
| DEP3 | NRRL B-21709 | Apr. 29, 1997 |
| *P. zealandrica* | NRRL B-21683 | Apr. 29, 1997 |
| *P. hepialus* | NRRL B-21684 | Apr. 29, 1997 |
| HB-Arg | NRRL B-21685 | Apr. 29, 1997 |
| HB Oswego | NRRL B-21686 | Apr. 29, 1997 |
| Hb Lewiston | NRRL B-21687 | Apr. 29, 1997 |
| K-122 | NRRL B-21688 | Apr. 29, 1997 |
| HMGD | NRRL B-21689 | Apr. 29, 1997 |
| Indicus | NRRL B-21690 | Apr. 29, 1997 |
| GD | NRRL B-21691 | Apr. 29, 1997 |
| PWH-5 | NRRL B-21692 | Apr. 29, 1997 |
| Megidis | NRRL B-21693 | Apr. 29, 1997 |
| HF-85 | NRRL B-21694 | Apr. 29, 1997 |
| A. Cows | NRRL B-21695 | Apr. 29, 1997 |
| MP1 | NRRL B-21696 | Apr. 29, 1997 |
| MP2 | NRRL B-21697 | Apr. 29, 1997 |
| MP3 | NRRL B-21698 | Apr. 29, 1997 |
| MP4 | NRRL B-21699 | Apr. 29, 1997 |
| MP5 | NRRL B-21700 | Apr. 29, 1997 |
| GL98 | NRRL B-21701 | Apr. 29, 1997 |
| Gl101 | NRRL B-21702 | Apr. 29, 1997 |
| GL138 | NRRL B-21703 | Apr. 29, 1997 |
| GL155 | NRRL B-21704 | Apr. 29, 1997 |
| GL217 | NRRL B-21705 | Apr. 29, 1997 |
| GL257 | NRRL B-21706 | Apr. 29, 1997 |

All strains were deposited in accordance with the terms of the Budapest Treaty. Strains having accession numbers prefaced by "ATTC" were deposited on the indicated date in the American Type Culture Collection, 12301 Parklawn Drive, Rockville, Md. 20852 USA. Strains prefaced by "NRRL" were deposited on the indicated date in the Agricultural Research Service Patent Culture Collection (NRRL), National Center for Agricultural Utilization Research, ARS-USDA, 1815 North University St., Peoria Ill. 61604 USA.

The present invention provides hemicot nucleic acid sequences encoding toxins from any Photorhabdus species or strain that produces a toxin having functional activity. Hemicot nucleic acid sequences encoding proteins homologous to such toxins are also encompassed by the invention.

Several terms that are used herein have a particular meaning and are defined as follows:

By "functional activity" it is meant herein that the protein toxins) function as insect control agents in that the proteins are orally active, or have a toxic effect, or are able to disrupt or deter feeding, which may or may not cause death of the insect. When an insect comes into contact with an effective amount of toxin delivered via transgenic plant expression, formulated protein compositions), sprayable protein compositions), a bait matrix or other delivery system, the results are typically death of the insect, or the insects do not feed upon the source which makes the toxins available to the insects.

By "homolog" it is meant an amino acid sequence that is identified as possessing homology to a reference Photorhabdus toxin polypeptide amino acid sequence.

By "homology" it is meant an amino acid sequence that has a similarity index of at least 33% and/or an identity index of at least 26% to a reference Photorhabdus toxin polypeptide amino acid sequence, as scored by the GAP algorithm using the B10sum 62 protein scoring matrix Wisconsin Package Version 9.0, Genetics Computer Group GCG), Madison, Wis.).

By "identity" is meant an amino acid sequence that contains an identical residue at a given position, following alignment with a reference Photrhabdus toxin polypeptide amino acid sequence by the GAP algorithm.

By the use of the term "Photorhabdus toxin" it is meant any protein produced by a Photorhabdus microorganism strain which has functional activity against insects, where the Photorhabdus toxin could be formulated as a sprayable composition, expressed by a transgenic plant, formulated as a bait matrix, delivered via baculovirus, or delivered by any other applicable host or delivery system.

By the use of the term "toxic" or "toxicity" as used herein it is meant that the toxins produced by Photorhabdus have "functional activity" as defined herein.

By "substantial sequence homology" is meant either: a DNA fragment having a nucleotide sequence sufficiently similar to another DNA fragment to produce a protein having similar biochemical properties; or a polypeptide having an amino acid sequence sufficiently similar to another polypeptide to exhibit similar biochemical properties.

As with other bacterial toxins, the rate of mutation of the bacteria in a population causes many related toxins slightly different in sequence to exist. Toxins of interest here are those which produce protein complexes toxic to a variety of insects upon exposure, as described herein. Preferably, the toxins are active against Lepidoptera, Coleoptera, Homopotera, Diptera, Hymenoptera, Dictyoptera and Acarina. The inventions herein are intended to capture the protein toxins homologous to protein toxins produced by the strains herein and any derivative strains thereof, as well as any protein toxins produced by Photorhabdus. These homologous proteins may differ in sequence, but do not differ in function from those toxins described herein. Homologous toxins are meant to include protein complexes of between 300 kDa to 2,000 kDa and are comprised of at least two 2) subunits, where a subunit is a peptide which may or may not be the same as the other subunit. Various protein subunits have been identified and are taught in the Examples herein. Typically, the protein subunits are between about 18 kDa to about 230 kDa; between about 160 kDa to about 230 kDa; 100 kDa to 160 kDa; about 80 kDa to about 100 kDa; and about 50 kDa to about 80 kDa.

As discussed above, some Photorhabdus strains can be isolated from nematodes. Some nematodes, elongated cylindrical parasitic worms of the phylum Nematoda, have evolved an ability to exploit insect larvae as a favored growth environment. The insect larvae provide a source of food for growing nematodes and an environment in which to reproduce. One dramatic effect that follows invasion of larvae by certain nematodes is larval death. Larval death results from the presence of, in certain nematodes, bacteria that produce an insecticidal toxin which arrests larval growth and inhibits feeding activity.

Interestingly, it appears that each genus of insect parasitic nematode hosts a particular species of bacterium, uniquely adapted for symbiotic growth with that nematode. In the interim since this research was initiated, the name of the bacterial genus Xenorhabdus was reclassified into the Xenorhabdus and the Photorhabdus. Bacteria of the genus Photorhabdus are characterized as being symbionts of Heterorhabditus nematodes while Xenorhabdus species are symbionts of the Steinernema species. This change in nomenclature is reflected in this specification, but in no way should a change in nomenclature alter the scope of the inventions described herein.

The peptides and genes that are disclosed herein are named according to the guidelines recently published in the Journal of Bacteriology "Instructions to Authors" p. i–xii January 1996), which is incorporated herein by reference.

Transformation methods useful in carrying out the invention are well known, and are described, for example, in WO98/08932.

Hemicot tcdA and tcbA

SEQ ID NO: 3 is the nucleotide sequence for an engineered tcdA gene in accordance with the invention. SEQ ID NO: 4 is the nucleotide sequence for an engineered tcbA gene in accordance with the invention.

The following Tables 1 and 2 identify significant features of the engineered tcdA and tcbA genes.

TABLE 1

| tcdA | |
|---|---|
| Feature | nucleotides of SEQ ID NO:3 |
| NcoI | 1–6 |
| HindIII | 48–53 |

TABLE 1-continued

| tcdA | |
|---|---|
| Feature | nucleotides of SEQ ID NO:3 |
| KpnI | 246–254 |
| sequence encoding TcbAii | 267–5798 |
| NheI | 333–338 |
| BglII | 1215–1220 |
| ClaI | 2604–2609 |
| PstI | 4015–4020 |
| AgeI | 5088–5093 |
| MunI | 5598–5603 |
| XbaI | 5778–5783 |
| sequence encoding TcbAiii | 5799–7517 |
| AflII | 5853–5858 |
| SphI | 6439–6444 |
| SfuI | 7392–7397 |
| SacI | 7519–7524 |
| XhoI | 7522–7527 |
| StuI | 7528–7533 |
| NotI | 7533–7538 |

TABLE 2

| tcbA | |
|---|---|
| Feature | nucleotides of SEQ ID NO:5 |
| NcoI | 1–6 |
| HindIII | 48–53 |
| KpnI | 246–251 |
| sequence encoding TcbAii | 267–5798 |
| NheI | 333–338 |
| BglII | 1215–1220 |
| ClaI | 2604–2609 |
| PstI | 4015–4020 |
| AgeI | 5088–5093 |
| MunI | 5598–5603 |
| XbaI | 5778–5783 |
| sequence encoding TcbAiii | 5799–7517 |
| AflII | 5853–5858 |
| SphI | 6439–6444 |
| SfuI | 7392–7397 |
| SacI | 7519–7524 |
| SfuI | 7392–7397 |
| SacI | 7519–7524 |
| XhoI | 7522–7527 |
| StuI | 7528–7533 |
| NotI | 7535–7540 |

It should be noted that the proteins encoded by the plant-optimized tcdA (SEQ ID NO:3) and tcbA (SEQ ID NO:5) differ from the native proteins by the addition of an Ala residue at position #2. This modification was made to accommodate the NcoI site which spans the ATG start codon.

The following Table 3 compares the codon composition of the engineered tcdA gene of SEQ ID NO:3 and engineered tcbA gene of SEQ ID NO:5 with the codon compositions of the native genes, the typical dicot genes, and maize genes.

TABLE 3

| amino acid | codon | % in SEQ ID NO:3 | % in tcdA | % in SEQ ID NO:5 | % in tcbA | % in dicot | % in maize |
|---|---|---|---|---|---|---|---|
| Ala | GCT | 62 | 21 | 69 | 41 | 42 | 24 |
| | GCC | 26 | 32 | 27 | 17 | 27 | 34 |
| | GCA | 11 | 25 | 4 | 22 | 25 | 18 |
| | GCG | 0 | 21 | 0 | 21 | 6 | 24 |
| Arg | AGG | 48 | 0 | 60 | 2 | 25 | 26 |
| | CGC | 22 | 36 | 18 | 16 | 11 | 24 |
| | AGA | 20 | 11 | 15 | 6 | 30 | 15 |
| | CGT | 11 | 39 | 7 | 57 | 21 | 11 |
| | CGG | 0 | 7 | 0 | 13 | 4 | 15 |
| | CGA | 0 | 8 | 0 | 6 | 8 | 9 |
| Asn | AAC | 100 | 32 | 100 | 33 | 55 | 68 |
| | AAT | 0 | 68 | 0 | 67 | 45 | 32 |
| Asp | GAC | 67 | 22 | 70 | 25 | 42 | 63 |
| | GAT | 33 | 78 | 30 | 75 | 58 | 37 |
| Cys | TGC | 100 | 30 | 100 | 19 | 56 | 68 |
| | TGT | 0 | 70 | 0 | 81 | 44 | 32 |
| End | TGA | 100 | 0 | 100 | 0 | 33 | 59 |
| | TAG | 0 | 0 | 0 | 0 | 19 | 21 |
| | TAA | 0 | 100 | 0 | 100 | 48 | 20 |
| Gln | CAA | 65 | 61 | 74 | 53 | 59 | 38 |
| | CAG | 35 | 39 | 26 | 47 | 41 | 62 |
| Glu | GAG | 100 | 24 | 98 | 36 | 51 | 71 |
| | GAA | 0 | 76 | 2 | 64 | 49 | 29 |
| Gly | GGT | 67 | 37 | 64 | 44 | 33 | 20 |
| | GGC | 32 | 36 | 36 | 22 | 16 | 42 |
| | GGA | 1 | 20 | 0 | 19 | 38 | 19 |
| | GGG | 0 | 8 | 0 | 16 | 12 | 20 |
| His | CAC | 62 | 40 | 72 | 31 | 46 | 62 |
| | CAT | 38 | 60 | 28 | 69 | 54 | 38 |
| Ile | ATC | 73 | 34 | 65 | 24 | 37 | 58 |
| | ATT | 27 | 51 | 35 | 59 | 45 | 28 |
| | ATA | 0 | 15 | 0 | 17 | 18 | 14 |
| Leu | CTC | 54 | 11 | 59 | 7 | 28 | 26 |
| | TTG | 29 | 17 | 25 | 32 | 26 | 15 |
| | CTT | 16 | 9 | 15 | 7 | 19 | 17 |
| | TTA | 0 | 18 | 0 | 19 | 10 | 5 |
| | CTG | 0 | 32 | 0 | 29 | 9 | 29 |
| | CTA | 0 | 13 | 0 | 7 | 8 | 8 |
| Lys | AAG | 99 | 79 | 99 | 75 | 61 | 78 |
| | AAA | 1 | 21 | 1 | 25 | 39 | 22 |
| Met | ATG | 100 | 100 | 100 | 100 | 100 | 100 |
| Phe | TTC | 100 | 42 | 100 | 41 | 55 | 71 |
| | TTT | 0 | 58 | 0 | 59 | 45 | 29 |
| Pro | CCA | 74 | 30 | 91 | 26 | 42 | 26 |
| | CCT | 22 | 28 | 7 | 20 | 32 | 22 |
| | CCC | 4 | 14 | 3 | 7 | 17 | 24 |
| | CCG | 0 | 27 | 0 | 47 | 9 | 28 |
| Ser | TCC | 47 | 19 | 55 | 11 | 18 | 23 |
| | TCT | 35 | 15 | 30 | 15 | 25 | 15 |
| | AGC | 18 | 22 | 15 | 18 | 18 | 23 |
| | AGT | 0 | 20 | 0 | 31 | 14 | 9 |
| | TCG | 0 | 7 | 0 | 8 | 6 | 14 |
| | TCA | 0 | 17 | 0 | 17 | 19 | 16 |
| Thr | ACC | 60 | 41 | 64 | 31 | 30 | 37 |
| | ACT | 28 | 25 | 32 | 34 | 35 | 20 |
| | ACA | 12 | 21 | 4 | 18 | 27 | 21 |
| | ACG | 0 | 13 | 0 | 18 | 8 | 22 |
| Trp | TGG | 100 | 100 | 100 | 100 | 100 | 100 |
| Tyr | TAC | 100 | 24 | 100 | 19 | 57 | 73 |
| | TAT | 0 | 76 | 0 | 81 | 43 | 27 |
| Val | GTC | 69 | 27 | 73 | 11 | 20 | 31 |
| | GTG | 21 | 17 | 22 | 27 | 29 | 39 |
| | GTT | 10 | 34 | 3 | 48 | 39 | 21 |
| | GTA | 0 | 22 | 2 | 14 | 12 | 8 |

EXAMPLE 1

Design Of Plant Codon-Biased Genes Encoding W-14 Peptides TcbA and TcdA

A. Gene Design

The coding strands of the native DNA sequences of the Photorhabdus W-14 genes encoding peptides TcbA and TcdA were scanned for the presence of deleterious sequences such as the Shaw/Kamen RNA destabilizing motif ATTTA, intron splice recognition sites, and poly A addition motifs. This was done using the Macvector Sequence Analysis Software (Oxford Molecular Biology Group, Symantec Corp.), using a custom Nucleic Acid Subsequence File. The native sequence was also searched for runs of 4 or more of the same base.

Motif searching of the native W-14 tcbA and tcdA genes revealed the presence of many potentially deleterious sequences in the protein coding strands, as summarized in Table 4. Not shown, but also present, were many runs of four or more single residues (e.g. the native tcbA gene has 81 runs of four A's).

TABLE 4

| Native Gene | ATTTA | 5' Splice | 3' Splice | Poly A Addition* | RNAP II term. |
|---|---|---|---|---|---|
| tcbA | 18 | 7 | 17 | 46 | 0 |
| tcdA | 18 | 7 | 13 | 77 | 1 |

*Totals of 16 different motifs.

Analyses of eukaryotic genes and plant genes in particular have shown that CG & TA doublets are underrepresented, while the genes are enriched in CT & TG doublets. The sequences of the hemicot biased genes have accordingly been adjusted to encompass these base compositions and to have G+C compositions of about 53%, similar to-many plant genes. When compared to the native W-14 tcbA and tcdA genes, the plant-biased genes have a much more uniform G+C distribution.

Nucleotide changes to remove potentially deleterious sequences were chosen to simultaneously adjust the codon composition of the coding region to more closely reflect that of plant genes. A framework for these changes was provided by the codon bias tables prepared for maize and dicot genes shown in Table 3.

Comparison of codon compositions of the native W-14 genes to maize and dicot genes revealed that the W-14 genes contain a very different preference set of the degenerate codons for the 18 amino acids for which there is a choice (Table 3). For each of 8 amino acids (Phe, Tyr, Cys, Arg, Asn, Lys, Glu, and Gly) in both W-14 genes, the most abundant codon is different from the preferred codons found in either maize or dicot genes. One might expect that translational difficulties would be encountered in efforts to produce in plants proteins (such as TcbA and TcdA) having high relative amounts of these amino acids from mRNAs having large numbers of nonpreferred codons. There is a marked difference in distribution of the codon compositions specifying the other 10 amino acids. For His, Gln, Ile, Val, and Asp, the dicot-preferred codons are found as the most abundant ones in both W-14 genes. For Leu, Thr, Ser, and Ala, the maize preferred codons are the most abundant codon choices found in the tcdA gene. In contrast, the tcbA gene contains only the CCG (Pro) maize-preferred codon as the highest abundance choice.

In making the codon choices, doublet contents were considered, so that adjacent codons preferably did not form CG or TA doublets (which are underrepresented in eukaryotic genes; 1, 4), while CT or TG doublets (which are enriched in eukaryotic genes ibid.) were created when possible.

Choices were also made to utilize a diversity of codons for Met, Trp, Asn, Asp, Cys, Glu, His, Ile, Lys, Phe, Thr, and Tyr.

The sequences were also designed to encode unique 6-bp recognition sites for restriction enzymes, spaced about every 1200 bp. Finally, an additional codon (GCT; Ala) was inserted at the second position to encode an Nco I recognition site encompassing the ATG (Met) start codon. Additional recognition sites were included after the stop codon to facilitate subsequent cloning steps into expression vectors. These features are set forth above in Tables 1 and 2.

The new tcdA and tcbA genes of SEQ ID NO:3 and SEQ ID NO:4 share 73.5%, and 72.6% identity, respectively, to their native W-14 counterparts (Wisconsin Genetics Computer Group, GAP algorithm).

B. Gene Synthesis

The complete synthesis of the plant codon-biased tcbA and tcdA genes was performed under contract by Operon Technologies, Inc. (OPTI, Alameda, Calif.). Basically, chemically synthesized oligonucleotides of appropriate sequence were assembled into DNA pieces about 500 bases long. These were joined together end-to-end (presumably by means of appropriately placed restriction enzyme sites) into four larger pieces of roughly 2 kilobase pairs (kbp) each; therefore each comprised about ¼ of the entire coding region of the particular gene. DNA sequence of the pieces was confirmed at this step. If mistakes in sequence were present, the appropriate oligonucleotides were re-synthesized, and the assembly process was repeated. Once gene fractional parts were sequence verified, they were assembled in pairs to make the gene halves, and again sequence verified. Finally, the two halves were joined, and the sequences of the junctions between the halves was verified. Therefore, each part of the new gene was sequence verified at least twice.

It should be noted that attempts to express the native tcbA or tcdA genes in standard *Escherichia coli* cloning strains suggests that production of these proteins is lethal. Lethality problems may be encountered if standard cloning vectors having leaky expression from inherent lacZ promoters are used to assemble these genes.

C. Addition of Endoplasmic Reticulum Targeting Peptide to TcdA Coding Region

It is known to those in the field of plant gene expression that proteins are specifically directed into the endoplasmic reticulum (ER) by means of a short signal peptide which is removed during or after the transport process through the ER membrane. The mature (processed) protein is incorporated into the ER endomembrane or is released into the ER lumen where the transported protein may be uniquely folded (aided by chaperonins), modified by glycosylation, accumulated in the vacuole, or additionally translocated (by secretion). These processes are reviewed by Gomord and Faye [V. Gomord and L. Faye, (1996) *Signals and mechanisms involved in intracellular transport of secreted proteins in plants*. Plant Physiol. Biochem. 34:165–181] and by Bar-Peled et al. [M. Bar-Peled, D.C. Bassham, and N. V. Raikhel, (1996) *Transport of proteins in eukaryotic cells: more questions ahead*. Plant Molec. Biology 32:223–249]. It is also known that the subcellular recognition mechanisms for an ER signal peptide are evolutionarily somewhat conserved, since the ER signal for a protein normally produced in monocot (maize) cells is recognized and processed normally by dicot (tobacco) cells. This is exemplified by the maize 15 kDa zein ER signal peptide [L. M. Hoffman, D. D. Donaldson, R. Bookland, K. Rashka, and E. M. Herman, (1987) *Synthesis and protein body deposition of maize 15-kd zein in transgenic tobacco seeds*. EMBO J. 6:3213–3221, and U.S. Pat. No. 5,589,616]. Further, it is known that the ER signal peptide derived from one protein can direct the translocation of a different protein if it is appropriately attached to the second protein by genetic engineering methods [D.C. Hunt and M. J. Chrispeels, (1991) *The signal peptide of a vacuolar protein is necessary and sufficient for the efficient secretion of a cytosolic protein*. Plant Physiol. 96:18–25, and Denecke, J., J. Botterman, and R. Deblaere (1990) *Protein secretion in plants can occur via a default pathway*. Plant Cell 2:51–59]. Therefore, one may expose a protein in vivo to different biochemical environments by directing its accumulation in the cytosol (by not providing a signal peptide sequence), or in the ER/vacuole (by provision of an appropriate signal peptide.)

The ER signal peptide of maize 15 kDa zein proteins is known to comprise the first 20 amino acids encoded by the zein coding region. Two examples of such signal peptides the ER signal peptide of 15 kDa zein from A5707 maize, NCBI Accession # M72708, and the ER signal peptide of 15 kDa zein from Black Mexican Sweet maize, NCBI Accession #M13507. There is only a single amino acid difference (Ser vs Cys at residue 17) between these signal peptides.

SEQ ID NO:5 is a modified sequence coding the ER signal peptide of 15 kDa zein from Black Mexican Sweet maize. The modifications embodied in this sequence were made to accommodate the different monocot/dicot codon usages and other sequence motif considerations discussed above in the design of the plant-optimized tcdA coding region. The sequence includes an additional Ala residue at position #2 to accommodate the NcoI site which spans the ATG start codon.

SEQ ID NO:6 gives a sequence coding for the full-length native TcdA protein (amino acids 22–2537) fused to the modified 15 kDa zein endoplasmic reticulum signal peptide (amino acids 1–21).

EXAMPLE 2

Transformation of Tobacco with Agrobacterium Carrying Plasmid pDAB2041 Encoding Photorhabdus Toxins A. Plasmid pDAB2041

Preparation of tobacco transformation vectors was accomplished in three steps. First, a modified plant-optimized tcdA coding region was ligated into a tobacco plant expression cassette plasmid. In this step, the coding region was placed under the transcriptional control of a promoter functional in tobacco plant cells. RNA transcription termination and polyadenylation were mediated by a downstream copy of the terminator region from the *Agrobacterium nopaline* synthase gene. Two plasmids designed to function in this role are pDAB1507 and pDAB2006. In the second step, the complete gene comprised of the promoter, coding region, and terminator region was ligated between the T-DNA borders of an Agrobacterium binary vector, pDAB1542. Also positioned between the T-DNA borders was a plant selectable marker gene to allow selection of transformed tobacco plant cells. In the third step, the engineered binary vector plasmid was conjugated from its *E. coli* host strain into a disabled *Agrobacterium tumefaciens* strain capable of transforming tobacco plant cells that regenerate into fertile transgenic plants.

It is a feature of plasmid pDAB1507 that any coding region having an NcoI site at its 5' end and a SacI site 3' to the coding region, when cloned into the unique NcoI and SacI sites of pDAB1507, is placed under the transcriptional control of an enhanced version of the CaMV 35S promoter. It is also a feature of pDAB1507 that the 5' untranslated leader (UTR) sequence preceding the NcoI site comprises a modified version of the 5' UTR of the MSV coat protein gene, into which has been cloned an internally deleted version of the maize Adh1S intron 1. Additionally it is a feature of pDAB1507 that transcription termination and polyadenylation of the mRNA containing the introduced coding region are mediated by termination/Poly A addition sequences derived from the nopaline synthase (Nos) gene. Finally, it is a feature of pDAB1507 that the entire assembly of promoter/coding region/3'UTR can be obtained as a single DNA fragment by cleavage at the flanking NotI sites.

It is a feature of plasmid pDAB2006 that any coding region having an NcoI site at its 5' end and a SacI site 3' to the coding region, when cloned into the unique NcoI and SacI sites of pDAB2006, is placed under the transcriptional control of the CaMV 35S promoter. It is also a feature of pDAB2006 that the 5' untranslated leader (UTR) sequence preceding the NcoI site comprises a polylinker. Additionally it is a feature of pDAB2006 that transcription termination and polyadenylation of the mRNA containing the introduced coding region are mediated by termination/Poly A addition sequences derived from the nopaline synthase (Nos) gene. Finally, it is a feature of pDAB2006 that the entire assembly of promoter/coding region/3'UTR can be obtained as a single DNA fragment by cleavage at the flanking NotI sites.

It is a feature of pDAB1542 that any DNA fragment flanked by NotI sites can be cloned into the unique NotI site of pDAB1542, thus placing the introduced fragment between the T-DNA borders, and adjacent to the neomycin phosphotransferase II (kanamycin resistance) gene.

To prepare a plant-expressible gene to produce the non-targeted TcdA protein in tobacco plant cells, DNA of a plasmid (pA0H_4-OPTI) containing the plant-optimized tcdA coding region, (SEQ ID No:3) was cleaved with restriction enzymes NcoI and SacI, and the large 7550 bp fragment was ligated to similarly-cut DNA of plasmid pDAB1507 to produce plasmid pDAB2040. DNA of pDAB2040 was then digested with NotI, and the 8884 bp fragment was ligated to NotI digested DNA of pDAB1542 to produce plasmid pDAB2041. This plasmid was then conjugated by triparental mating [Firoozabady, E., D. L. DeBoer, D. J. Merlo, E. L. Halk, L. N. Amerson, K. E. Rashka, and E. E. Murray (1987) Transformation of cotton (*Gossypium hirsutum* L.) by *Agrobacterium tumefaciens* and regeneration of transgenic plants. Plant Molec. Biol. 10:105–116] from the host *Escherichia coli* strain (XL1-Blue, Stratagene, La Jolla, Calif.), into the nontumorigenic *Agrobacterium tumefaciens* strain EHA101S, which is a spontaneous streptomycin-resistant mutant of strain EHA101 (Hood, E. E., G. L. Helmer, R. T. Fraley, and M. D. Chilton (1986) The hypervirulence of *Agrobacterium tumefaciens* A281 is encoded in a region of pTiBo542 outside of T-DNA. J. Bacteriol. 168:1291–1301). Strain EHA101S(pDAB2041) was then used to produce transgenic tobacco plants that expressed the TcdA protein.

B. Plasmid pRK2013

To prepare a plant-expressible gene to produce the endoplasmic reticulum-targeted TcdA protein in tobacco plant cells, DNA of a plasmid (pA0H_4-ER) containing the plant-optimized, ER-targeted tcdA coding region, (SEQ ID No:6) was cleaved with restriction enzymes NcoI and SacI, and the large 7610 bp fragment was ligated to similarly-cut DNA of plasmid pDAB2006 to produce plasmid pDAB1833. DNA of pDAB1833 was then digested with NotI, and the 8822 bp fragment was ligated to NotI digested DNA of pDAB1542 to produce plasmid pDAB2052. This plasmid was then conjugated by triparental mating from the host *Escherichia coli* strain (XL1-Blue), into the nontumorigenic *Agrobacterium tumefaciens* strain EHA101S. Strain EHA101S(pDAB2052) was then used to produce transgenic tobacco plants that expressed the TcdA protein containing an amino terminus endoplasmic reticulum targeting peptide.

C. Transfer of Plasmid pDAB2041 Into Agrobacterium Strain EHA101S

Cultures of *E. coli* carrying the engineered Ti plasmid pDAB2041 (plasmid containing the rebuilt Toxin A gene, tcdA), *E. coli* carrying the plasmid pRK2013, and Agrobacterium strain EHA101S were grown overnight, then mixed 1:1:1 on plain LB medium solidified with agar and cultured in the dark at 28° C. Two days later, the lawn of bacteria was scraped up with a loop, suspended in plain LB medium, vortexed, and then diluted $1:10^4$, $1:10^5$, and $1:10^6$ fold in plain LB liquid medium. Aliquots of these dilutions were spread on selective plates containing medium YEP plus erythromycin (100 mg/L) and streptomycin (250 mg/L) and grown at 28° C. Two days later, single colonies were picked and streaked onto the same medium, then spread to give single colonies. Single colonies were picked again and streaked, then spread for single colonies. Single colonies were picked a third time, grown as streaks, then subjected to a quality analysis involving growth on lactose medium and chromogenic assay with Benedict's reagent. Of ten strains developed in this way, the fastest coloring colony was chosen for further work.

D. Transformation of Tobacco with Agrobacterium Carrying Plasmid pDAB2041

Tobacco transformation with *Agrobacterium tumefaciens* was carried out by a method similar, but not identical, to published methods (R Horsch et al, 1988. Plant Molecular Biology Manual, S. Gelvin et al, eds., Kluwer Academic Publishers, Boston). To provide source tissue for the transformation, tobacco seed (*Nicotiana tabacum* cv. Kentucky 160) were surface sterilized and planted on-the surface of TOB−, which is a hormone-free Murashige and Skoog medium (T. Murashige and F. Skoog, 1962). A revised medium for rapid growth and bioassays with tobacco tissue culture. Plant Physiol. 75: 473–497) solidified with agar. Plants were grown for 6–8 weeks in a lighted incubator room at 28–30° C. and leaves were collected sterilely for use in the transformation protocol. Approximately one $cm^2$ pieces were sterilely cut from these leaves, excluding the midrib. Cultures of the Agrobacterium strains (EHA101S containing pDAB2041), which had been grown overnight on a rotor at 28° C., were pelleted in a centrifuge and resuspended in sterile Murashige & Skoog salts, adjusted to a final optical density of 0.7 at 600 nm. Leaf pieces were dipped in this bacterial suspension for approximately 30 seconds, then blotted dry on sterile paper towels and placed right side up on medium TOB+ (Murashige and Skoog medium containing 1 mg/L indole acetic acid and 2.5 mg/L benzyladenine) and incubated in the dark at 28° C. Two days later the leaf pieces were moved to medium TOB+ containing 250 mg/L cefotaxime (Agri-Bio, North Miami, Fla.) and 100 mg/L kanamycin sulfate (AgriBio) and incubated at 28–30° C. in the light. Leaf pieces were moved to fresh TOB+ with cefotaxime and kanamycin twice per week for the first two weeks and once per week thereafter. Leaf pieces which showed regrowth of the Agrobacterium strain were moved to medium TOB+ with cefotaxime and kanamycin, plus 100 mg/l carbenicillin (Sigma). Four to six weeks after the leaf pieces were treated with the bacteria, small plants arising from transformed foci were removed from this tissue preparation and planted into medium TOB− containing 250 mg/L cefotaxime and 100 mg/L kanamycin in Magenta GA7 boxes (Magenta Corp., Chicago). These plantlets were grown in a lighted incubator room. After 3–4 weeks the primary transgenic plants had rooted and grown to a size sufficient that leaf samples could be analyzed for expression of protein from the transgene. Twenty-five independent transgenic events were recovered as single plants from the pDAB2041 transformation.

Eight independent lines expressing various levels of transgenic protein from the T-DNA of pDAB2041 were propagated in vitro from leaf pieces as follows. Twelve to sixteen approximately one cm² pieces were sterilely cut from leaves of each primary transgenic plant, excluding the midrib and all naturally occurring edges. These leaf pieces were placed on medium TOB+ containing 250 mg/L cefotaxime and 100 mg/L kanamycin, and cultured in the lighted incubator at 28–30° C. for 3–4 weeks, at which time small plants could be cut from the proliferating tissue mass. Several small plantlets from each transgenic line were moved into Magenta boxes containing medium TOB− plus cefotaxime and kanamycin and allowed to root and grow. The proliferating tissue mass was further cultured on medium TOB+ with cefotaxime and kanamycin, and additional plants could be cut out and grown up as needed.

Plants were moved into the greenhouse by washing the agar from the roots, transplanting into soil in 5½" square pots, placing the pot into a Ziploc bag (DowBrands), placing plain water into the bottom of the bag, and placing in indirect light in a 30° C. greenhouse for one week. After one week the bag could be opened; the plants were fertilized and allowed to grow further, until the plants were acclimated and the bag was removed. Plants were grown under ordinary warm greenhouse conditions (30° C., 16H light). Plants were suitable for sampling four weeks post transplant.

EXAMPLE 3

Chacterization of Transgenic Tobacco Plants Expressing Photorhabdus Toxin that Confer Insect Control A. Polyclonal Antibody Production The *E. coli* produced recombinant TcdA protein was purified by a series of column purification. The protein was sent to Berkley Antibody Company (Richmond, Calif.) for the production of antiserum in a rabbit. Inoculations with the antigen were initiated with 0.5 mg of protein followed by four boosting injections of 0.25 mg each at about three week intervals. The rabbit serum was tested by the standard Western analysis using the recombinant TcdA protein as the antigen and enhanced chemi-luminescens, ECL method (Amersham, Arlington Heights, Ill.) The antibodies (PAb-$EA_0$) were purified using a PURE I antibody purification kit (Sigma, St. Luis, Mo.). PAb-$EA_0$ antibodies recognize the full-length TcdA and its processed components.

B. Expression of TcdA Protein in Tobacco

Protein was extracted from the leaf tissue of transformed and non-transformed tobacco plants following the procedure described immediately below.

Two leaf disks of 1.4 cm in diameter were harvested from the middle portion of a fully expanded leaf. The disks were placed on a 1.6×4 cm piece of 3M Whatman paper. The paper was folded lengthwise and inserted in a flexible straw. Four hundred micro liters of the extraction buffer (9.5 ml of 0.2 M $NaH_2PO_4$, 15.5 ml of 0.2 M $Na_2HPO_4$, 2 ml of 0.5 M $Na_2EDTA$, 100 ml of Triton X100, 1 ml of 10% Sarkosyl, 78 ml of beta-mercaptoethanol, $H_2O$ to bring total volume to 100 ml) was pipetted on to the paper. The straw containing the sample was then passed through a rolling device used for squeezing out the extract 1.5 mL micro centrifuge tube was placed at the other end of the straw to collect the extract. The extract was centrifuged for 10 minutes at 14,000 rpm in an Eppendorf regrigerated microcentrifuge. The supernatant was transferred into a new tube. Protein quantitation analysis was performed using the standard Bio-Rad Protein Analysis protocol (Bio-Rad Laboratories, Hercules, Calif.). The extract was diluted to 2 mg/ml of total protein using the extraction buffer.

For the detection of transgenic protein, Western blot analysis was performed. Following a standard procedure for protein separation (Laemmli, 1970), 40 $\mu$g of protein was loaded in each well of 4–20% gradient polyacrylamide gel (Owl Scientific Co., MA) for electrophoresis. Subsequently, the protein was transferred onto a nitrocellulose membrane using a semi-dry electroblotter (Pharmacia LKB Biotechnology, Piscataway, N.J.). The membrane was incubated for one hour in Blotto (5% milk in TBST solution; 25 mM Tris HCL pH 7.4, 136 mM NaCl, 2.7 mM KCl, 0.1% Tween 20). Thereafter, Blotto was replaced by the primary antibody solution (in Blotto). After one hour in the primary antibody, the membrane was washed with TBST for five minutes three times. Then the secondary antibody in Blotto (1:2000 dilution of goat anti-rabbit IgG conjugated to horseradish peroxidase; Bio-Rad Laboratories). was added to the membrane. After one hour of incubation, the membrane was washed with an excess amount of TBST for 10 minutes four times. The protein was visualized by using the enhanced chemi-luminescens, ECL method (Amersham, Arlington Heights, Ill.). The differential intensity of the protein bands were measured using densitometer (Molecular Dynamics Inc., Sunnyvale, Calif.).

To determine the expression of TcdA protein in tobacco transformed with pDAB2041, PAb-$EA_0$ antibodies were used as the primary antibodies. The expression levels of TcdA protein varied among independent transformation events. The primary plant generated from the event #2041-13 showed the highest level of pre-pro TcdA expression of extractable protein. When the leaf pieces from this plant (#2041-13) were used in in vitro propagation, several plants were obtained. Seven of these plants were analyzed for the expression of the TcdA protein. All but one plant produced the full-length TcdA protein as well as some processed peptide components. Using the antibodies specific to Neomycin phospho-transferase, NPT (5 prime-3 prime, Boulder, Colo.), the expression the selectable marker gene (npt II) was detected. Similar results were obtained for #2041-29.

TABLE 5

Western analysis of plants derived from event #2041-13.

| Plant # | TcdA | NPT (selectable marker) |
|---|---|---|
| 2041-13A | + | not done |
| 2041-13B | + | not done |
| 2041-13-1 | − | + |
| 2041-13-2 | + | + |
| 2041-13-3 | + | + |
| 2041-13-4 | + | + |
| 2041-13-5 | + | + |

C. Nucleic Acid Analysis of Transgenic Tobacco Lines

Genomic DNA was prepared from a group of 2041 transgenic events. The lines included Magenta box stage 2041-13, and greenhouse stage plants 2041-13-1, 2041-13-2, 2041-13-5, 2041-9, 2041-20A and 2041-20B. A transgenic GUS line (2023) was included as a negative control. Southern analysis of these lines was performed. The genomic tobacco DNA was restricted with the enzyme SstI which should result in a 8.9 kb hybridization product when hybridized to a tcdA gene specific probe. The 8.9 kb hybridization product should consist of the 35T promoter and the tcdA coding region. All 2041 plants contained a band of the expected size. Events 2041-9 and -20 appear to be the same line with 5 identical hybridizing bands. Event 2041-13 produced 6 hybridization fragments with the tcdA coding region probe. Magenta box and various greenhouse plants of 2041-13 all produced the same hybridization profile. This hybridization pattern was different from that of events 2041-9 and -20.

RNA analysis, using the tcdA coding region probe, was performed on the same group of greenhouse 2041 plants. Immunoblot analysis had revealed that plants 2041-9, 2041-20A, 2041-20B, and 2041-13-1 produced no detectable TcdA protein; while 2041-13-2 and 2041-13-5 produced substantial amounts of full-length TcdA. Northern analysis was in agreement with the immunoblot result. A faint RNA signal was detected for plants 2041-9, 2041-20A, 2041-20B, and 2041-13-1. Only faintly visible was a band corresponding to full-length tcdA transcript in plant 2041-13.1. In contrast, for plants 2041-13-2 and 2041-13-5 a strong RNA signal was detected, with a substantial amount of full-length size (~8.0 kb) tcdA transcript. These data support the observed bioassay activity for this group of plants.

Genomic DNA was prepared from a second functionally active 2041 transgenic event, 2041-29. Southern analysis of this line was performed. A transgenic GUS line (2023) was included as a negative control, DNA of line 2041-9 was included as a positive control.

The genomic tobacco DNAs were restricted with the enzyme SstI which should result in a 8.9 kb hybridization product when hybridized to a tcdA gene specific probe. The 8.9 kb hybridization product should consist of the 35T promoter and the tcdA coding region. For plant 2041-29-5, three hybridization products larger than 8.9 kb the were detected with the tcdA gene specific probe. Immunoblot analysis has demonstrated pre-pro TcdA protein is made by this plant, it is therefore likely that a restriction site was lost during transformation or regeneration, or the 2041-29 genomic DNA was not thoroughly digested.

D. Tobacco Leaf-Disk Tests with Tobacco Hornworm Exhibiting Insect Control

Leaves were sampled from tobacco plants, *Nicotiana tabaco*, previously transplanted into the greenhouse. A single leaf was sampled from each plant on each test date. Leaves were selected from the zone where younger elongate leaves transition into older ovate leaves. Excised leaves were placed into 12 oz. cups with the petiole submerged in water to maintain turgor, and transported to the laboratory.

Eight, 1.4 cm disks were cut from the center portion of one side of each leaf (right adaxial side up, with distal portion facing away from the observer). Each disk was placed individually into a well of a C–D International 128 well tray (Pitman, N.J.) into which 0.5 ml of a 1.6% aqueous agar solution had been previously pipetted. The solidified agar prevented the leaf disks from drying out. The adaxial surface of the disk was always oriented up.

A single neonate tobacco hornworm, *Manduca sexta*, was placed on each disk and the wells were sealed with vented plastic lids. The assay was held at 27° C. and 40% RH. Larval mortality and live-weight data were collected after 3 days. Data were subjected to analysis of variance and Duncan's multiple range test ($\alpha$=0.05)(Proc GLM, SAS Institute Inc., Cary, N.C.). Data were transformed using a logarithmic function to correct a correlation between the magnitude of the mean and variance.

TABLE 6

Results of leaf-disk assays from greenhouse grown tobacco plants with event 2041-13.

| | | | Weight of Surviving Larvae (mg) & Duncan's Group[1] | | | | |
|---|---|---|---|---|---|---|---|
| TRT | Plant | Plant Age | Pretest | Test 1 | Test 2 | Test 3 | 3 Test Sum. |
| 13 | non-transformed-2 | young | — | — | — | 18.8 a* | — |
| 14 | non-transformed-3 | young | — | — | — | 17.0 ab | — |
| 16 | non-transformed-5 | young | — | — | — | 16.4 ab | — |
| 3 | 2041-13-1(western−) | young | — | 17.6 a | 18.2 a | 16.1 ab | 17.3 a |
| 9 | Gus Control | old | 19.3 a | 14.6 a | 16.3 a | 14.5 ab | 15.1 a |
| 10 | non-transformed-1 | young | — | 8.3 b | 16.8 a | 13.9 b | 13.0 b |
| 11 | 2041-20B(western−) | old | — | 10.0 b* | 13.7 ab | 14.6 ab | 12.9 b |
| 15 | non-transformed-4 | young | — | — | — | 13.0 bc | — |
| 8 | 2041-20A(western−) | old | 15.7 a | 8.3 b | 11.3 bc | 9.2 cd | 9.6 c |
| 12 | 2041-9(western−) | old | 19.5 a | — | — | 7.9 d | — |
| 7 | 2041-13-5(western+) | young | — | 6.3 bc | 9.6 cd | 7.2 de | 7.7 d |
| 5 | 2041-13-3(western+) | young | — | 6.4 bc**** | 6.2 e | 6.8 de** | 6.4 de |
| 1 | 2041-13A(western+) | old | 7.2 b | 6.8 bc* | 7.0 de* | 5.4 e | 6.4 de |
| 6 | 2041-13-4(western+) | young | — | 4.9 c**** | 5.8 e | 7.6 d | 6.4 de |
| 4 | 2041-13-2(western+) | young | — | 5.7 bc | 5.7 e** | 7.5 d | 6.3 de |
| 2 | 2041-13B(western +) | old | — | 4.7 c** | 5.6 e | 7.2 de | 5.9 e |

*Number of stars corresponds to the number of dead larvae per 8 tested.

[1]Data transformed (logarithm) for analysis. Means followed by the same letter are not significantly different (alpha = 0.05).

TABLE 7

Results Of Leaf-Disk Assays From Greenhouse Grown Tobacco Plants With Event 2041-29.

| | MEAN WGT (MG)/Duncan's Group | | | | |
|---|---|---|---|---|---|
| Plant | Test 1 | Test 2 | Test 3 | Test 4 | Four Test Summary |
| 2014-6 GUS 1 | 15.8 a | 16.6a | **5.5bc | *12.9ab | 13.2 a |
| 2014-6 GUS 2 | 14.4 a | *6.6 bc | *13.4a | 15.2a | 12.6 a |
| KY-160 NTC | 13.4 a | 6.7 bc | 7.9b | 8.5bc | 9.1 b |
| 2041-29 4P | *4.9 b | *7.3b | ****6.9b | ******** | 6.3 c |
| 2041-29 7 | *5.9 b | 5.1bc | ***6.7b | ***7.2c | 6.1 c |
| 2041-29 3P | *5.6 b | **7.9b | *****6.5b | ***3.6d | 5.9 c |
| 2041-29 2P | 6.3 b | ****4.7c | ******4.1c | ******4.6d | 5.4 c |

*Number of stars corresponds to the number of dead larvae per 8 tested.
[1]Data transformed (logarithm) for analysis. Means followed by the same letter are not significantly different (alpha = 0.05).

All event 2041-29 plants significantly depressed THW larval weight gain compared to control plants. Average weight depression was 49%. Statistically significant mortality occurred in THW larvae exposed to foliage from 2041-29 plants. Mortality averaged 37.5% compared to 5.2% in controls.

E. Isolation and Characterization of Functional Photorhabdus Toxin Protein from Transgenic Plants Seven grams of transgenic tobacco plants (2041-13) expressing TcdA (Toxin A) gene were homogenized with 10 ml 50 mM Potassium Phosphate buffer, pH 7.0 using a bead beater (Biospec Products, Bartlesville, Okla.) according to manufacturer's instructions. The homogenate was filtered through four layers of cheese cloth and then centrifuged at 35,000 g for 15 min. The supernant was collected and filtered through 0.22 μm Millipore ExpressT™ membrane. It was then applied to a Superdex 200 cloumn (2.6×40 cm) which had been equilibrated with 20 mM Tris buffer, pH 8.0 (Buffer A). The protein was eluted in Buffer A at a flow rate of 3 ml/min. Fractions with 3 ml each were collected and subjected to southern corn rootworm (SCR) bioassay. It was found that fractions corresponding to a native molecular weight around 860 kDa had the highest insecticidal activity. Western analysis of the active fraction using a polyclonal antibody specific to Toxin A indicated the presence of full-length TcdA peptide. The active fractions were further combined and applied to a Mono Q 10/10 column which had been equilibrated with Buffer A. Proteins bound to the column were then eluted by a linear gradient of 0 to 1 M NaCl in Buffer A. Fractions with 2 ml each were collected and analyzed by both SCR bioassay and Western using antibody specific to Toxin A. The results again demonstrated the correlation between insecticidal activity and presence of full-length TcdA peptide.

F. Characterization of Progeny Transgenic Plants

The inheritability of the genetically engineering plants containing the Photorhabdus toxin gene was evaluated by generating Fl progeny. Progeny was generated from 2041-13 event by selfing expression positive plants. The 2041-13 plants in the greenhouse were allowed to self-pollinate. Seed capsules were collected when mature and were allowed to dry and after-ripen on the laboratory bench for two weeks. Seed from plant designated 2041-13A was surface-sterilized and distributed on the surface of medium TOB− without selection, to allow recovery of nonexpressing or nontransgenic progeny as well as expressing and segregating transgenic siblings. Seed was germinated in a C lighted incubator room (16H light, 28 C). After 1 month, fifty-one seedlings, designated 2041-13A-S1 through S51, were distributed into Magenta boxes containing medium TOB− to grow further. Three weeks later, leaf samples from these Magenta-box grown seedlings were submitted for evaluation of the level of expression of TcdA toxin.

Leaf samples were tested for kanamycin response by placing sterile leaf segments on medium TOB+ containing 100 mg/L kanamycin in the light and scoring for tissue growth and color after two weeks. All leaf pieces showed some positive response, indicating complex segregation.

This group of in vitro grown event 2041-13 progeny seedlings were all transplanted into the greenhouse approximately two months after seeding onto medium, using the following method. After washing the agar from the roots, plants were transplanted into 5½ inch square pots in a soil mix containing 75% MetroMix and 25% mineral soil. They were enclosed in a zip-lock bag and plain water added to leave 1–2 inches of water in the bottom of the bag after soil absorption. These bags were closed and placed under a cart in the greenhouse to protect them from direct sunlight. The bags were opened after 5–6 days, and removed after 7 days, when the plants were adapted to soil and were moved to the top of the cart for normal greenhouse culture. Plants were ready to test in insect bioassays at four weeks post transplant.

F1 progeny were evaluated for expression of protein toxin by immunological screen and for biological activity by plant bioassays, as described previously, using tobacco hornworm. There existed a positive correlation between levels of expression protein toxin and degree of growth inhibition and at higher expression levels mortality was observed. The biological activity was observed to be statistical significance with high cofidence levels between populations of non-transformed and transformed expressing protein toxin.

The following table summarizes the results of insect (tobacco hornworm) bioassays conducted with Fl progeny of self-fertilized 2041-13 plants genetically engineered to produce the "204" A toxin. The tests included 6 non-expressing progeny (protein-negative controls), 45 toxin A expressors, and 4 non-transformed controls (KY-160). Results are from three leaf-disk assays (method previously outlined) where eight disks were used per test. The data were analyzed using analysis of variance and were blocked by test.

The treatment effect for each of these analyses indicated the Pr>F was less than 0.0001. The Toxin A expressors produced significant control of tobacco hornworm compared to each of the control groups based on each of the three measures of efficacy. The two control groups behaved similarly. Statistical analysis using ANOVA and an LSD test with alpha equal to 0.01 (or 1%) showed differences between the 3 groups. The LSD test indicated that the non-expressors and the non-transformed plants were similar in larvae weights but the expressors gave weights significantly lower than either of the other two groups of plants. These data demonstrated that the genetic basis for insect control was inheritable and corresponded to the presence of expressed toxin gene.

TABLE 8

Tobacco hornworm results from F1 progeny of self-fertilized 2041-13 tobacco plants.

| Treatment Group | Mean Value and Duncan's Grouping[d] | | |
|---|---|---|---|
| | Total Weight (mg)[a] | Survivor Weight (mg)[b] | Leaf Area (cm$^2$)[c] |
| Non-transformed Control | 15.8 a | 15.8 a | 1.2 a |
| Protein-negative Control | 16.4 a | 16.5 a | 1.2 a |
| Toxin A Expressor | 8.1 b | 9.2 b | 4.9 b |

[a]Average insect weight with dead insects considered to weigh nothing.
[b]Average insect weight with dead insects excluded from analysis.
[c]Total leaf area remaining per eight leaf disks. Initial area was approximately 12 cm$^2$.
[d]Means followed by the same letter are not significantly different (alpha = 0.05).

EXAMPLE 4

Transformation of Maize with a Vector Carrying Plasmid pDAB1834 Encoding Photorhabdus Toxins A. Preparation of Maize Transformation Vectors Containing Modified Plant-Optimized tcdA Coding Regions: Plasmid Pdab1834

Preparation of maize transformation vectors was accomplished in two steps. First, a modified plant-optimized tcdA coding region was ligated into a plant expression cassette plasmid. In this step, the coding region was placed under the transcriptional control of a promoter functional in maize plant cells. RNA transcription termination and polyadenylation were mediated by a downstream copy of the terminator region from the *Agrobacterium nopaline* synthase gene. One plasmid designed to function in this role is pDAB1538. In the second step, the complete gene comprised of the promoter, coding region, and 3' UTR terminator region was ligated to a plant transformation vector that contained a plant expressible selectable marker gene which allowed the selection of transformed maize plant cells amongst a background of nontransformed cells. An example of such a vector is pDAB367.

It is a feature of plasmid pDAB1538 that any coding region having an NcoI site at its 5' end and a SacI site 3' to the coding region, when cloned into the unique NcoI and SacI sites of pDAB1538, is placed under the transcriptional control of the maize ubiquitin1 (ubi1) promoter. It is also a feature of pDAB1538 that the 5' untranslated leader (UTR) sequence preceding the NcoI site comprises a polylinker. Additionally it is a feature of pDAB1538 that transcription termination and polyadenylation of the mRNA containing the introduced coding region are mediated by termination/Poly A addition sequences derived from the nopaline synthase (Nos) gene. Finally, it is a feature of pDAB1538 that the entire assembly of promoter/coding region/3'UTR can be obtained as a single DNA fragment by cleavage at the flanking NotI sites.

It is a feature of pDAB367 that the phosphinothricin acetyl transferase protein, which has as its substrate phosphinothricin and related compounds, is produced in plant cells through transcription of its coding region mediated by the Cauliflower Mosaic Virus 35S promoter and that termination of transcription plus polyadenylation are mediated by the nopaline synthase terminator region. It is further a feature of pDAB367 that any DNA fragment containing flanking NotI sites can be cloned into the unique NotI site of pDAB367, thus physically linking the introduced DNA fragment to the aforementioned selectable marker gene.

To prepare a maize plant-expressible gene to produce the endoplasmic reticulum-targeted TcdA protein in plant cells, DNA of a plasmid (pA0H_4-ER) containing the plant-optimized, ER-targeted tcdA coding region, (SEQ ID No:6) was cleaved with restriction enzymes NcoI and SacI, and the large 7610 bp fragment was ligated to similarly-cut DNA of plasmid pDAB1538 to produce plasmid pDAB1832. DNA of pDAB1832 was then digested with NotI, and the 9984 bp NotI fragment was ligated into the unique NotI site of pDAB367 to produce plasmid pDAB1834.

It is a feature of plasmids pDAB1834 that the ubi1 and 35S promoters are encoded on the same DNA strand.

B. Transformation and Regeneration of Transgenic Maize Isolates

Type II callus cultures were initiated from immature zygotic embryos of the genotype "Hi-II." (Armstrong et al, (1991) Maize Genet. Coop. Newslett., 65: 92–93). Embryos were isolated from greenhouse-grown ears from crosses between Hi-II parent A and Hi-II parent B or $F_2$ embryos derived from a self- or sib-pollination of a Hi-II plant. Immature embryos (1.5 to 3.5 mm) were cultured on initiation medium consisting of N6 salts and vitamins (Chu et al, (1978) *The N6 medium and its application to anther culture of cereal crops*. Proc. Symp. Plant Tissue Culture, Peking Press, 43–56), 1.0 mg/L 2,4-D, 25 mM L-proline, 100 mg/L casein hydrolysate, 10 mg/L $AgNO_3$, 2.5 g/L GELRITE (Schweizerhall, South Plainfield, N.J.), and 20 g/L sucrose, with a pH of 5.8. After four to six weeks callus was subcultured onto maintenance medium (initiation medium in which $AgNO_3$ was omitted and L-proline was reduced to 6 mM). Selection for Type II callus took place for ca. 12–16 weeks.

Plasmid pDAB1834 was transformed into embryogenic callus. For blasting, 140 $\mu$g of plasmid DNA was precipitated onto 60 mg of alcohol-rinsed, spherical gold particles (1.5–3.0 $\mu$m diameter, Aldrich Chemical Co., Inc., Milwaukee, Wis.) by adding 74 $\mu$L of 2.5M $CaCl_2H_2O$ and 30 $\mu$L of 0.1M spermidine (free base) to 300 $\mu$L of plasmid DNA and $H_2O$. The solution was immediately vortexed and the DNA-coated gold particles were allowed to settle. The resulting clear supernatant was removed and the gold particles were resuspended in 1 ml of absolute ethanol. This suspension was diluted with absolute ethanol to obtain 15 mg DNA-coated gold/mL.

Approximately 600 mg of embryogenic callus tissue was spread over the surface of Type II callus maintenance medium as described herein lacking casein hydrolysate and L-proline, but supplemented with 0.2 M sorbitol and 0.2 M mannitol as an osmoticum. Following a 4 h pre-treatment, tissue was transferred to culture dishes containing blasting medium (osmotic media solidified with 20 g/L TC agar (PhytoTechnology Laboratories, LLC, Shawnee Mission, Kans.) instead of 7 g/L GELRITE. Helium blasting accelerated suspended DNA-coated gold particles towards and into the prepared tissue targets. The device used was an earlier prototype of that described in U.S. Pat. No. 5,141,131 which is incorporated herein by reference. Tissues were covered with a stainless steel screen (104 μm openings)and placed under a partial vacuum of 25 inches of Hg in the device chamber. The DNA-coated gold particles were further diluted 1:1 with absolute ethanol prior to blasting and were accelerated at the callus targets four times using a helium pressure of 1500 psi, with each blast delivering 20 μL of the DNA/gold suspension. Immediately post-blasting, the tissue was transferred to osmotic media for a 16–24 h recovery period. Afterwards, the tissue was divided into small pieces and transferred to selection medium (maintenance medium lacking casein hydrolysate and L-proline but containing 30 mg/L BASTA® (AgrEvo, Berlin, Germany)). Every four weeks for 3 months, tissue pieces were non-selectively transferred to fresh selection medium. After 7 weeks and up to 22 weeks, callus sectors found proliferating against a background of growth-inhibited tissue were removed and isolated. The resulting BASTA®-resistant tissue was subcultured biweekly onto fresh selection medium. Following western analysis, positive transgenic lines were identified and transferred to regeneration media. Western-negative lines underwent subsequent RNA spot blot analysis to identify negative controls for regeneration.

Regeneration was initiated by transferring callus tissue to cytokinin-based induction medium, which consisted of Murashige and Skoog salts, hereinafter MS salts, and vitamins (Murashige and Skoog, (1962) Physiol. Plant. 15: 473–497) 30 g/L sucrose, 100 mg/L myo-inositol, 30 g/L mannitol, 5 mg/L 6-benzylaminopurine, hereinafter BAP, 0.025 mg/L 2,4-D, 30 mg/L BASTA®, and 2.5 g/L GELRITE at pH 5.7. The cultures were placed in low light (125 ft-candles) for one week followed by one week in high light (325 ft-candles). Following a two week induction period, tissue was non-selectively transferred to hormone-free regeneration medium, which was identical to the induction medium except that it lacked 2,4-D and BAP, and was kept in high light. Small (1.5–3 cm) plantlets were removed and placed in 150×25 mm culture tubes containing SH medium (SH salts and vitamins (Schenk and Hildebrandt, (1972) Can. J. Bot. 50:199–204), 10 g/L sucrose, 100 mg/L myo-inositol, 5 mL/L FeEDTA, and 2.5 g/L GELRITE, pH 5.8). Plantlets were transferred to 12 cm pots containing approximately 0.25 kg of METRO-MIX 360 (The Scotts Co. Marysville, Ohio) in the greenhouse as soon as they exhibited growth and developed a sufficient root system. They were grown with a 16 h photoperiod supplemented by a combination of high pressure sodium and metal halide lamps, and were watered as needed with a combination of three independent Peters Excel fertilizer formulations (Grace-Sierra Horticultural Products Company, Milpitas, Calif.). At the 6–8 leaf stage, plants were transplanted to five gallon pots containing approximately 4 kg METRO-MIX 360, and grown to maturity.

EXAMPLE 5

Characterization Of Transgenic Maize Plants Expressing Photorhabdus Toxin That Confer Insect Control A. Insect Bioassays A single leaf was sampled from each plant in each test. Eight, 1.4 cm disks were cut from the outer portion of each leaf (approximately 30 cm long) avoiding the center vein. Each disk was placed individually into a well of a C–D International 128 well tray (Pitman, N.J.) into which 0.5 ml of a 1.6% aqueous agar solution had been previously pipetted. The solidified agar prevented the leaf disks from drying out. The adaxial surface of the disk was always oriented up.

Five neonate southern corn rootworms, Diabrotica undecimpunctata howardi, were placed on each disk and the wells were sealed with vented plastic lids. The assay was held at 27° C. and 40% RH. Larval mortality and live-weight data were collected after 3 days. Data were subjected to analysis of variance and Duncan's multiple range test ($\alpha$=0.05)(Proc GLM, SAS Institute Inc., Cary, N.C.). Weight data were transformed using a logarithmic function to correct a correlation between the magnitude of the mean and variance.

TABLE 9

Results of Maize Leaf-disk Test vs SCR

| Treatment | Mean % Kill (Duncan's) | Mean Survival Weight (mg) (Duncan's) |
|---|---|---|
| 1834 - 11 | 68 A | 0.064 A |
| 1834 - 17 | 44 B | 0.093 B |
| 1834 - 15 | 26 BC | 0.127 C |
| HiII control | 13 C | 0.161 C |

Note: Means followed by the same letter are not significantly different based on Duncan's multiple range test (alpha = 0.05). Insect groups weighing less than 0.1 mg were set to 0.03 mg instead of zero to conduct a more conservative analysis. Mortality (arcsin(sqrt)) and weight(log10) data were transformed for analyses.

The results shown in Table 9 demonstrated that two events expressing TcdA protein were statistically distinct from control lines bioassayed using SCR neonates by mortality and survival weight criteria. These results demonstrated that southern corn rootworm were functionally effected by feeding on maize plants containing and expressing the tcdA gene. Those plants from 1834-11 were used to generate progeny for testing of inheritability of transgene.

B. Production and Progeny Test of tcdA Transgenic Maize

Origin and growth of progeny plants: Sibling plants 1834-11-07 and 1834-11-08, clonally derived by regeneration from the callus of transgenic maize event 1834-11, were transplanted to the greenhouse and pollinated with inbred OQ414. Seeds obtained from these crosses, comprising seed lots 1834-11-07A and 1834-11-08A, were planted in Rootrainers (1½ inch×2 inch×8 inch deep, product #647, C. Hummert Intl., Earth City, Mo.) filled with Metro-Mix 360 soilless mix (Scotts Terra-Lite, available from Hummert Intl.) and top irrigated with Hoagland's nutrient solution. (Hoagland's solution contains 229 ppm nitrogen as nitrate, 24.6 ppm nitrogen as ammonium, 26 ppm P, 157 ppm K, 187 ppm Ca, 49 ppm Mg. and 30 ppm Na.)

Greenhouse conditions for this trial were: 16 hour days, daylight supplemented by metal halide lamps as needed to achieve a minimum of 600 ?Einsteins/cm$^2$ PAR, and ambient temperature 30 C days, 22 C nights.

Leaves were sampled for protein determination approximately one week after planting. Leaf bioassays were conducted 2–3 weeks after planting; root bioassays were initiated approximately 3 weeks post planting.

Protein analysis of progeny plants: Protein was extracted from leaf and root samples harvested from transgenic plants, line 1834-11 progenies, and non-transformed plants. Each sample was placed on a 1.6×4 cm piece of 3M Whatman T paper. The paper was folded lengthwise and inserted in a flexible straw. A volume of 350 $\mu$l of an extraction buffer (9.5 ml of 0.2 M $NaH_2PO_4$, 15.5 ml of 0.2 M $Na_2HPO_4$, 2 ml of 0.5 M $Na_2$EDTA, 100 ml of Triton X-100, 1 ml of 10% Sarkosyl, 78 ml of beta-mercaptoethanol, $H_2O$ to bring total volume to 100 ml, 50 $\mu$g/ml Antipain, 50 $\mu$g/ml Leupeptin, 0.1 mM Chymostatin, 5 $\mu$g/ml Pepstatin) was pipetted on to the paper. The straw containing the sample was then passed through a rolling device used for squeezing the extract into a 1.5 ml microcentrifuge tube. The extract was centrifuged for 10 minutes at 14,000 rpm in an Eppendorf refrigerated micro-centrifuge. The supernatant was transferred into a new tube. The amount of the total extractable protein was determined using a standard BioRad Protein Analysis protocol (BioRad Laboratories, Hercules, Calif.).

The presence of the TcdA protein was visualized by Western blot analysis following a standard procedure for protein separation (Laemmli, 1970). A volume of twenty µl of extract was loaded in each well of 4–20% gradient polyacrylamide gel (Owl Scientific Co., MA) for electrophoresis. Subsequently, the protein was transferred onto a nitrocellulose membrane using a semi-dry electroblotter (Pharmacia LKB Biotechnology, Piscataway, N.J.). The membrane was incubated for one hour in TBST-M solution (10% milk in TBST solution; 25 mM Tris HCL pH 7.4, 136 mM NaCl, 2.7 mM KCl, 0.1% Tween 20). Thereafter, the primary antibody (Anti-TcdA in TBST-M) was added. After one hour, the membrane was washed with TBST for five minutes, three times. Then the secondary antibody solution (goat anti-rabbit IgG conjugated to horseradish peroxidase; Bio-Rad Laboratories, in TBST-M) was added to the membrane. After one hour of incubation, the membrane was washed with an excess amount of TBST for 10 minutes, four times. The protein was visualized using the Super Signal® West Pico chemiluminescence method (Pierce Chemical Co., Rockford, Ill.). The protein blot was exposed on a Hyper-film (Amersham, Arlington Heights, Ill.) and was developed within 3 minutes. The intensity of the protein band was measured using a densitometer (Molecular Dynamics Inc., Sunnyvale, Calif.) and compared to standards.

Three of six plants from seed lot 1834-11-07A and three of six plants from seed lot 1834-11-08A produced detectable levels of TcdA protein (Table 1). Approximately 3.8 to 13.3 ppm of TcdA were detected in the leaf blades and 4.1 to 8.4 ppm were detected in the leaf tips of the protein-positive plants. The amounts of TcdA protein detected in the roots were slightly lower than those found in the leaves.

Insect bioassays with progeny plants: Plants were selected for bioassay based on results from Western blot analysis. Twelve (12), 6.4 mm diameter leaf discs were cut from the youngest leaf of each 2 week old seedling. Each disc was placed in a well of a 128-well tray (CD International) containing approximately 0.5 mL of a solidified 2% agar in water solution. Two neonate southern corn rootworm, *Diabrotica undecimpunctata* howardi (Barber) (SCR), were placed in each well with a leaf disc. Trays were covered with perforated lids and maintained under a controlled environment for 3 days (28 C; 16 hours light:8 hours dark; approx. 60% relative humidity). Living larvae from 4 leaf discs were pooled and weighed producing 3 weight determinations per plant. Average weights were calculated by dividing the pooled weight by the number of survivors. Differences in average weights of SCR fed leaf discs from protein positive and protein negative plants were assessed using analysis of variance on the natural log-transformed average weights (Minitab, v. 12.2, Minitab Inc., State College, Pa.).

Root bioassays were initiated approximately 1 week after the initiation of the leaf disc bioassays. Approximately 24 h prior to eclosion, SCR eggs were suspended in a 0.15% solution of agar in water to a concentration of 100 eggs/ml. Plants were inoculated with SCR eggs by pipetting 2.0 ml of the egg suspension (ie., approximately 200 eggs) just below the soil surface at the base of each plant. Two weeks after inoculation, plants were removed from their Rootrainer pots, their roots washed free of potting mix, and scored for rootworm damage based on a 1 (resistant) to 9 (susceptible) rating system (Welch, 1977). The results of the root ratings were examined using non-parametric tests to determine if the distribution of root ratings from the protein positive plants was the same as the distribution of the ratings from the protein negative plants. Testing was done at the 5% significance level. (StatXact v.3, CYTEL Software Corporation, Cambridge Mass.)

Results from leaf and root bioassays of tcdA protein positive and protein negative progeny plants are summarized in Table 10. The average weights of SCR larvae fed leaf discs from protein positive plants were significantly lower than those of larvae fed leaf discs from protein negative plants (F=4.6; d.f.=1, 34; P≦0.001. The Kolmogorov-Smirnov 2 sample test (p=0.04) and the Wald Wolfowitz runs test (p=0.001) indicated that the protein positive and protein negative root rating distributions were not similar. The Wilcoxon-Mann-Whitney test (p=0.0206) and the Normal Scores test (p=0.206) indicated that the average score for the protein positive plants was lower than the average root rating from the protein negative plants.

TABLE 10

Protein analysis and insect bioassay results with progeny of TcdA transgenic maize.

| Plant Number | TcdA Protein | Leaf Disc Bioassay Avg. Wt. (mg) | Root Bioassay Root Rating (1–9) |
|---|---|---|---|
| 1834-11-07A-30 | PRO− | 0.190 | 8 |
| 1834-11-08A-21 | PRO− | 0.196 | 9 |
| 1834-11-08A-16 | PRO− | 0.195 | 9 |
| 1834-11-08A-14 | PRO− | 0.137 | 9 |
| 1834-11-07A-22 | PRO− | 0.208 | 9 |
| 1834-11-07A-20 | PRO− | 0.175 | 9 |
| 1834-11-07A-26 | PRO+ | 0.118 | 9 |
| 1834-11-08A-17 | PRO+ | 0.132 | 8 |
| 1834-11-07A-14 | PRO+ | 0.110 | 2 |
| 1834-11-07A-11 | PRO+ | 0.106 | 4 |
| 1834-11-08A-28 | PRO+ | 0.129 | 8 |
| 1834-11-08A-27 | PRO+ | 0.108 | 4 |

DNA analysis of progeny plants: Leaf samples from 1834-11.7A and 1834-11.8A progeny plants were in conical 50 ml polypropylene tubes and dried in a Labconco Freeze Dry Lyophilizer (Kansas City, Mo.) for 1–2 days. Lyophilized leaves were then ground in a Tecator Cyclotec 1093 Sample mill grinder (Hoganas, Sweden) and stored at −20C. Genomic DNA was extracted by the following procedure: (1) to a 25 ml Conical tube containing 300–500 mg of ground tissue, 9 ml of CTAB (cetyl trimethylammonium bromide solution) was added, and incubated at 65° C. for 1 hour; (2) 4.5 ml of chloroform: octanol (24:1) was added and mixed gently for 5 minutes; (3) samples were centrifuged at 2000 rpm and DNA was precipitated from the supernatant with an equal volume of isopropanol; (4) DNA was collected on a glass hook, washed in ethanol, and dissolved in TE (10 mM Tris.HCl, 0.5 mM EDTA, pH 8.0).

Genomic DNA was digested at 37° C. for 2 hours in an Eppendorf tube containing the following mixture: 8 μl of 800 ug/ml DNA, 2 μl 1 mg/ml BSA (Bovine serum albumin),2 μl 10× buffer, 1 μl SacI, 1 μl EcoRI, and 6 μl $H_2O$. Digested DNA samples were electrophoresed overnight at 40 mA in a 0.85% SeaKem LE agarose gel(FMC, Rockland, Me.). The gel was blotted onto Millipore Immobilon-Ny+ (Bedford, Mass.) membrane overnight in 20×SSC (NaCl 175.2 g/l, Na citrate 88 g/l). The probe DNA was cut with BamHI/SacI (NEB, Beverly, Mass.) from pDAB1551 plasmid, which released a 7356 bp fragment containing the open reading frame of the rebuilt tcdA gene. This 7356 bp fragment was labeled with P32 using a Stratagene Prime-it RmT dCTP-Labeling Reactions kit (La Jolla, Calif.) and used for Southern hybridization. Hybridization was conducted in hybridization buffer (10% polyethylene glycol, 7% SDS [Sodium dodecyl sulfate], 0.6× SSC, 10 mM $NaPO_4$, 5 mM EDTA, 10 µg/ml denatured salmon sperm) at 60° C. overnight. After hybridization, the membrane was washed with 10×SSC plus 0.1% SDS at 60° C. for 30 min and exposed to X ray film (Hyperfilm® MP, Amershan Life Sciences, Piscataway, N.J.) for 1–2 days.

Results summarized indicate that a pattern of 8 hybridizing bands (the size of the expected fragment and larger) cosegregated with protein expression in 50% of all progeny assayed. These results are characteristic of a complex insertion at a single site. All seedlings containing the insert also expressed toxin protein.

EXAMPLE 6

Transformation of Rice with a Vector Carrying Plasmid pDAB1553 Encoding Photorhabdus Toxins A. Plasmid pDAB1553

Plasmid pDAB1553 containing tcdA driven by the maize ubiquitin1 promoter and hpt (hygromycin phosphotransferase providing resistance to the antibiotic hygromycin) under the control of 35T (a modified 35S promoter), was used for transformation.

Preparation of rice transformation vectors was accomplished in two steps. First, a modified plant-optimized tcdA coding region was ligated into a rice plant expression cassette plasmid. In this step, the coding region was placed under the transcriptional control of a promoter functional in plant cells. RNA transcription termination and polyadenylation were mediated by a downstream copy of the terminator region from the *Agrobacterium nopaline* synthase gene. One plasmid designed to function in this role is plasmid pDAB1538 (described in the section on maize transformation vectors). In the second step, the complete gene comprised of the promoter, coding region, and terminator region was ligated to a rice plant transformation vector that contained a plant expressible selectable marker gene which allowed the selection of transformed rice plant cells amongst a background of nontransformed cells. An example of such a vector is pDAB354-Not1.

It is a feature of pDAB354-Not1 that the hygromycin phosphotransferase protein, which has as its substrate hygromycin B and related compounds, is produced in plant cells through transcription of its coding region mediated by the Cauliflower Mosaic Virus 35S promoter and that termination of transcription plus polyadenylation are mediated by the nopaline synthase terminator region. It is further a feature of pDAB354-Not1 that any DNA fragment containing flanking NotI sites can be cloned into the unique NotI site of pDAB354-Not1, thus physically linking the introduced DNA fragment to the aforementioned selectable marker gene.

To prepare a plant-expressible gene to produce the non-targeted TcdA protein in rice plant cells, DNA of a plasmid (pAOH_4-OPTI) containing the plant-optimized tcdA coding region, (SEQ ID No:3) was cleaved with restriction enzymes NcoI and SacI, and the large 7550 bp fragment was ligated to similarly-cut DNA of plasmid pDAB1538 to produce plasmid pDAB1551. DNA of pDAB1551 was then digested with NotI, and the large 9933 bp fragment was ligated to NotI digested DNA of pDAB354-NotI to produce plasmid pDAB1553.

It is a feature of plasmid pDAB1553 that the ubil and 35S promoters are encoded on the same DNA strand.

B. Production of Rice Transgenics

For initiation of embryogenic callus, mature seeds of a *Japonica cultivar*, Taipei 309 were dehusked and surface-sterilized in 70% ethanol for 2–5 min. followed by a 30–45 min soak in 50% commercial bleach (2.6% sodium hypochlorite) with a few drops of 'Liquinox' soap. The seeds were then rinsed 3 times in sterile distilled water and placed on filter paper before transferring to 'callus induction' medium (i.e., NB). The NB medium consisted of N6 macro elements (Chu, 1978, The N6 medium and its application to anther culture of cereal crops. Proc. Symp. Plant Tissue Culture, Peking Press, p43–56), B5 micro elements and vitamins (Gamborg et al., 1968, Nutrient requirements of suspension cultures of soybean root cells. Exp. Cell Res. 50: 151–158), 300 mg/L casein hydrolysate, 500 mg/L L-proline, 500 mg/L L-glutamine, 30 g/L sucrose, 2 mg/L 2,4-dichloro-phenoxyacetic acid (2,4-D), and 2.5 g/L gelrite (Schweizerhall, N.J.) with the pH adjusted to 5.8. The mature seed cultured on 'induction' media were incubated in the dark at 28° C. After 3 weeks of culture, the emerging primary callus induced from the scutellar region of mature embryo was transferred to fresh NB medium for further maintenance.

About 140 μg of plasmid pDAB1553 DNA was precipitated onto 60 mg of 1.0 micron (Bio-Rad) gold particles as described herein.

For helium blasting, actively growing embryogenic callus cultures, 2–4 mm in size, were subjected to a high osmoticum treatment. This treatment included placing of callus on NB medium with 0.2 M mannitol and 0.2 M sorbitol (Vain et al., 1993, Osmoticum treatment enhances particle bombardment-mediated transient and stable transformation of maize. Plant Cell Rep. 12: 84–88) for 4 h before helium blasting. Following osmoticum treatment, callus cultures were transferred to 'blasting' medium (NB+2% agar) and covered with a stainless steel screen (230 micron). The callus cultures were blasted at 2,000 psi helium pressures twice per target. After blasting, callus was transferred back to the media with high osmoticum overnight before placing on selection medium, which consisted NB medium with 30 mg/L hygromycin. After 2 weeks, the cultures were transferred to fresh selection medium with a higher concentration of selection agent, i.e., NB+50 mg/L hygromycin (Li et al., 1993, An improved rice transformation system using the biolistic method. Plant Cell Rep. 12: 250–255).

Compact, white-yellow, embryogenic callus cultures, recovered on NB+50 mg/L hygromycin, were regenerated by transferring to 'pre-regeneration' (PR) medium+50 mg/L hygromycin. The PR medium consisted of NB medium with 2 mg/L benzyl aminopurine (BAP), 1 mg/L naphthalene acetic acid (NAA), and 5 mg/L abscisic acid (ABA). After 2 weeks of culture in the dark, they were transferred to 'regeneration' (RN) medium. The composition of RN medium is NB medium with 3 mg/L BAP, and 0.5 mg/L NAA. The cultures on RN medium were incubated for 2 weeks at 28° C. under high fluorescent light (325-ft-candles). The plantlets with 2 cm shoot were transferred to ½ MS medium (Murashige and Skoog, 1962, A revised medium for rapid growth and bioassays with tobacco tissue cultures. Physiol. Plant.15:473–497) with ½ B5 vitamins, 10 g/L sucrose, 0.05 mg/L NAA, 50 mg/L hygromycin and 2.5 g/L gelrite adjusted to pH 5.8 in magenta boxes. When plantlets were established with well-developed root systems, they were transferred to soil (1 metromix: 1 top soil) and raised in the greenhouse (29/24° C. day/night cycle, 50–60% humidity, 12 h photoperiod) until maturity.

EXAMPLE 7

Chacterization of Transgenic Rice Plants Expressing Photorhabdus Toxin that Confer Insect Control.

A. Insect Bioassays

Insect bioassays were performed using leaf discs and shown to be highly effective in controlling Southern corn rootworm. *Diabrotica undecimpunctata* howardi eggs are obtained from French Ag Research and hatched in petri dishes held at 28.5° C. and 40% RH. The aerial parts are sampled from the transgenic plants and placed, singly into inverted petri dishes (100×15 mm) containing 15 ml of 1.6% aqueous agar in the bottom to provide humidity and filter paper in the top to absorb condensation. These preparations are infested with five neonate larvae per dish and held at 28.5° C. and 40% RH for 3 days. Mortality and larval weights are recorded. Weight data were transformed using a logarithmic function to correct a correlation between the magnitude of the mean and variance.

TABLE 11

| Treatment | Average Survivor Weight in mg[1] (Duncan's Grouping) | Presence TcdA greenhouse-grown plants (number of +/ number of plants tested) |
| --- | --- | --- |
| GUS Control | 0.390 A | – |
| 1553-33 | 0.170 BCD | ++ |
| 1553-44 | 0.167 BCD | +++ |
| 1553-62 | 0.125 CD | +++ |
| 1553-41 | 0.100 D | +++ |

Note: Means followed by the same letter are not significantly different based on Duncan's multiple range test (alpha = 0.05).

Insect groups weighing less than 0.1 mg were set to 0.03 mg instead of zero to conduct a more conservative analysis. Weight data were transformed (Log10) for analyses. A single replicate was used on each of three test dates. Plants were sampled from magenta boxes.

The results demonstrate that in leaf disc bioassays, several rice events derived by transformation with tcdA gene were demonstrated to statistically have a functional affect on corn rootworm neonate.

We claim:

1. An isolated nucleic acid comprising the sequence of SEQ ID NO: 4.
2. A transgenic monocot plant cell comprising a nucleic acid comprising the sequence of SEQ ID NO: 4.
3. A transgenic dicot plant cell comprising a nucleic acid comprising the sequence of SEQ ID NO: 4.
4. A transgenic plant comprising a nucleic acid of SEQ ID NO:4 that imparts insect resistance.
5. The transgenic plant of claim 4 wherein the plant is rice.
6. The transgenic plant of claim 4 wherein the plant is maize.
7. The transgenic plant of claim 4 wherein the plant is tobacco.

* * * * *

SEQUENCE LISTING

```
<160> NUMBER OF SEQ ID NOS: 6

<210> SEQ ID NO 1
<211> LENGTH: 7551
<212> TYPE: DNA
<213> ORGANISM: Photorhabdus luminescens
<220> FEATURE:
<221> NAME/KEY: CDS
<222> LOCATION: (1)..(7548)

<400> SEQUENCE: 1 atg aac gag tct gta aaa gag ata cct gat gta tta aaa agc cag tgt      48
Met Asn Glu Ser Val Lys Glu Ile Pro Asp Val Leu Lys Ser Gln Cys
  1               5                  10                  15 ggt ttt aat tgt ctg aca gat att agc cac agc tct ttt aat gaa ttt      96
Gly Phe Asn Cys Leu Thr Asp Ile Ser His Ser Ser Phe Asn Glu Phe
             20                  25                  30 cgc cag caa gta tct gag cac ctc tcc tgg tcc gaa aca cac gac tta     144
Arg Gln Gln Val Ser Glu His Leu Ser Trp Ser Glu Thr His Asp Leu
         35                  40                  45 tat cat gat gca caa cag gca caa aag gat aat cgc ctg tat gaa gcg     192
Tyr His Asp Ala Gln Gln Ala Gln Lys Asp Asn Arg Leu Tyr Glu Ala
     50                  55                  60 cgt att ctc aaa cgc gcc aat ccc caa tta caa aat gcg gtg cat ctt     240
Arg Ile Leu Lys Arg Ala Asn Pro Gln Leu Gln Asn Ala Val His Leu
 65                  70                  75                  80 gcc att ctc gct ccc aat gct gaa ctg ata ggc tat aac aat caa ttt     288
Ala Ile Leu Ala Pro Asn Ala Glu Leu Ile Gly Tyr Asn Asn Gln Phe
                 85                  90                  95 agc ggt aga gcc agt caa tat gtt gcg ccg ggt acc gtt tct tcc atg     336
Ser Gly Arg Ala Ser Gln Tyr Val Ala Pro Gly Thr Val Ser Ser Met
            100                 105                 110 ttc tcc ccc gcc gct tat ttg act gaa ctt tat cgt gaa gca cgc aat     384
```

```
            Phe Ser Pro Ala Ala Tyr Leu Thr Glu Leu Tyr Arg Glu Ala Arg Asn
                        115                 120                 125 tta cac gca agt gac tcc gtt tat tat ctg gat acc cgc cgc cca gat              432
Leu His Ala Ser Asp Ser Val Tyr Tyr Leu Asp Thr Arg Arg Pro Asp
    130                 135                 140 ctc aaa tca atg gcg ctc agt cag caa aat atg gat ata gaa tta tcc              480
Leu Lys Ser Met Ala Leu Ser Gln Gln Asn Met Asp Ile Glu Leu Ser
145                 150                 155                 160 aca ctc tct ttg tcc aat gag ctg tta ttg gaa agc att aaa act gaa              528
Thr Leu Ser Leu Ser Asn Glu Leu Leu Leu Glu Ser Ile Lys Thr Glu
                165                 170                 175 tct aaa ctg gaa aac tat act aaa gtg atg gaa atg ctc tcc act ttc              576
Ser Lys Leu Glu Asn Tyr Thr Lys Val Met Glu Met Leu Ser Thr Phe
            180                 185                 190 cgt cct tcc ggc gca acg cct tat cat gat gct tat gaa aat gtg cgt              624
Arg Pro Ser Gly Ala Thr Pro Tyr His Asp Ala Tyr Glu Asn Val Arg
        195                 200                 205 gaa gtt atc cag cta caa gat cct gga ctt gag caa ctc aat gca tca              672
Glu Val Ile Gln Leu Gln Asp Pro Gly Leu Glu Gln Leu Asn Ala Ser
    210                 215                 220 ccg gca att gcc ggg ttg atg cat caa gcc tcc cta ttg ggt att aac              720
Pro Ala Ile Ala Gly Leu Met His Gln Ala Ser Leu Leu Gly Ile Asn
225                 230                 235                 240 gct tca atc tcg cct gag cta ttt aat att ctg acg gag gag att acc              768
Ala Ser Ile Ser Pro Glu Leu Phe Asn Ile Leu Thr Glu Glu Ile Thr
                245                 250                 255 gaa ggt aat gct gag gaa ctt tat aag aaa aat ttt ggt aat atc gaa              816
Glu Gly Asn Ala Glu Glu Leu Tyr Lys Lys Asn Phe Gly Asn Ile Glu
            260                 265                 270 ccg gcc tca ttg gct atg ccg gaa tac ctt aaa cgt tat tat aat tta              864
Pro Ala Ser Leu Ala Met Pro Glu Tyr Leu Lys Arg Tyr Tyr Asn Leu
        275                 280                 285 agc gat gaa gaa ctt agt cag ttt att ggt aaa gcc agc aat ttt ggt              912
Ser Asp Glu Glu Leu Ser Gln Phe Ile Gly Lys Ala Ser Asn Phe Gly
    290                 295                 300 caa cag gaa tat agt aat aac caa ctt att act ccg gta gtc aac agc              960
Gln Gln Glu Tyr Ser Asn Asn Gln Leu Ile Thr Pro Val Val Asn Ser
305                 310                 315                 320 agt gat ggc acg gtt aag gta tat cgg atc acc cgc gaa tat aca acc             1008
Ser Asp Gly Thr Val Lys Val Tyr Arg Ile Thr Arg Glu Tyr Thr Thr
                325                 330                 335 aat gct tat caa atg gat gtg gag cta ttt ccc ttc ggt ggt gag aat             1056
Asn Ala Tyr Gln Met Asp Val Glu Leu Phe Pro Phe Gly Gly Glu Asn
            340                 345                 350 tat cgg tta gat tat aaa ttc aaa aat ttt tat aat gcc tct tat tta             1104
Tyr Arg Leu Asp Tyr Lys Phe Lys Asn Phe Tyr Asn Ala Ser Tyr Leu
        355                 360                 365 tcc atc aag tta aat gat aaa aga gaa ctt gtt cga act gaa ggc gct             1152
Ser Ile Lys Leu Asn Asp Lys Arg Glu Leu Val Arg Thr Glu Gly Ala
    370                 375                 380 cct caa gtc aat ata gaa tac tcc gca aat atc aca tta aat acc gct             1200
Pro Gln Val Asn Ile Glu Tyr Ser Ala Asn Ile Thr Leu Asn Thr Ala
385                 390                 395                 400 gat atc agt caa cct ttt gaa att ggc ctg aca cga gta ctt cct tcc             1248
Asp Ile Ser Gln Pro Phe Glu Ile Gly Leu Thr Arg Val Leu Pro Ser
                405                 410                 415 ggt tct tgg gca tat gcc gcc gca aaa ttt acc gtt gaa gag tat aac             1296
Gly Ser Trp Ala Tyr Ala Ala Ala Lys Phe Thr Val Glu Glu Tyr Asn
            420                 425                 430
```

-continued

| | | |
|---|---|---|
| caa tac tct ttt ctg cta aaa ctt aac aag gct att cgt cta tca cgt<br>Gln Tyr Ser Phe Leu Leu Lys Leu Asn Lys Ala Ile Arg Leu Ser Arg<br>        435                          440                    445 | 1344 |
| gcg aca gaa ttg tca ccc acg att ctg gaa ggc att gtg cgc agt gtt<br>Ala Thr Glu Leu Ser Pro Thr Ile Leu Glu Gly Ile Val Arg Ser Val<br>450                         455                         460 | 1392 |
| aat cta caa ctg gat atc aac aca gac gta tta ggt aaa gtt ttt ctg<br>Asn Leu Gln Leu Asp Ile Asn Thr Asp Val Leu Gly Lys Val Phe Leu<br>465                       470                       475                      480 | 1440 |
| act aaa tat tat atg cag cgt tat gct att cat gct gaa act gcc ctg<br>Thr Lys Tyr Tyr Met Gln Arg Tyr Ala Ile His Ala Glu Thr Ala Leu<br>                     485                       490                       495 | 1488 |
| ata cta tgc aac gcg cct att tca caa cgt tca tat gat aat caa cct<br>Ile Leu Cys Asn Ala Pro Ile Ser Gln Arg Ser Tyr Asp Asn Gln Pro<br>        500                         505                       510 | 1536 |
| agc caa ttt gat cgc ctg ttt aat acg cca tta ctg aac gga caa tat<br>Ser Gln Phe Asp Arg Leu Phe Asn Thr Pro Leu Leu Asn Gly Gln Tyr<br>                 515                       520                       525 | 1584 |
| ttt tct acc ggc gat gag gag att gat tta aat tca ggt agc acc ggc<br>Phe Ser Thr Gly Asp Glu Glu Ile Asp Leu Asn Ser Gly Ser Thr Gly<br>530                         535                         540 | 1632 |
| gat tgg cga aaa acc ata ctt aag cgt gca ttt aat att gat gat gtc<br>Asp Trp Arg Lys Thr Ile Leu Lys Arg Ala Phe Asn Ile Asp Asp Val<br>545                       550                       555                      560 | 1680 |
| tcg ctc ttc cgc ctg ctt aaa att acc gac cat gat aat aaa gat gga<br>Ser Leu Phe Arg Leu Leu Lys Ile Thr Asp His Asp Asn Lys Asp Gly<br>                 565                       570                       575 | 1728 |
| aaa att aaa aat aac cta aag aat ctt tcc aat tta tat att gga aaa<br>Lys Ile Lys Asn Asn Leu Lys Asn Leu Ser Asn Leu Tyr Ile Gly Lys<br>                     580                       585                       590 | 1776 |
| tta ctg gca gat att cat caa tta acc att gat gaa ctg gat tta tta<br>Leu Leu Ala Asp Ile His Gln Leu Thr Ile Asp Glu Leu Asp Leu Leu<br>        595                         600                       605 | 1824 |
| ctg att gcc gta ggt gaa gga aaa act aat tta tcc gct atc agt gat<br>Leu Ile Ala Val Gly Glu Gly Lys Thr Asn Leu Ser Ala Ile Ser Asp<br>610                         615                         620 | 1872 |
| aag caa ttg gct acc ctg atc aga aaa ctc aat act att acc agc tgg<br>Lys Gln Leu Ala Thr Leu Ile Arg Lys Leu Asn Thr Ile Thr Ser Trp<br>625                       630                       635                      640 | 1920 |
| cta cat aca cag aag tgg agt gta ttc cag cta ttt atc atg acc tcc<br>Leu His Thr Gln Lys Trp Ser Val Phe Gln Leu Phe Ile Met Thr Ser<br>                     645                       650                       655 | 1968 |
| acc agc tat aac aaa acg cta acg cct gaa att aag aat ttg ctg gat<br>Thr Ser Tyr Asn Lys Thr Leu Thr Pro Glu Ile Lys Asn Leu Leu Asp<br>        660                         665                       670 | 2016 |
| acc gtc tac cac ggt tta caa ggt ttt gat aaa gac aaa gca gat ttg<br>Thr Val Tyr His Gly Leu Gln Gly Phe Asp Lys Asp Lys Ala Asp Leu<br>                 675                       680                       685 | 2064 |
| cta cat gtc atg gcg ccc tat att gcg gcc acc ttg caa tta tca tcg<br>Leu His Val Met Ala Pro Tyr Ile Ala Ala Thr Leu Gln Leu Ser Ser<br>690                         695                         700 | 2112 |
| gaa aat gtc gcc cac tcg gta ctc ctt tgg gca gat aag tta cag ccc<br>Glu Asn Val Ala His Ser Val Leu Leu Trp Ala Asp Lys Leu Gln Pro<br>705                       710                       715                      720 | 2160 |
| ggc gac ggc gca atg aca gca gaa aaa ttc tgg gac tgg ttg aat act<br>Gly Asp Gly Ala Met Thr Ala Glu Lys Phe Trp Asp Trp Leu Asn Thr<br>                     725                       730                       735 | 2208 |
| aag tat acg ccg ggt tca tcg gaa gcc gta gaa acg cag gaa cat atc<br>Lys Tyr Thr Pro Gly Ser Ser Glu Ala Val Glu Thr Gln Glu His Ile<br>740                         745                         750 | 2256 |

-continued

| | |
|---|---|
| gtt cag tat tgt cag gct ctg gca caa ttg gaa atg gtt tac cat tcc<br>Val Gln Tyr Cys Gln Ala Leu Ala Gln Leu Glu Met Val Tyr His Ser<br>           755                       760                        765 | 2304 |
| acc ggc atc aac gaa aac gcc ttc cgt cta ttt gtg aca aaa cca gag<br>Thr Gly Ile Asn Glu Asn Ala Phe Arg Leu Phe Val Thr Lys Pro Glu<br>770                        775                      780 | 2352 |
| atg ttt ggc gct gca act gga gca gcg ccc gcg cat gat gcc ctt tca<br>Met Phe Gly Ala Ala Thr Gly Ala Ala Pro Ala His Asp Ala Leu Ser<br>785                       790                      795                      800 | 2400 |
| ctg att atg ctg aca cgt ttt gcg gat tgg gtg aac gca cta ggc gaa<br>Leu Ile Met Leu Thr Arg Phe Ala Asp Trp Val Asn Ala Leu Gly Glu<br>           805                       810                      815 | 2448 |
| aaa gcg tcc tcg gtg cta gcg gca ttt gaa gct aac tcg tta acg gca<br>Lys Ala Ser Ser Val Leu Ala Ala Phe Glu Ala Asn Ser Leu Thr Ala<br>820                       825                      830 | 2496 |
| gaa caa ctg gct gat gcc atg aat ctt gat gct aat ttg ctg ttg caa<br>Glu Gln Leu Ala Asp Ala Met Asn Leu Asp Ala Asn Leu Leu Leu Gln<br>           835                       840                      845 | 2544 |
| gcc agt att caa gca caa aat cat caa cat ctt ccc cca gta act cca<br>Ala Ser Ile Gln Ala Gln Asn His Gln His Leu Pro Pro Val Thr Pro<br>850                       855                      860 | 2592 |
| gaa aat gcg ttc tcc tgt tgg aca tct atc aat act atc ctg caa tgg<br>Glu Asn Ala Phe Ser Cys Trp Thr Ser Ile Asn Thr Ile Leu Gln Trp<br>865                       870                      875                      880 | 2640 |
| gtt aat gtc gca caa caa ttg aat gtc gcc cca cag ggc gtt tcc gct<br>Val Asn Val Ala Gln Gln Leu Asn Val Ala Pro Gln Gly Val Ser Ala<br>                     885                        890                      895 | 2688 |
| ttg gtc ggg ctg gat tat att caa tca atg aaa gag aca ccg acc tat<br>Leu Val Gly Leu Asp Tyr Ile Gln Ser Met Lys Glu Thr Pro Thr Tyr<br>900                       905                      910 | 2736 |
| gcc cag tgg gaa aac gcg gca ggc gta tta acc gcc ggg ttg aat tca<br>Ala Gln Trp Glu Asn Ala Ala Gly Val Leu Thr Ala Gly Leu Asn Ser<br>           915                       920                      925 | 2784 |
| caa cag gct aat aca tta cac gct ttt ctg gat gaa tct cgc agt gcc<br>Gln Gln Ala Asn Thr Leu His Ala Phe Leu Asp Glu Ser Arg Ser Ala<br>930                       935                      940 | 2832 |
| gca tta agc acc tac tat atc cgt caa gtc gcc aag gca gcg gcg gct<br>Ala Leu Ser Thr Tyr Tyr Ile Arg Gln Val Ala Lys Ala Ala Ala Ala<br>945                       950                      955                      960 | 2880 |
| att aaa agc cgt gat gac ttg tat caa tac tta ctg att gat aat cag<br>Ile Lys Ser Arg Asp Asp Leu Tyr Gln Tyr Leu Leu Ile Asp Asn Gln<br>                     965                        970                      975 | 2928 |
| gtt tct gcg gca ata aaa acc acc cgg atc gcc gaa gcc att gcc agt<br>Val Ser Ala Ala Ile Lys Thr Thr Arg Ile Ala Glu Ala Ile Ala Ser<br>980                       985                      990 | 2976 |
| att caa ctg tac gtc aac cgg gca ttg gaa aat gtg gaa gaa aat gcc<br>Ile Gln Leu Tyr Val Asn Arg Ala Leu Glu Asn Val Glu Glu Asn Ala<br>           995                      1000                    1005 | 3024 |
| aat tcg ggg gtt atc agc cgc caa ttc ttt atc gac tgg gac aaa tac<br>Asn Ser Gly Val Ile Ser Arg Gln Phe Phe Ile Asp Trp Asp Lys Tyr<br>1010                      1015                    1020 | 3072 |
| aat aaa cgc tac agc act tgg gcg ggt gtt tct caa tta gtt tac tac<br>Asn Lys Arg Tyr Ser Thr Trp Ala Gly Val Ser Gln Leu Val Tyr Tyr<br>1025                      1030                    1035                    1040 | 3120 |
| ccg gaa aac tat att gat ccg acc atg cgt atc gga caa acc aaa atg<br>Pro Glu Asn Tyr Ile Asp Pro Thr Met Arg Ile Gly Gln Thr Lys Met<br>                      1045                    1050                    1055 | 3168 |
| atg gac gca tta ctg caa tcc gtc agc caa agc caa tta aac gcc gat<br>Met Asp Ala Leu Leu Gln Ser Val Ser Gln Ser Gln Leu Asn Ala Asp | 3216 |

-continued

| | | | |
|---|---|---|---|
| | 1060 | 1065 | 1070 | acc gtc gaa gat gcc ttt atg tct tat ctg aca tcg ttt gaa caa gtg    3264
Thr Val Glu Asp Ala Phe Met Ser Tyr Leu Thr Ser Phe Glu Gln Val
        1075                1080                1085 gct aat ctt aaa gtt att agc gca tat cac gat aat att aat aac gat    3312
Ala Asn Leu Lys Val Ile Ser Ala Tyr His Asp Asn Ile Asn Asn Asp
        1090                1095                1100 caa ggg ctg acc tat ttt atc gga ctc agt gaa act gat gcc ggt gaa    3360
Gln Gly Leu Thr Tyr Phe Ile Gly Leu Ser Glu Thr Asp Ala Gly Glu
1105                1110                1115                1120 tat tat tgg cgc agt gtc gat cac agt aaa ttc aac gac ggt aaa ttc    3408
Tyr Tyr Trp Arg Ser Val Asp His Ser Lys Phe Asn Asp Gly Lys Phe
                1125                1130                1135 gcg gct aat gcc tgg agt gaa tgg cat aaa att gat tgt cca att aac    3456
Ala Ala Asn Ala Trp Ser Glu Trp His Lys Ile Asp Cys Pro Ile Asn
        1140                1145                1150 cct tat aaa agc act atc cgt cca gtg ata tat aaa tcc cgc ctg tat    3504
Pro Tyr Lys Ser Thr Ile Arg Pro Val Ile Tyr Lys Ser Arg Leu Tyr
        1155                1160                1165 ctg ctc tgg ttg gaa caa aag gag atc acc aaa cag aca gga aat agt    3552
Leu Leu Trp Leu Glu Gln Lys Glu Ile Thr Lys Gln Thr Gly Asn Ser
        1170                1175                1180 aaa gat ggc tat caa act gaa acg gat tat cgt tat gaa cta aaa ttg    3600
Lys Asp Gly Tyr Gln Thr Glu Thr Asp Tyr Arg Tyr Glu Leu Lys Leu
1185                1190                1195                1200 gcg cat atc cgc tat gat ggc act tgg aat acg cca atc acc ttt gat    3648
Ala His Ile Arg Tyr Asp Gly Thr Trp Asn Thr Pro Ile Thr Phe Asp
                1205                1210                1215 gtc aat aaa aaa ata tcc gag cta aaa ctg gaa aaa aat aga gcg ccc    3696
Val Asn Lys Lys Ile Ser Glu Leu Lys Leu Glu Lys Asn Arg Ala Pro
        1220                1225                1230 gga ctc tat tgt gcc ggt tat caa ggt gaa gat acg ttg ctg gtg atg    3744
Gly Leu Tyr Cys Ala Gly Tyr Gln Gly Glu Asp Thr Leu Leu Val Met
        1235                1240                1245 ttt tat aac caa caa gac aca cta gat agt tat aaa aac gct tca atg    3792
Phe Tyr Asn Gln Gln Asp Thr Leu Asp Ser Tyr Lys Asn Ala Ser Met
        1250                1255                1260 caa gga cta tat atc ttt gct gat atg gca tcc aaa gat atg acc cca    3840
Gln Gly Leu Tyr Ile Phe Ala Asp Met Ala Ser Lys Asp Met Thr Pro
1265                1270                1275                1280 gaa cag agc aat gtt tat cgg gat aat agc tat caa caa ttt gat acc    3888
Glu Gln Ser Asn Val Tyr Arg Asp Asn Ser Tyr Gln Gln Phe Asp Thr
                1285                1290                1295 aat aat gtc aga aga gtg aat aac cgc tat gca gag gat tat gag att    3936
Asn Asn Val Arg Arg Val Asn Asn Arg Tyr Ala Glu Asp Tyr Glu Ile
        1300                1305                1310 cct tcc tcg gta agt agc cgt aaa gac tat ggt tgg gga gat tat tac    3984
Pro Ser Ser Val Ser Ser Arg Lys Asp Tyr Gly Trp Gly Asp Tyr Tyr
        1315                1320                1325 ctc agc atg gta tat aac gga gat att cca act atc aat tac aaa gcc    4032
Leu Ser Met Val Tyr Asn Gly Asp Ile Pro Thr Ile Asn Tyr Lys Ala
        1330                1335                1340 gca tca agt gat tta aaa atc tat atc tca cca aaa tta aga att att    4080
Ala Ser Ser Asp Leu Lys Ile Tyr Ile Ser Pro Lys Leu Arg Ile Ile
1345                1350                1355                1360 cat aat gga tat gaa gga cag aag cgc aat caa tgc aat ctg atg aat    4128
His Asn Gly Tyr Glu Gly Gln Lys Arg Asn Gln Cys Asn Leu Met Asn
                1365                1370                1375 aaa tat ggc aaa cta ggt gat aaa ttt att gtt tat act agc ttg ggg    4176

-continued

| | | | | | | | | | | | | | | |
|---|---|---|---|---|---|---|---|---|---|---|---|---|---|---|
| Lys | Tyr | Gly | Lys | Leu | Gly | Asp | Lys | Phe | Ile | Val | Tyr | Thr | Ser | Leu | Gly |
| | | 1380 | | | | 1385 | | | | 1390 | | | | | |

```
gtc aat cca aat aac tcg tca aat aag ctc atg ttt tac ccc gtc tat      4224
Val Asn Pro Asn Asn Ser Ser Asn Lys Leu Met Phe Tyr Pro Val Tyr
    1395                1400                1405 caa tat agc gga aac acc agt gga ctc aat caa ggg aga cta cta ttc      4272
Gln Tyr Ser Gly Asn Thr Ser Gly Leu Asn Gln Gly Arg Leu Leu Phe
    1410                1415                1420 cac cgt gac acc act tat cca tct aaa gta gaa gct tgg att cct gga      4320
His Arg Asp Thr Thr Tyr Pro Ser Lys Val Glu Ala Trp Ile Pro Gly
1425                1430                1435                1440 gca aaa cgt tct cta acc aac caa aat gcc gcc att ggt gat gat tat      4368
Ala Lys Arg Ser Leu Thr Asn Gln Asn Ala Ala Ile Gly Asp Asp Tyr
                1445                1450                1455 gct aca gac tct ctg aat aaa ccg gat gat ctt aag caa tat atc ttt      4416
Ala Thr Asp Ser Leu Asn Lys Pro Asp Asp Leu Lys Gln Tyr Ile Phe
        1460                1465                1470 atg act gac agt aaa ggg act gct act gat gtc tca ggc cca gta gag      4464
Met Thr Asp Ser Lys Gly Thr Ala Thr Asp Val Ser Gly Pro Val Glu
            1475                1480                1485 att aat act gca att tct cca gca aaa gtt cag ata ata gtc aaa gcg      4512
Ile Asn Thr Ala Ile Ser Pro Ala Lys Val Gln Ile Ile Val Lys Ala
    1490                1495                1500 ggt ggc aag gag caa act ttt acc gca gat aaa gat gtc tcc att cag      4560
Gly Gly Lys Glu Gln Thr Phe Thr Ala Asp Lys Asp Val Ser Ile Gln
1505                1510                1515                1520 cca tca cct agc ttt gat gaa atg aat tat caa ttt aat gcc ctt gaa      4608
Pro Ser Pro Ser Phe Asp Glu Met Asn Tyr Gln Phe Asn Ala Leu Glu
                1525                1530                1535 ata gac ggt tct ggt ctg aat ttt att aac aac tca gcc agt att gat      4656
Ile Asp Gly Ser Gly Leu Asn Phe Ile Asn Asn Ser Ala Ser Ile Asp
        1540                1545                1550 gtt act ttt acc gca ttt gcg gag gat ggc cgc aaa ctg ggt tat gaa      4704
Val Thr Phe Thr Ala Phe Ala Glu Asp Gly Arg Lys Leu Gly Tyr Glu
            1555                1560                1565 agt ttc agt att cct gtt acc ctc aag gta agt acc gat aat gcc ctg      4752
Ser Phe Ser Ile Pro Val Thr Leu Lys Val Ser Thr Asp Asn Ala Leu
    1570                1575                1580 acc ctg cac cat aat gaa aat ggt gcg caa tat atg caa tgg caa tcc      4800
Thr Leu His His Asn Glu Asn Gly Ala Gln Tyr Met Gln Trp Gln Ser
1585                1590                1595                1600 tat cgt acc cgc ctg aat act cta ttt gcc cgc cag ttg gtt gca cgc      4848
Tyr Arg Thr Arg Leu Asn Thr Leu Phe Ala Arg Gln Leu Val Ala Arg
                1605                1610                1615 gcc acc acc gga atc gat aca att ctg agt atg gaa act cag aat att      4896
Ala Thr Thr Gly Ile Asp Thr Ile Leu Ser Met Glu Thr Gln Asn Ile
        1620                1625                1630 cag gaa ccg cag tta ggc aaa ggt ttc tat gct acg ttc gtg ata cct      4944
Gln Glu Pro Gln Leu Gly Lys Gly Phe Tyr Ala Thr Phe Val Ile Pro
            1635                1640                1645 ccc tat aac cta tca act cat ggt gat gaa cgt tgg ttt aag ctt tat      4992
Pro Tyr Asn Leu Ser Thr His Gly Asp Glu Arg Trp Phe Lys Leu Tyr
    1650                1655                1660 atc aaa cat gtt gtt gat aat aat tca cat att atc tat tca ggc cag      5040
Ile Lys His Val Val Asp Asn Asn Ser His Ile Ile Tyr Ser Gly Gln
1665                1670                1675                1680 cta aca gat aca aat ata aac atc aca tta ttt att cct ctt gat gat      5088
Leu Thr Asp Thr Asn Ile Asn Ile Thr Leu Phe Ile Pro Leu Asp Asp
                1685                1690                1695
```

-continued

| | |
|---|---|
| gtc cca ttg aat caa gat tat cac gcc aag gtt tat atg acc ttc aag<br>Val Pro Leu Asn Gln Asp Tyr His Ala Lys Val Tyr Met Thr Phe Lys<br>        1700                    1705                    1710 | 5136 |
| aaa tca cca tca gat ggt acc tgg tgg ggc cct cac ttt gtt aga gat<br>Lys Ser Pro Ser Asp Gly Thr Trp Trp Gly Pro His Phe Val Arg Asp<br>1715                    1720                    1725 | 5184 |
| gat aaa gga ata gta aca ata aac cct aaa tcc att ttg acc cat ttt<br>Asp Lys Gly Ile Val Thr Ile Asn Pro Lys Ser Ile Leu Thr His Phe<br>        1730                    1735                    1740 | 5232 |
| gag agc gtc aat gtc ctg aat aat att agt agc gaa cca atg gat ttc<br>Glu Ser Val Asn Val Leu Asn Asn Ile Ser Ser Glu Pro Met Asp Phe<br>1745                    1750                    1755                    1760 | 5280 |
| agc ggc gct aac agc ctc tat ttc tgg gaa ctg ttc tac tat acc ccg<br>Ser Gly Ala Asn Ser Leu Tyr Phe Trp Glu Leu Phe Tyr Tyr Thr Pro<br>                1765                    1770                    1775 | 5328 |
| atg ctg gtt gct caa cgt ttg ctg cat gaa cag aac ttc gat gaa gcc<br>Met Leu Val Ala Gln Arg Leu Leu His Glu Gln Asn Phe Asp Glu Ala<br>        1780                    1785                    1790 | 5376 |
| aac cgt tgg ctg aaa tat gtc tgg agt cca tcc ggt tat att gtc cac<br>Asn Arg Trp Leu Lys Tyr Val Trp Ser Pro Ser Gly Tyr Ile Val His<br>1795                    1800                    1805 | 5424 |
| ggc cag att cag aac tac cag tgg aac gtc cgc ccg tta ctg gaa gac<br>Gly Gln Ile Gln Asn Tyr Gln Trp Asn Val Arg Pro Leu Leu Glu Asp<br>        1810                    1815                    1820 | 5472 |
| acc agt tgg aac agt gat cct ttg gat tcc gtc gat cct gac gcg gta<br>Thr Ser Trp Asn Ser Asp Pro Leu Asp Ser Val Asp Pro Asp Ala Val<br>1825                    1830                    1835                    1840 | 5520 |
| gca cag cac gat cca atg cac tac aaa gtt tca act ttt atg cgt acc<br>Ala Gln His Asp Pro Met His Tyr Lys Val Ser Thr Phe Met Arg Thr<br>                1845                    1850                    1855 | 5568 |
| ttg gat cta ttg ata gca cgc ggc gac cat gct tat cgc caa ctg gaa<br>Leu Asp Leu Leu Ile Ala Arg Gly Asp His Ala Tyr Arg Gln Leu Glu<br>        1860                    1865                    1870 | 5616 |
| cga gat aca ctc aac gaa gcg aag atg tgg tat atg caa gcg ctg cat<br>Arg Asp Thr Leu Asn Glu Ala Lys Met Trp Tyr Met Gln Ala Leu His<br>1875                    1880                    1885 | 5664 |
| cta tta ggt gac aaa cct tat cta ccg ctg agt acg aca tgg agt gat<br>Leu Leu Gly Asp Lys Pro Tyr Leu Pro Leu Ser Thr Thr Trp Ser Asp<br>        1890                    1895                    1900 | 5712 |
| cca cga cta gac aga gcc gcg gat atc act acc caa aat gct cac gac<br>Pro Arg Leu Asp Arg Ala Ala Asp Ile Thr Thr Gln Asn Ala His Asp<br>1905                    1910                    1915                    1920 | 5760 |
| agc gca ata gtc gct ctg cgg cag aat ata cct aca ccg gca cct tta<br>Ser Ala Ile Val Ala Leu Arg Gln Asn Ile Pro Thr Pro Ala Pro Leu<br>                1925                    1930                    1935 | 5808 |
| tca ttg cgc agc gct aat acc ctg act gat ctc ttc ctg ccg caa atc<br>Ser Leu Arg Ser Ala Asn Thr Leu Thr Asp Leu Phe Leu Pro Gln Ile<br>        1940                    1945                    1950 | 5856 |
| aat gaa gtg atg atg aat tac tgg cag aca tta gct cag aga gta tac<br>Asn Glu Val Met Met Asn Tyr Trp Gln Thr Leu Ala Gln Arg Val Tyr<br>1955                    1960                    1965 | 5904 |
| aat ctg cgt cat aac ctc tct atc gac ggc cag ccg tta tat ctg cca<br>Asn Leu Arg His Asn Leu Ser Ile Asp Gly Gln Pro Leu Tyr Leu Pro<br>        1970                    1975                    1980 | 5952 |
| atc tat gcc aca ccg gcc gat ccg aaa gcg tta ctc agc gcc gcc gtt<br>Ile Tyr Ala Thr Pro Ala Asp Pro Lys Ala Leu Leu Ser Ala Ala Val<br>1985                    1990                    1995                    2000 | 6000 |
| gcc act tct caa ggt gga ggc aag cta ccg gaa tca ttt atg tcc ctg<br>Ala Thr Ser Gln Gly Gly Gly Lys Leu Pro Glu Ser Phe Met Ser Leu<br>                2005                    2010                    2015 | 6048 |

-continued

```
tgg cgt ttc ccg cac atg ctg gaa aat gcg cgc ggc atg gtt agc cag        6096
Trp Arg Phe Pro His Met Leu Glu Asn Ala Arg Gly Met Val Ser Gln
            2020                2025                2030 ctc acc cag ttc ggc tcc acg tta caa aat att atc gaa cgt cag gac        6144
Leu Thr Gln Phe Gly Ser Thr Leu Gln Asn Ile Ile Glu Arg Gln Asp
                2035                2040                2045 gcg gaa gcg ctc aat gcg tta tta caa aat cag gcc gcc gag ctg ata        6192
Ala Glu Ala Leu Asn Ala Leu Leu Gln Asn Gln Ala Ala Glu Leu Ile
    2050                2055                2060 ttg act aac ctg agc att cag gac aaa acc att gaa gaa ttg gat gcc        6240
Leu Thr Asn Leu Ser Ile Gln Asp Lys Thr Ile Glu Glu Leu Asp Ala
2065                2070                2075                2080 gag aaa acg gtg ttg gaa aaa tcc aaa gcg gga gca caa tcg cgc ttt        6288
Glu Lys Thr Val Leu Glu Lys Ser Lys Ala Gly Ala Gln Ser Arg Phe
                2085                2090                2095 gat agc tac ggc aaa ctg tac gat gag aat atc aac gcc ggt gaa aac        6336
Asp Ser Tyr Gly Lys Leu Tyr Asp Glu Asn Ile Asn Ala Gly Glu Asn
            2100                2105                2110 caa gcc atg acg cta cga gcg tcc gcc gcc ggg ctt acc acg gca gtt        6384
Gln Ala Met Thr Leu Arg Ala Ser Ala Ala Gly Leu Thr Thr Ala Val
        2115                2120                2125 cag gca tcc cgt ctg gcc ggt gcg gcg gct gat ctg gtg cct aac atc        6432
Gln Ala Ser Arg Leu Ala Gly Ala Ala Ala Asp Leu Val Pro Asn Ile
    2130                2135                2140 ttc ggc ttt gcc ggt ggc ggc agc cgt tgg ggg gct atc gct gag gcg        6480
Phe Gly Phe Ala Gly Gly Gly Ser Arg Trp Gly Ala Ile Ala Glu Ala
2145                2150                2155                2160 aca ggt tat gtg atg gaa ttc tcc gcg aat gtt atg aac acc gaa gcg        6528
Thr Gly Tyr Val Met Glu Phe Ser Ala Asn Val Met Asn Thr Glu Ala
                2165                2170                2175 gat aaa att agc caa tct gaa acc tac cgt cgt cgc cgt cag gag tgg        6576
Asp Lys Ile Ser Gln Ser Glu Thr Tyr Arg Arg Arg Arg Gln Glu Trp
            2180                2185                2190 gag atc cag cgg aat aat gcc gaa gcg gaa ttg aag caa atc gat gct        6624
Glu Ile Gln Arg Asn Asn Ala Glu Ala Glu Leu Lys Gln Ile Asp Ala
        2195                2200                2205 cag ctc aaa tca ctc gct gta cgc cgc gaa gcc gcc gta ttg cag aaa        6672
Gln Leu Lys Ser Leu Ala Val Arg Arg Glu Ala Ala Val Leu Gln Lys
    2210                2215                2220 acc agt ctg aaa acc caa caa gaa cag acc caa tct caa ttg gcc ttc        6720
Thr Ser Leu Lys Thr Gln Gln Glu Gln Thr Gln Ser Gln Leu Ala Phe
2225                2230                2235                2240 ctg caa cgt aag ttc agc aat cag gcg tta tac aac tgg ctg cgt ggt        6768
Leu Gln Arg Lys Phe Ser Asn Gln Ala Leu Tyr Asn Trp Leu Arg Gly
                2245                2250                2255 cga ctg gcg gcg att tac ttc cag ttc tac gat ttg gcc gtc gcg cgt        6816
Arg Leu Ala Ala Ile Tyr Phe Gln Phe Tyr Asp Leu Ala Val Ala Arg
            2260                2265                2270 tgc ctg atg gca gaa caa gct tac cgt tgg gaa ctc aat gat gac tct        6864
Cys Leu Met Ala Glu Gln Ala Tyr Arg Trp Glu Leu Asn Asp Asp Ser
        2275                2280                2285 gcc cgc ttc att aaa ccg ggc gcc tgg cag gga acc tat gcc ggt ctg        6912
Ala Arg Phe Ile Lys Pro Gly Ala Trp Gln Gly Thr Tyr Ala Gly Leu
    2290                2295                2300 ctt gca ggt gaa acc ttg atg ctg agt ctg gca caa atg gaa gac gct        6960
Leu Ala Gly Glu Thr Leu Met Leu Ser Leu Ala Gln Met Glu Asp Ala
2305                2310                2315                2320 cat ctg aaa cgc gat aaa cgc gca tta gag gtt gaa cgc aca gta tcg        7008
His Leu Lys Arg Asp Lys Arg Ala Leu Glu Val Glu Arg Thr Val Ser
                2325                2330                2335
```

```
ctg gcc gaa gtt tat gca gga tta cca aaa gat aac ggt cca ttt tcc        7056
Leu Ala Glu Val Tyr Ala Gly Leu Pro Lys Asp Asn Gly Pro Phe Ser
            2340                2345                2350 ctg gct cag gaa att gac aag ctg gtg agt caa ggt tca ggc agt gcc        7104
Leu Ala Gln Glu Ile Asp Lys Leu Val Ser Gln Gly Ser Gly Ser Ala
            2355                2360                2365 ggc agt ggt aat aat aat ttg gcg ttc ggc gcc ggc acg gac act aaa        7152
Gly Ser Gly Asn Asn Asn Leu Ala Phe Gly Ala Gly Thr Asp Thr Lys
            2370                2375                2380 acc tct ttg cag gca tca gtt tca ttc gct gat ttg aaa att cgt gaa        7200
Thr Ser Leu Gln Ala Ser Val Ser Phe Ala Asp Leu Lys Ile Arg Glu
2385                2390                2395                2400 gat tac ccg gca tcg ctt ggc aaa att cga cgt atc aaa cag atc agc        7248
Asp Tyr Pro Ala Ser Leu Gly Lys Ile Arg Arg Ile Lys Gln Ile Ser
            2405                2410                2415 gtc act ttg ccc gcg cta ctg gga ccg tat cag gat gta cag gca ata        7296
Val Thr Leu Pro Ala Leu Leu Gly Pro Tyr Gln Asp Val Gln Ala Ile
            2420                2425                2430 ttg tct tac ggc gat aaa gcc gga tta gct aac ggc tgt gaa gcg ctg        7344
Leu Ser Tyr Gly Asp Lys Ala Gly Leu Ala Asn Gly Cys Glu Ala Leu
            2435                2440                2445 gca gtt tct cac ggt atg aat gac agc ggc caa ttc cag ctc gat ttc        7392
Ala Val Ser His Gly Met Asn Asp Ser Gly Gln Phe Gln Leu Asp Phe
            2450                2455                2460 aac gat ggc aaa ttc ctg cca ttc gaa ggc atc gcc att gat caa ggc        7440
Asn Asp Gly Lys Phe Leu Pro Phe Glu Gly Ile Ala Ile Asp Gln Gly
2465                2470                2475                2480 acg ctg aca ctg agc ttc cca aat gca tct atg ccg gag aaa ggt aaa        7488
Thr Leu Thr Leu Ser Phe Pro Asn Ala Ser Met Pro Glu Lys Gly Lys
            2485                2490                2495 caa gcc act atg tta aaa acc ctg aac gat atc att ttg cat att cgc        7536
Gln Ala Thr Met Leu Lys Thr Leu Asn Asp Ile Ile Leu His Ile Arg
            2500                2505                2510 tac acc att aaa taa                                                     7551
Tyr Thr Ile Lys
        2515

<210> SEQ ID NO 2
<211> LENGTH: 7515
<212> TYPE: DNA
<213> ORGANISM: Photorhabdus luminescens
<220> FEATURE:
<221> NAME/KEY: CDS
<222> LOCATION: (1)..(7512)

<400> SEQUENCE: 2 atg caa aac tca tta tca agc act atc gat act att tgt cag aaa ctg         48
Met Gln Asn Ser Leu Ser Ser Thr Ile Asp Thr Ile Cys Gln Lys Leu
  1               5                  10                  15 caa tta act tgt ccg gcg gaa att gct ttg tat ccc ttt gat act ttc         96
Gln Leu Thr Cys Pro Ala Glu Ile Ala Leu Tyr Pro Phe Asp Thr Phe
             20                  25                  30 cgg gaa aaa act cgg gga atg gtt aat tgg ggg gaa gca aaa cgg att        144
Arg Glu Lys Thr Arg Gly Met Val Asn Trp Gly Glu Ala Lys Arg Ile
         35                  40                  45 tat gaa att gca caa gcg gaa cag gat aga aac cta ctt cat gaa aaa        192
Tyr Glu Ile Ala Gln Ala Glu Gln Asp Arg Asn Leu Leu His Glu Lys
     50                  55                  60 cgt att ttt gcc tat gct aat ccg ctg ctg aaa aac gct gtt cgg ttg        240
Arg Ile Phe Ala Tyr Ala Asn Pro Leu Leu Lys Asn Ala Val Arg Leu
 65                  70                  75                  80
```

```
ggt acc cgg caa atg ttg ggt ttt ata caa ggt tat agt gat ctg ttt      288
Gly Thr Arg Gln Met Leu Gly Phe Ile Gln Gly Tyr Ser Asp Leu Phe
             85                  90                  95 ggt aat cgt gct gat aac tat gcc gcg ccg ggc tcg gtt gca tcg atg      336
Gly Asn Arg Ala Asp Asn Tyr Ala Ala Pro Gly Ser Val Ala Ser Met
            100                 105                 110 ttc tca ccg gcg gct tat ttg acg gaa ttg tac cgt gaa gcc aaa aac      384
Phe Ser Pro Ala Ala Tyr Leu Thr Glu Leu Tyr Arg Glu Ala Lys Asn
        115                 120                 125 ttg cat gac agc agc tca att tat tac cta gat aaa cgt cgc ccg gat      432
Leu His Asp Ser Ser Ser Ile Tyr Tyr Leu Asp Lys Arg Arg Pro Asp
    130                 135                 140 tta gca agc tta atg ctc agc cag aaa aat atg gat gag gaa att tca      480
Leu Ala Ser Leu Met Leu Ser Gln Lys Asn Met Asp Glu Glu Ile Ser
145                 150                 155                 160 acg ctg gct ctc tct aat gaa ttg tgc ctt gcc ggg atc gaa aca aaa      528
Thr Leu Ala Leu Ser Asn Glu Leu Cys Leu Ala Gly Ile Glu Thr Lys
                165                 170                 175 aca gga aaa tca caa gat gaa gtg atg gat atg ttg tca act tat cgt      576
Thr Gly Lys Ser Gln Asp Glu Val Met Asp Met Leu Ser Thr Tyr Arg
            180                 185                 190 tta agt gga gag aca cct tat cat cac gct tat gaa act gtt cgt gaa      624
Leu Ser Gly Glu Thr Pro Tyr His His Ala Tyr Glu Thr Val Arg Glu
        195                 200                 205 atc gtt cat gaa cgt gat cca gga ttt cgt cat ttg tca cag gca ccc      672
Ile Val His Glu Arg Asp Pro Gly Phe Arg His Leu Ser Gln Ala Pro
    210                 215                 220 att gtt gct gct aag ctc gat cct gtg act ttg ttg ggt att agc tcc      720
Ile Val Ala Ala Lys Leu Asp Pro Val Thr Leu Leu Gly Ile Ser Ser
225                 230                 235                 240 cat att tcg cca gaa ctg tat aac ttg ctg att gag gag atc ccg gaa      768
His Ile Ser Pro Glu Leu Tyr Asn Leu Leu Ile Glu Glu Ile Pro Glu
                245                 250                 255 aaa gat gaa gcc gcg ctt gat acg ctt tat aaa aca aac ttt ggc gat      816
Lys Asp Glu Ala Ala Leu Asp Thr Leu Tyr Lys Thr Asn Phe Gly Asp
            260                 265                 270 att act act gct cag tta atg tcc cca agt tat ctg gcc cgg tat tat      864
Ile Thr Thr Ala Gln Leu Met Ser Pro Ser Tyr Leu Ala Arg Tyr Tyr
        275                 280                 285 ggc gtc tca ccg gaa gat att gcc tac gtg acg act tca tta tca cat      912
Gly Val Ser Pro Glu Asp Ile Ala Tyr Val Thr Thr Ser Leu Ser His
    290                 295                 300 gtt gga tat agc agt gat att ctg gtt att ccg ttg gtc gat ggt gtg      960
Val Gly Tyr Ser Ser Asp Ile Leu Val Ile Pro Leu Val Asp Gly Val
305                 310                 315                 320 ggt aag atg gaa gta gtt cgt gtt acc cga aca cca tcg gat aat tat     1008
Gly Lys Met Glu Val Val Arg Val Thr Arg Thr Pro Ser Asp Asn Tyr
                325                 330                 335 acc agt cag acg aat tat att gag ctg tat cca cag ggt ggc gac aat     1056
Thr Ser Gln Thr Asn Tyr Ile Glu Leu Tyr Pro Gln Gly Gly Asp Asn
            340                 345                 350 tat ttg atc aaa tac aat cta agc aat agt ttt ggt ttg gat gat ttt     1104
Tyr Leu Ile Lys Tyr Asn Leu Ser Asn Ser Phe Gly Leu Asp Asp Phe
        355                 360                 365 tat ctg caa tat aaa gat ggt tcc gct gat tgg act gag att gcc cat     1152
Tyr Leu Gln Tyr Lys Asp Gly Ser Ala Asp Trp Thr Glu Ile Ala His
    370                 375                 380 aat ccc tat cct gat atg gtc ata aat caa aag tat gaa tca cag gcg     1200
Asn Pro Tyr Pro Asp Met Val Ile Asn Gln Lys Tyr Glu Ser Gln Ala
```

-continued

| | | | | | | | | | | | | | | | | |
|---|---|---|---|---|---|---|---|---|---|---|---|---|---|---|---|---|
|385| | | | |390| | | | |395| | | | |400| |
|aca|atc|aaa|cgt|agt|gac|tct|gac|aat|ata|ctc|agt|ata|ggg|tta|caa|1248|
|Thr|Ile|Lys|Arg|Ser|Asp|Ser|Asp|Asn|Ile|Leu|Ser|Ile|Gly|Leu|Gln| |
| | | | |405| | | | |410| | | | |415| | |
|aga|tgg|cat|agc|ggt|agt|tat|aat|ttt|gcc|gcc|gcc|aat|ttt|aaa|att|1296|
|Arg|Trp|His|Ser|Gly|Ser|Tyr|Asn|Phe|Ala|Ala|Ala|Asn|Phe|Lys|Ile| |
| | | |420| | | | |425| | | | |430| | | |
|gac|caa|tac|tcc|ccg|aaa|gct|ttc|ctg|ctt|aaa|atg|aat|aag|gct|att|1344|
|Asp|Gln|Tyr|Ser|Pro|Lys|Ala|Phe|Leu|Leu|Lys|Met|Asn|Lys|Ala|Ile| |
| | |435| | | | |440| | | | |445| | | | |
|cgg|ttg|ctc|aaa|gct|acc|ggc|ctc|tct|ttt|gct|acg|ttg|gag|cgt|att|1392|
|Arg|Leu|Leu|Lys|Ala|Thr|Gly|Leu|Ser|Phe|Ala|Thr|Leu|Glu|Arg|Ile| |
| | |450| | | | |455| | | | |460| | | | |
|gtt|gat|agt|gtt|aat|agc|acc|aaa|tcc|atc|acg|gtt|gag|gta|tta|aac|1440|
|Val|Asp|Ser|Val|Asn|Ser|Thr|Lys|Ser|Ile|Thr|Val|Glu|Val|Leu|Asn| |
|465| | | | |470| | | | |475| | | | |480| | |
|aag|gtt|tat|cgg|gta|aaa|ttc|tat|att|gat|cgt|tat|ggc|atc|agt|gaa|1488|
|Lys|Val|Tyr|Arg|Val|Lys|Phe|Tyr|Ile|Asp|Arg|Tyr|Gly|Ile|Ser|Glu| |
| | | | |485| | | | |490| | | | |495| | | |
|gag|aca|gcc|gct|att|ttg|gct|aat|att|aat|atc|tct|cag|caa|gct|gtt|1536|
|Glu|Thr|Ala|Ala|Ile|Leu|Ala|Asn|Ile|Asn|Ile|Ser|Gln|Gln|Ala|Val| |
| | | |500| | | | |505| | | | |510| | | | |
|ggc|aat|cag|ctt|agc|cag|ttt|gag|caa|cta|ttt|aat|cac|ccg|ccg|ctc|1584|
|Gly|Asn|Gln|Leu|Ser|Gln|Phe|Glu|Gln|Leu|Phe|Asn|His|Pro|Pro|Leu| |
| | |515| | | | |520| | | | |525| | | | |
|aat|ggt|att|cgc|tat|gaa|atc|agt|gag|gac|aac|tcc|aaa|cat|ctt|cct|1632|
|Asn|Gly|Ile|Arg|Tyr|Glu|Ile|Ser|Glu|Asp|Asn|Ser|Lys|His|Leu|Pro| |
| | |530| | | | |535| | | | |540| | | | |
|aat|cct|gat|ctg|aac|ctt|aaa|cca|gac|agt|acc|ggt|gat|gat|caa|cgc|1680|
|Asn|Pro|Asp|Leu|Asn|Leu|Lys|Pro|Asp|Ser|Thr|Gly|Asp|Asp|Gln|Arg| |
|545| | | | |550| | | | |555| | | | |560| | |
|aag|gcg|gtt|tta|aaa|cgc|gcg|ttt|cag|gtt|aac|gcc|agt|gag|ttg|tat|1728|
|Lys|Ala|Val|Leu|Lys|Arg|Ala|Phe|Gln|Val|Asn|Ala|Ser|Glu|Leu|Tyr| |
| | | | |565| | | | |570| | | | |575| | | |
|cag|atg|tta|ttg|atc|act|gat|cgt|aaa|gaa|gac|ggt|gtt|atc|aaa|aat|1776|
|Gln|Met|Leu|Leu|Ile|Thr|Asp|Arg|Lys|Glu|Asp|Gly|Val|Ile|Lys|Asn| |
| | | |580| | | | |585| | | | |590| | | | |
|aac|tta|gag|aat|ttg|tct|gat|ctg|tat|ttg|gtt|agt|ttg|ctg|gcc|cag|1824|
|Asn|Leu|Glu|Asn|Leu|Ser|Asp|Leu|Tyr|Leu|Val|Ser|Leu|Leu|Ala|Gln| |
| | |595| | | | |600| | | | |605| | | | |
|att|cat|aac|ctg|act|att|gct|gaa|ttg|aac|att|ttg|ttg|gtg|att|tgt|1872|
|Ile|His|Asn|Leu|Thr|Ile|Ala|Glu|Leu|Asn|Ile|Leu|Leu|Val|Ile|Cys| |
| | |610| | | | |615| | | | |620| | | | |
|ggc|tat|ggc|gac|acc|aac|att|tat|cag|att|acc|gac|gat|aat|tta|gcc|1920|
|Gly|Tyr|Gly|Asp|Thr|Asn|Ile|Tyr|Gln|Ile|Thr|Asp|Asp|Asn|Leu|Ala| |
|625| | | | |630| | | | |635| | | | |640| | |
|aaa|ata|gtg|gaa|aca|ttg|ttg|tgg|atc|act|caa|tgg|ttg|aag|acc|caa|1968|
|Lys|Ile|Val|Glu|Thr|Leu|Leu|Trp|Ile|Thr|Gln|Trp|Leu|Lys|Thr|Gln| |
| | | | |645| | | | |650| | | | |655| | | |
|aaa|tgg|aca|gtt|acc|gac|ctg|ttt|ctg|atg|acc|acg|gcc|act|tac|agc|2016|
|Lys|Trp|Thr|Val|Thr|Asp|Leu|Phe|Leu|Met|Thr|Thr|Ala|Thr|Tyr|Ser| |
| | | |660| | | | |665| | | | |670| | | | |
|acc|act|tta|acg|cca|gaa|att|agc|aat|ctg|acg|gct|acg|ttg|tct|tca|2064|
|Thr|Thr|Leu|Thr|Pro|Glu|Ile|Ser|Asn|Leu|Thr|Ala|Thr|Leu|Ser|Ser| |
| | |675| | | | |680| | | | |685| | | | |
|act|ttg|cat|ggc|aaa|gag|agt|ctg|att|ggg|gaa|gat|ctg|aaa|aga|gca|2112|
|Thr|Leu|His|Gly|Lys|Glu|Ser|Leu|Ile|Gly|Glu|Asp|Leu|Lys|Arg|Ala| |
| | |690| | | | |695| | | | |700| | | | |
|atg|gcg|cct|tgc|ttc|act|tcg|gct|ttg|cat|ttg|act|tct|caa|gaa|gtt|2160|

```
                  -continued

Met Ala Pro Cys Phe Thr Ser Ala Leu His Leu Thr Ser Gln Glu Val
705                 710                 715                 720 gcg tat gac ctg ctg ttg tgg ata gac cag att caa ccg gca caa ata    2208
Ala Tyr Asp Leu Leu Leu Trp Ile Asp Gln Ile Gln Pro Ala Gln Ile
                725                 730                 735 act gtt gat ggg ttt tgg gaa gaa gtg caa aca aca cca acc agc ttg    2256
Thr Val Asp Gly Phe Trp Glu Glu Val Gln Thr Thr Pro Thr Ser Leu
            740                 745                 750 aag gtg att acc ttt gct cag gtg ctg gca caa ttg agc ctg atc tat    2304
Lys Val Ile Thr Phe Ala Gln Val Leu Ala Gln Leu Ser Leu Ile Tyr
        755                 760                 765 cgt cgt att ggg tta agt gaa acg gaa ctg tca ctg atc gtg act caa    2352
Arg Arg Ile Gly Leu Ser Glu Thr Glu Leu Ser Leu Ile Val Thr Gln
    770                 775                 780 tct tct ctg cta gtg gca ggc aaa agc ata ctg gat cac ggt ctg tta    2400
Ser Ser Leu Leu Val Ala Gly Lys Ser Ile Leu Asp His Gly Leu Leu
785                 790                 795                 800 acc ctg atg gcc ttg gaa ggt ttt cat acc tgg gtt aat ggc ttg ggg    2448
Thr Leu Met Ala Leu Glu Gly Phe His Thr Trp Val Asn Gly Leu Gly
                805                 810                 815 caa cat gcc tcc ttg ata ttg gcg gcg ttg aaa gac gga gcc ttg aca    2496
Gln His Ala Ser Leu Ile Leu Ala Ala Leu Lys Asp Gly Ala Leu Thr
                820                 825                 830 gtt acc gat gta gca caa gct atg aat aag gag gaa tct ctc cta caa    2544
Val Thr Asp Val Ala Gln Ala Met Asn Lys Glu Glu Ser Leu Leu Gln
            835                 840                 845 atg gca gct aat cag gtg gag aag gat cta aca aaa ctg acc agt tgg    2592
Met Ala Ala Asn Gln Val Glu Lys Asp Leu Thr Lys Leu Thr Ser Trp
        850                 855                 860 aca cag att gac gct att ctg caa tgg tta cag atg tct tcg gcc ttg    2640
Thr Gln Ile Asp Ala Ile Leu Gln Trp Leu Gln Met Ser Ser Ala Leu
865                 870                 875                 880 gcg gtt tct cca ctg gat ctg gca ggg atg atg gcc ctg aaa tat ggg    2688
Ala Val Ser Pro Leu Asp Leu Ala Gly Met Met Ala Leu Lys Tyr Gly
                885                 890                 895 ata gat cat aac tat gct gcc tgg caa gct gcg gcg gct gcg ctg atg    2736
Ile Asp His Asn Tyr Ala Ala Trp Gln Ala Ala Ala Ala Ala Leu Met
                900                 905                 910 gct gat cat gct aat cag gca cag aaa aaa ctg gat gag acg ttc agt    2784
Ala Asp His Ala Asn Gln Ala Gln Lys Lys Leu Asp Glu Thr Phe Ser
            915                 920                 925 aag gca tta tgt aac tat tat att aat gct gtt gtc gat agt gct gct    2832
Lys Ala Leu Cys Asn Tyr Tyr Ile Asn Ala Val Val Asp Ser Ala Ala
        930                 935                 940 gga gta cgt gat cgt aac ggt tta tat acc tat ttg ctg att gat aat    2880
Gly Val Arg Asp Arg Asn Gly Leu Tyr Thr Tyr Leu Leu Ile Asp Asn
945                 950                 955                 960 cag gtt tct gcc gat gtg atc act tca cgt att gca gaa gct atc gcc    2928
Gln Val Ser Ala Asp Val Ile Thr Ser Arg Ile Ala Glu Ala Ile Ala
                965                 970                 975 ggt att caa ctg tac gtt aac cgg gct tta aac cga gat gaa ggt cag    2976
Gly Ile Gln Leu Tyr Val Asn Arg Ala Leu Asn Arg Asp Glu Gly Gln
                980                 985                 990 ctt gca tcg gac gtt agt acc cgt cag ttc ttc act gac tgg gaa cgt    3024
Leu Ala Ser Asp Val Ser Thr Arg Gln Phe Phe Thr Asp Trp Glu Arg
            995                 1000                1005 tac aat aaa cgt tac agt act tgg gct ggt gtc tct gaa ctg gtc tat    3072
Tyr Asn Lys Arg Tyr Ser Thr Trp Ala Gly Val Ser Glu Leu Val Tyr
        1010                1015                1020
```

-continued

```
tat cca gaa aac tat gtt gat ccc act cag cgc att ggg caa acc aaa      3120
Tyr Pro Glu Asn Tyr Val Asp Pro Thr Gln Arg Ile Gly Gln Thr Lys
1025                1030                1035                1040 atg atg gat gcg ctg ttg caa tcc atc aac agc cag cta aat gcg          3168
Met Met Asp Ala Leu Leu Gln Ser Ile Asn Ser Gln Leu Asn Ala
            1045                1050                1055 gat acg gtg gaa gat gct ttc aaa act tat ttg acc agc ttt gag cag      3216
Asp Thr Val Glu Asp Ala Phe Lys Thr Tyr Leu Thr Ser Phe Glu Gln
1060                1065                1070 gta gca aat ctg aaa gta att agt gct tac cac gat aat gtg aat gtg      3264
Val Ala Asn Leu Lys Val Ile Ser Ala Tyr His Asp Asn Val Asn Val
            1075                1080                1085 gat caa gga tta act tat ttt atc ggt atc gac caa gca gct ccg ggt      3312
Asp Gln Gly Leu Thr Tyr Phe Ile Gly Ile Asp Gln Ala Ala Pro Gly
1090                1095                1100 acg tat tac tgg cgt agt gtt gat cac agc aaa tgt gaa aat ggc aag      3360
Thr Tyr Tyr Trp Arg Ser Val Asp His Ser Lys Cys Glu Asn Gly Lys
1105                1110                1115                1120 ttt gcc gct aat gct tgg ggt gag tgg aat aaa att acc tgt gct gtc      3408
Phe Ala Ala Asn Ala Trp Gly Glu Trp Asn Lys Ile Thr Cys Ala Val
            1125                1130                1135 aat cct tgg aaa aat atc atc cgt ccg gtt gtt tat atg tcc cgc tta      3456
Asn Pro Trp Lys Asn Ile Ile Arg Pro Val Val Tyr Met Ser Arg Leu
1140                1145                1150 tat ctg cta tgg ctg gag cag caa tca aag aaa agt gat gat ggt aaa      3504
Tyr Leu Leu Trp Leu Glu Gln Gln Ser Lys Lys Ser Asp Asp Gly Lys
            1155                1160                1165 acc acg att tat caa tat aac tta aaa ctg gct cat att cgt tac gac      3552
Thr Thr Ile Tyr Gln Tyr Asn Leu Lys Leu Ala His Ile Arg Tyr Asp
1170                1175                1180 ggt agt tgg aat aca cca ttt act ttt gat gtg aca gaa aag gta aaa      3600
Gly Ser Trp Asn Thr Pro Phe Thr Phe Asp Val Thr Glu Lys Val Lys
1185                1190                1195                1200 aat tac acg tcg agt act gat gct gct gaa tct tta ggg ttg tat tgt      3648
Asn Tyr Thr Ser Ser Thr Asp Ala Ala Glu Ser Leu Gly Leu Tyr Cys
            1205                1210                1215 act ggt tat caa ggg gaa gac act cta tta gtt atg ttc tat tcg atg      3696
Thr Gly Tyr Gln Gly Glu Asp Thr Leu Leu Val Met Phe Tyr Ser Met
1220                1225                1230 cag agt agt tat agc tcc tat acc gat aat aat gcg ccg gtc act ggg      3744
Gln Ser Ser Tyr Ser Ser Tyr Thr Asp Asn Asn Ala Pro Val Thr Gly
            1235                1240                1245 cta tat att ttc gct gat atg tca tca gac aat atg acg aat gca caa      3792
Leu Tyr Ile Phe Ala Asp Met Ser Ser Asp Asn Met Thr Asn Ala Gln
1250                1255                1260 gca act aac tat tgg aat aac agt tat ccg caa ttt gat act gtg atg      3840
Ala Thr Asn Tyr Trp Asn Asn Ser Tyr Pro Gln Phe Asp Thr Val Met
1265                1270                1275                1280 gca gat ccg gat agc gac aat aaa aaa gtc ata acc aga aga gtt aat      3888
Ala Asp Pro Asp Ser Asp Asn Lys Lys Val Ile Thr Arg Arg Val Asn
            1285                1290                1295 aac cgt tat gcg gag gat tat gaa att cct tcc tct gtg aca agt aac      3936
Asn Arg Tyr Ala Glu Asp Tyr Glu Ile Pro Ser Ser Val Thr Ser Asn
1300                1305                1310 agt aat tat tct tgg ggt gat cac agt tta acc atg ctt tat ggt ggt      3984
Ser Asn Tyr Ser Trp Gly Asp His Ser Leu Thr Met Leu Tyr Gly Gly
            1315                1320                1325 agt gtt cct aat att act ttt gaa tcg gcg gca gaa gat tta agg cta      4032
Ser Val Pro Asn Ile Thr Phe Glu Ser Ala Ala Glu Asp Leu Arg Leu
1330                1335                1340
```

-continued

| | |
|---|---|
| tct acc aat atg gca ttg agt att att cat aat gga tat gcg gga acc<br>Ser Thr Asn Met Ala Leu Ser Ile Ile His Asn Gly Tyr Ala Gly Thr<br>1345                       1350                     1355                     1360 | 4080 |
| cgc cgt ata caa tgt aat ctt atg aaa caa tac gct tca tta ggt gat<br>Arg Arg Ile Gln Cys Asn Leu Met Lys Gln Tyr Ala Ser Leu Gly Asp<br>               1365                     1370                     1375 | 4128 |
| aaa ttt ata att tat gat tca tca ttt gat gat gca aac cgt ttt aat<br>Lys Phe Ile Ile Tyr Asp Ser Ser Phe Asp Asp Ala Asn Arg Phe Asn<br>1380                       1385                     1390 | 4176 |
| ctg gtg cca ttg ttt aaa ttc gga aaa gac gag aac tca gat gat agt<br>Leu Val Pro Leu Phe Lys Phe Gly Lys Asp Glu Asn Ser Asp Asp Ser<br>               1395                     1400                     1405 | 4224 |
| att tgt ata tat aat gaa aac cct tcc tct gaa gat aag aag tgg tat<br>Ile Cys Ile Tyr Asn Glu Asn Pro Ser Ser Glu Asp Lys Lys Trp Tyr<br>1410                       1415                     1420 | 4272 |
| ttt tct tcg aaa gat gac aat aaa aca gcg gat tat aat ggt gga act<br>Phe Ser Ser Lys Asp Asp Asn Lys Thr Ala Asp Tyr Asn Gly Gly Thr<br>1425                       1430                     1435                     1440 | 4320 |
| caa tgt ata gat gct gga acc agt aac aaa gat ttt tat tat aat ctc<br>Gln Cys Ile Asp Ala Gly Thr Ser Asn Lys Asp Phe Tyr Tyr Asn Leu<br>               1445                     1450                     1455 | 4368 |
| cag gag att gaa gta att agt gtt act ggt ggg tat tgg tcg agt tat<br>Gln Glu Ile Glu Val Ile Ser Val Thr Gly Gly Tyr Trp Ser Ser Tyr<br>               1460                     1465                     1470 | 4416 |
| aaa ata tcc aac ccg att aat atc aat acg ggc att gat agt gct aaa<br>Lys Ile Ser Asn Pro Ile Asn Ile Asn Thr Gly Ile Asp Ser Ala Lys<br>1475                       1480                     1485 | 4464 |
| gta aaa gtc acc gta aaa gcg ggt ggt gac gat caa atc ttt act gct<br>Val Lys Val Thr Val Lys Ala Gly Gly Asp Asp Gln Ile Phe Thr Ala<br>               1490                     1495                     1500 | 4512 |
| gat aat agt acc tat gtt cct cag caa ccg gca ccc agt ttt gag gag<br>Asp Asn Ser Thr Tyr Val Pro Gln Gln Pro Ala Pro Ser Phe Glu Glu<br>1505                       1510                     1515                     1520 | 4560 |
| atg att tat cag ttc aat aac ctg aca ata gat tgt aag aat tta aat<br>Met Ile Tyr Gln Phe Asn Asn Leu Thr Ile Asp Cys Lys Asn Leu Asn<br>               1525                     1530                     1535 | 4608 |
| ttc atc gac aat cag gca cat att gag att gat ttc acc gct acg gca<br>Phe Ile Asp Asn Gln Ala His Ile Glu Ile Asp Phe Thr Ala Thr Ala<br>1540                       1545                     1550 | 4656 |
| caa gat ggc cga ttc ttg ggt gca gaa act ttt att atc ccg gta act<br>Gln Asp Gly Arg Phe Leu Gly Ala Glu Thr Phe Ile Ile Pro Val Thr<br>               1555                     1560                     1565 | 4704 |
| aaa aaa gtt ctc ggt act gag aac gtg att gcg tta tat agc gaa aat<br>Lys Lys Val Leu Gly Thr Glu Asn Val Ile Ala Leu Tyr Ser Glu Asn<br>1570                       1575                     1580 | 4752 |
| aac ggt gtt caa tat atg caa att ggc gca tat cgt acc cgt ttg aat<br>Asn Gly Val Gln Tyr Met Gln Ile Gly Ala Tyr Arg Thr Arg Leu Asn<br>1585                       1590                     1595                     1600 | 4800 |
| acg tta ttc gct caa cag ttg gtt agc cgt gct aat cgt ggc att gat<br>Thr Leu Phe Ala Gln Gln Leu Val Ser Arg Ala Asn Arg Gly Ile Asp<br>               1605                     1610                     1615 | 4848 |
| gca gtg ctc agt atg gaa act cag aat att cag gaa ccg caa tta gga<br>Ala Val Leu Ser Met Glu Thr Gln Asn Ile Gln Glu Pro Gln Leu Gly<br>1620                       1625                     1630 | 4896 |
| gcg ggc aca tat gtg cag ctt gtg ttg gat aaa tat gat gag tct att<br>Ala Gly Thr Tyr Val Gln Leu Val Leu Asp Lys Tyr Asp Glu Ser Ile<br>               1635                     1640                     1645 | 4944 |
| cat ggc act aat aaa agc ttt gct att gaa tat gtt gat ata ttt aaa<br>His Gly Thr Asn Lys Ser Phe Ala Ile Glu Tyr Val Asp Ile Phe Lys | 4992 |

```
                                                     -continued
     1650                  1655                  1660
gag aac gat agt ttt gtg att tat caa gga gaa ctt agc gaa aca agt      5040
Glu Asn Asp Ser Phe Val Ile Tyr Gln Gly Glu Leu Ser Glu Thr Ser
1665              1670              1675              1680 caa act gtt gtg aaa gtt ttc tta tcc tat ttt ata gag gcg act gga      5088
Gln Thr Val Val Lys Val Phe Leu Ser Tyr Phe Ile Glu Ala Thr Gly
              1685              1690              1695 aat aag aac cac tta tgg gta cgt gct aaa tac caa aag gaa acg act      5136
Asn Lys Asn His Leu Trp Val Arg Ala Lys Tyr Gln Lys Glu Thr Thr
1700              1705              1710 gat aag atc ttg ttc gac cgt act gat gag aaa gat ccg cac ggt tgg      5184
Asp Lys Ile Leu Phe Asp Arg Thr Asp Glu Lys Asp Pro His Gly Trp
        1715              1720              1725 ttt ctc agc gac gat cac aag acc ttt agt ggt ctc tct tcc gca cag      5232
Phe Leu Ser Asp Asp His Lys Thr Phe Ser Gly Leu Ser Ser Ala Gln
        1730              1735              1740 gca tta aag aac gac agt gaa ccg atg gat ttc tct ggc gcc aat gct      5280
Ala Leu Lys Asn Asp Ser Glu Pro Met Asp Phe Ser Gly Ala Asn Ala
1745              1750              1755              1760 ctc tat ttc tgg gaa ctg ttc tat tac acg ccg atg atg atg gct cat      5328
Leu Tyr Phe Trp Glu Leu Phe Tyr Tyr Thr Pro Met Met Met Ala His
              1765              1770              1775 cgt ttg ttg cag gaa cag aat ttt gat gcg gcg aac cat tgg ttc cgt      5376
Arg Leu Leu Gln Glu Gln Asn Phe Asp Ala Ala Asn His Trp Phe Arg
        1780              1785              1790 tat gtc tgg agt cca tcc ggt tat atc gtt gat ggt aaa att gct atc      5424
Tyr Val Trp Ser Pro Ser Gly Tyr Ile Val Asp Gly Lys Ile Ala Ile
        1795              1800              1805 tac cac tgg aac gtg cga ccg ctg gaa gaa gac acc agt tgg aat gca      5472
Tyr His Trp Asn Val Arg Pro Leu Glu Glu Asp Thr Ser Trp Asn Ala
1810              1815              1820 caa caa ctg gac tcc acc gat cca gat gct gta gcc caa gat gat ccg      5520
Gln Gln Leu Asp Ser Thr Asp Pro Asp Ala Val Ala Gln Asp Asp Pro
1825              1830              1835              1840 atg cac tac aag gtg gct acc ttt atg gcg acg ttg gat ctg cta atg      5568
Met His Tyr Lys Val Ala Thr Phe Met Ala Thr Leu Asp Leu Leu Met
              1845              1850              1855 gcc cgt ggt gat gct gct tac cgc cag tta gag cgt gat acg ttg gct      5616
Ala Arg Gly Asp Ala Ala Tyr Arg Gln Leu Glu Arg Asp Thr Leu Ala
        1860              1865              1870 gaa gct aaa atg tgg tat aca cag gcg ctt aat ctg ttg ggt gat gag      5664
Glu Ala Lys Met Trp Tyr Thr Gln Ala Leu Asn Leu Leu Gly Asp Glu
        1875              1880              1885 cca caa gtg atg ctg agt acg act tgg gct aat cca aca ttg ggt aat      5712
Pro Gln Val Met Leu Ser Thr Thr Trp Ala Asn Pro Thr Leu Gly Asn
        1890              1895              1900 gct gct tca aaa acc aca cag cag gtt cgt cag caa gtg ctt acc cag      5760
Ala Ala Ser Lys Thr Thr Gln Gln Val Arg Gln Gln Val Leu Thr Gln
1905              1910              1915              1920 ttg cgt ctc aat agc agg gta aaa acc ccg ttg cta gga aca gcc aat      5808
Leu Arg Leu Asn Ser Arg Val Lys Thr Pro Leu Leu Gly Thr Ala Asn
              1925              1930              1935 tcc ctg acc gct tta ttc ctg ccg cag gaa aat agc aag ctc aaa ggc      5856
Ser Leu Thr Ala Leu Phe Leu Pro Gln Glu Asn Ser Lys Leu Lys Gly
        1940              1945              1950 tac tgg cgg aca ctg gcg cag cgt atg ttt aat tta cgt cat aat ctg      5904
Tyr Trp Arg Thr Leu Ala Gln Arg Met Phe Asn Leu Arg His Asn Leu
        1955              1960              1965 tcg att gac ggc cag ccg ctc tcc ttg ccg ctg tat gct aaa ccg gct      5952
```

```
Ser Ile Asp Gly Gln Pro Leu Ser Leu Pro Leu Tyr Ala Lys Pro Ala
    1970                1975                1980 gat cca aaa gct tta ctg agt gcg gcg gtt tca gct tct caa ggg gga    6000
Asp Pro Lys Ala Leu Leu Ser Ala Ala Val Ser Ala Ser Gln Gly Gly
1985                1990                1995                2000 gcc gac ttg ccg aag gcg ccg ctg act att cac cgc ttc cct caa atg    6048
Ala Asp Leu Pro Lys Ala Pro Leu Thr Ile His Arg Phe Pro Gln Met
                2005                2010                2015 cta gaa ggg gca cgg ggc ttg gtt aac cag ctt ata cag ttc ggt agt    6096
Leu Glu Gly Ala Arg Gly Leu Val Asn Gln Leu Ile Gln Phe Gly Ser
            2020                2025                2030 tca cta ttg ggg tac agt gag cgt cag gat gcg gaa gct atg agt caa    6144
Ser Leu Leu Gly Tyr Ser Glu Arg Gln Asp Ala Glu Ala Met Ser Gln
        2035                2040                2045 cta ctg caa acc caa gcc agc gag tta ata ctg acc agt att cgt atg    6192
Leu Leu Gln Thr Gln Ala Ser Glu Leu Ile Leu Thr Ser Ile Arg Met
    2050                2055                2060 cag gat aac caa ttg gca gag ctg gat tcg gaa aaa acc gcc ttg caa    6240
Gln Asp Asn Gln Leu Ala Glu Leu Asp Ser Glu Lys Thr Ala Leu Gln
2065                2070                2075                2080 gtc tct tta gct gga gtg caa caa cgg ttt gac agc tat agc caa ctg    6288
Val Ser Leu Ala Gly Val Gln Gln Arg Phe Asp Ser Tyr Ser Gln Leu
                2085                2090                2095 tat gag gag aac atc aac gca ggt gag cag cga gcg ctg gcg tta cgc    6336
Tyr Glu Glu Asn Ile Asn Ala Gly Glu Gln Arg Ala Leu Ala Leu Arg
            2100                2105                2110 tca gaa tct gct att gag tct cag gga gcg cag att tcc cgt atg gca    6384
Ser Glu Ser Ala Ile Glu Ser Gln Gly Ala Gln Ile Ser Arg Met Ala
        2115                2120                2125 ggc gcg ggt gtt gat atg gca cca aat atc ttc ggc ctg gct gat ggc    6432
Gly Ala Gly Val Asp Met Ala Pro Asn Ile Phe Gly Leu Ala Asp Gly
    2130                2135                2140 ggc atg cat tat ggt gct att gcc tat gcc atc gct gac ggt att gag    6480
Gly Met His Tyr Gly Ala Ile Ala Tyr Ala Ile Ala Asp Gly Ile Glu
2145                2150                2155                2160 ttg agt gct tct gcc aag atg gtt gat gcg gag aaa gtt gct cag tcg    6528
Leu Ser Ala Ser Ala Lys Met Val Asp Ala Glu Lys Val Ala Gln Ser
                2165                2170                2175 gaa ata tat cgc cgt cgc cgt caa gaa tgg aaa att cag cgt gac aac    6576
Glu Ile Tyr Arg Arg Arg Arg Gln Glu Trp Lys Ile Gln Arg Asp Asn
            2180                2185                2190 gca caa gcg gag att aac cag tta aac gcg caa ctg gaa tca ctg tct    6624
Ala Gln Ala Glu Ile Asn Gln Leu Asn Ala Gln Leu Glu Ser Leu Ser
        2195                2200                2205 att cgc cgt gaa gcc gct gaa atg caa aaa gag tac ctg aaa acc cag    6672
Ile Arg Arg Glu Ala Ala Glu Met Gln Lys Glu Tyr Leu Lys Thr Gln
    2210                2215                2220 caa gct cag gcg cag gca caa ctt act ttc tta aga agc aaa ttc agt    6720
Gln Ala Gln Ala Gln Ala Gln Leu Thr Phe Leu Arg Ser Lys Phe Ser
2225                2230                2235                2240 aat caa gcg tta tat agt tgg tta cga ggg cgt ttg tca ggt att tat    6768
Asn Gln Ala Leu Tyr Ser Trp Leu Arg Gly Arg Leu Ser Gly Ile Tyr
                2245                2250                2255 ttc cag ttc tat gac ttg gcc gta tca cgt tgc ctg atg gca gag caa    6816
Phe Gln Phe Tyr Asp Leu Ala Val Ser Arg Cys Leu Met Ala Glu Gln
            2260                2265                2270 tcc tat caa tgg gaa gct aat gat aat tcc att agc ttt gtc aaa ccg    6864
Ser Tyr Gln Trp Glu Ala Asn Asp Asn Ser Ile Ser Phe Val Lys Pro
        2275                2280                2285
```

-continued

```
ggt gca tgg caa gga act tac gcc ggc tta ttg tgt gga gaa gct ttg     6912
Gly Ala Trp Gln Gly Thr Tyr Ala Gly Leu Leu Cys Gly Glu Ala Leu
    2290                2295                2300 ata caa aat ctg gca caa atg gaa gag gca tat ctg aaa tgg gaa tct     6960
Ile Gln Asn Leu Ala Gln Met Glu Glu Ala Tyr Leu Lys Trp Glu Ser
2305                2310                2315                2320 cgc gct ttg gaa gta gaa cgc acg gtt tca ttg gca gtg gtt tat gat     7008
Arg Ala Leu Glu Val Glu Arg Thr Val Ser Leu Ala Val Val Tyr Asp
                2325                2330                2335 tca ctg gaa ggt aat gat cgt ttt aat tta gcg gaa caa ata cct gca     7056
Ser Leu Glu Gly Asn Asp Arg Phe Asn Leu Ala Glu Gln Ile Pro Ala
            2340                2345                2350 tta ttg gat aag ggg gag gga aca gca gga act aaa gaa aat ggg tta     7104
Leu Leu Asp Lys Gly Glu Gly Thr Ala Gly Thr Lys Glu Asn Gly Leu
        2355                2360                2365 tca ttg gct aat gct atc ctg tca gct tcg gtc aaa ttg tcc gac ttg     7152
Ser Leu Ala Asn Ala Ile Leu Ser Ala Ser Val Lys Leu Ser Asp Leu
    2370                2375                2380 aaa ctg gga acg gat tat cca gac agt atc gtt ggt agc aac aag gtt     7200
Lys Leu Gly Thr Asp Tyr Pro Asp Ser Ile Val Gly Ser Asn Lys Val
2385                2390                2395                2400 cgt cgt att aag caa atc agt gtt tcg cta cct gca ttg gtt ggg cct     7248
Arg Arg Ile Lys Gln Ile Ser Val Ser Leu Pro Ala Leu Val Gly Pro
                2405                2410                2415 tat cag gat gtt cag gct atg ctc agc tat ggt ggc agt act caa ttg     7296
Tyr Gln Asp Val Gln Ala Met Leu Ser Tyr Gly Gly Ser Thr Gln Leu
            2420                2425                2430 ccg aaa ggt tgt tca gcg ttg gct gtg tct cat ggt acc aat gat agt     7344
Pro Lys Gly Cys Ser Ala Leu Ala Val Ser His Gly Thr Asn Asp Ser
        2435                2440                2445 ggt cag ttc cag ttg gat ttc aat gac ggc aaa tac ctg cca ttt gaa     7392
Gly Gln Phe Gln Leu Asp Phe Asn Asp Gly Lys Tyr Leu Pro Phe Glu
    2450                2455                2460 ggt att gct ctt gat gat cag ggt aca ctg aat ctt caa ttt ccg aat     7440
Gly Ile Ala Leu Asp Asp Gln Gly Thr Leu Asn Leu Gln Phe Pro Asn
2465                2470                2475                2480 gct acc gac aag cag aaa gca ata ttg caa act atg agc gat att att     7488
Ala Thr Asp Lys Gln Lys Ala Ile Leu Gln Thr Met Ser Asp Ile Ile
                2485                2490                2495 ttg cat att cgt tat acc atc cgt taa                                 7515
Leu His Ile Arg Tyr Thr Ile Arg
            2500
```

```
<210> SEQ ID NO 3
<211> LENGTH: 7577
<212> TYPE: DNA
<213> ORGANISM: Artificial Sequence
<220> FEATURE:
<221> NAME/KEY: CDS
<222> LOCATION: (3)..(7553)
<220> FEATURE:
<223> OTHER INFORMATION: Description of Artificial Sequence:hemicot tcdA

<400> SEQUENCE: 3 cc atg gct aac gag tcc gtc aag gag atc cca gac gtc ctc aag tcc       47
   Met Ala Asn Glu Ser Val Lys Glu Ile Pro Asp Val Leu Lys Ser
     1               5                  10                  15 caa tgc ggt ttc aac tgc ctc act gac atc tcc cac agc tcc ttc aac      95
Gln Cys Gly Phe Asn Cys Leu Thr Asp Ile Ser His Ser Ser Phe Asn
                20                  25                  30 gag ttc aga caa caa gtc tct gag cac ctc tcc tgg tcc gag acc cat     143
Glu Phe Arg Gln Gln Val Ser Glu His Leu Ser Trp Ser Glu Thr His
```

```
                    35                   40                   45
gac ctc tac cat gac gct cag caa gct cag aag gac aac agg ctc tac       191
Asp Leu Tyr His Asp Ala Gln Gln Ala Gln Lys Asp Asn Arg Leu Tyr
         50                   55                   60 gag gct agg atc ctc aag agg gct aac cca caa ctc cag aac gct gtc       239
Glu Ala Arg Ile Leu Lys Arg Ala Asn Pro Gln Leu Gln Asn Ala Val
 65                   70                   75 cac ctc gcc atc ttg gct cca aac gct gag ttg att ggt tac aac aac       287
His Leu Ala Ile Leu Ala Pro Asn Ala Glu Leu Ile Gly Tyr Asn Asn
 80                   85                   90                   95 cag ttc tct ggc aga gct agc cag tac gtg gct cct ggt aca gtc tcc       335
Gln Phe Ser Gly Arg Ala Ser Gln Tyr Val Ala Pro Gly Thr Val Ser
                 100                  105                  110 tcc atg ttc agc cca gcc gct tac ctc act gag ttg tac cgc gag gct       383
Ser Met Phe Ser Pro Ala Ala Tyr Leu Thr Glu Leu Tyr Arg Glu Ala
             115                  120                  125 agg aac ctt cat gct tct gac tcc gtc tac tac ttg gac aca cgc aga       431
Arg Asn Leu His Ala Ser Asp Ser Val Tyr Tyr Leu Asp Thr Arg Arg
         130                  135                  140 cca gac ctc aag agc atg gcc ctc agc caa cag aac atg gac att gag       479
Pro Asp Leu Lys Ser Met Ala Leu Ser Gln Gln Asn Met Asp Ile Glu
 145                  150                  155 ttg tcc acc ctc tcc ttg agc aac gag ctt ctc ttg gag tcc atc aag       527
Leu Ser Thr Leu Ser Leu Ser Asn Glu Leu Leu Leu Glu Ser Ile Lys
 160                  165                  170                  175 act gag agc aag ttg gag aac tac acc aag gtc atg gag atg ctc tcc       575
Thr Glu Ser Lys Leu Glu Asn Tyr Thr Lys Val Met Glu Met Leu Ser
                 180                  185                  190 acc ttc aga cca agc ggt gca act cca tac cat gat gcc tac gag aac       623
Thr Phe Arg Pro Ser Gly Ala Thr Pro Tyr His Asp Ala Tyr Glu Asn
             195                  200                  205 gtc agg gag gtc atc caa ctt caa gac cct ggt ctt gag caa ctc aac       671
Val Arg Glu Val Ile Gln Leu Gln Asp Pro Gly Leu Glu Gln Leu Asn
         210                  215                  220 gct tct cca gcc att gct ggt ttg atg cac cag gca tcc ttg ctc ggt       719
Ala Ser Pro Ala Ile Ala Gly Leu Met His Gln Ala Ser Leu Leu Gly
 225                  230                  235 atc aac gcc tcc atc tct cct gag ttg ttc aac atc ttg act gag gag       767
Ile Asn Ala Ser Ile Ser Pro Glu Leu Phe Asn Ile Leu Thr Glu Glu
 240                  245                  250                  255 atc act gag ggc aac gct gag gag ttg tac aag aag aac ttc ggc aac       815
Ile Thr Glu Gly Asn Ala Glu Glu Leu Tyr Lys Lys Asn Phe Gly Asn
                 260                  265                  270 att gag cca gcc tct ctt gca atg cct gag tac ctc aag agg tac tac       863
Ile Glu Pro Ala Ser Leu Ala Met Pro Glu Tyr Leu Lys Arg Tyr Tyr
             275                  280                  285 aac ttg tct gat gag gag ctt tct caa ttc att ggc aag gct tcc aac       911
Asn Leu Ser Asp Glu Glu Leu Ser Gln Phe Ile Gly Lys Ala Ser Asn
         290                  295                  300 ttc ggt caa cag gag tac agc aac aac cag ctc atc act cca gtt gtg       959
Phe Gly Gln Gln Glu Tyr Ser Asn Asn Gln Leu Ile Thr Pro Val Val
 305                  310                  315 aac tcc tct gat ggc act gtg aag gtc tac cgc atc aca cgt gag tac      1007
Asn Ser Ser Asp Gly Thr Val Lys Val Tyr Arg Ile Thr Arg Glu Tyr
 320                  325                  330                  335 acc aca aac gcc tac caa atg gat gtt gag ttg ttc cca ttc ggt ggt      1055
Thr Thr Asn Ala Tyr Gln Met Asp Val Glu Leu Phe Pro Phe Gly Gly
                 340                  345                  350 gag aac tac aga ctt gac tac aag ttc aag aac ttc tac aac gcc tcc      1103
```

```
                Glu Asn Tyr Arg Leu Asp Tyr Lys Phe Lys Asn Phe Tyr Asn Ala Ser
                                355                 360                 365 tac ctc tcc atc aag ttg aac gac aag agg gag ctt gtc agg act gag           1151
Tyr Leu Ser Ile Lys Leu Asn Asp Lys Arg Glu Leu Val Arg Thr Glu
            370                 375                 380 ggt gct cct caa gtg aac att gag tac tct gcc aac atc acc ctc aac           1199
Gly Ala Pro Gln Val Asn Ile Glu Tyr Ser Ala Asn Ile Thr Leu Asn
385                 390                 395 aca gct gac atc tct caa cca ttc gag att ggt ttg acc aga gtc ctt           1247
Thr Ala Asp Ile Ser Gln Pro Phe Glu Ile Gly Leu Thr Arg Val Leu
400                 405                 410                 415 ccc tct ggc tcc tgg gcc tac gct gca gcc aag ttc act gtt gag gag           1295
Pro Ser Gly Ser Trp Ala Tyr Ala Ala Ala Lys Phe Thr Val Glu Glu
                420                 425                 430 tac aac cag tac tct ttc ctc ttg aag ctc aac aag gca att cgt ctc           1343
Tyr Asn Gln Tyr Ser Phe Leu Leu Lys Leu Asn Lys Ala Ile Arg Leu
            435                 440                 445 agc aga gcc act gag ttg tct ccc acc atc ttg gag ggc att gtg agg           1391
Ser Arg Ala Thr Glu Leu Ser Pro Thr Ile Leu Glu Gly Ile Val Arg
        450                 455                 460 tct gtc aac ctt caa ctt gac atc aac act gat gtg ctt ggc aag gtc           1439
Ser Val Asn Leu Gln Leu Asp Ile Asn Thr Asp Val Leu Gly Lys Val
465                 470                 475 ttc ctc acc aag tac tac atg caa cgc tac gcc atc cat gct gag act           1487
Phe Leu Thr Lys Tyr Tyr Met Gln Arg Tyr Ala Ile His Ala Glu Thr
480                 485                 490                 495 gca ctc atc ctc tgc aac gca ccc atc tct caa cgc tcc tac gac aac           1535
Ala Leu Ile Leu Cys Asn Ala Pro Ile Ser Gln Arg Ser Tyr Asp Asn
                500                 505                 510 cag cct tcc cag ttc gac agg ctc ttc aac act cct ctc ttg aac ggc           1583
Gln Pro Ser Gln Phe Asp Arg Leu Phe Asn Thr Pro Leu Leu Asn Gly
            515                 520                 525 cag tac ttc tcc act ggt gat gag gag att gac ctc aac tct ggc tcc           1631
Gln Tyr Phe Ser Thr Gly Asp Glu Glu Ile Asp Leu Asn Ser Gly Ser
        530                 535                 540 aca ggt gac tgg aga aag acc atc ttg aag agg gcc ttc aac att gat           1679
Thr Gly Asp Trp Arg Lys Thr Ile Leu Lys Arg Ala Phe Asn Ile Asp
545                 550                 555 gat gtc tct ctc ttc cgt ctc ttg aag atc aca gat cac gac aac aag           1727
Asp Val Ser Leu Phe Arg Leu Leu Lys Ile Thr Asp His Asp Asn Lys
560                 565                 570                 575 gat ggc aag atc aag aac aac ttg aag aac ctt tcc aac ctc tac att           1775
Asp Gly Lys Ile Lys Asn Asn Leu Lys Asn Leu Ser Asn Leu Tyr Ile
                580                 585                 590 ggc aag ttg ctt gca gac atc cac caa ctc acc att gat gag ttg gac           1823
Gly Lys Leu Leu Ala Asp Ile His Gln Leu Thr Ile Asp Glu Leu Asp
            595                 600                 605 ctc ttg ctc att gca gtc ggt gag ggc aag acc aac ctc tct gca atc           1871
Leu Leu Leu Ile Ala Val Gly Glu Gly Lys Thr Asn Leu Ser Ala Ile
        610                 615                 620 tct gac aag cag ttg gca acc ctc atc agg aag ttg aac acc atc acc           1919
Ser Asp Lys Gln Leu Ala Thr Leu Ile Arg Lys Leu Asn Thr Ile Thr
625                 630                 635 tcc tgg ctt cac acc cag aag tgg tct gtc ttc caa ctc ttc atc atg           1967
Ser Trp Leu His Thr Gln Lys Trp Ser Val Phe Gln Leu Phe Ile Met
640                 645                 650                 655 acc agc acc tcc tac aac aag acc ctc act cct gag atc aag aac ctc           2015
Thr Ser Thr Ser Tyr Asn Lys Thr Leu Thr Pro Glu Ile Lys Asn Leu
                660                 665                 670
```

```
ttg gac aca gtc tac cac ggt ctc caa ggc ttc gac aag gac aag gct    2063
Leu Asp Thr Val Tyr His Gly Leu Gln Gly Phe Asp Lys Asp Lys Ala
            675                 680                 685 gac ttg ctt cat gtc atg gct ccc tac att gca gcc acc ctc caa ctc    2111
Asp Leu Leu His Val Met Ala Pro Tyr Ile Ala Ala Thr Leu Gln Leu
        690                 695                 700 tcc tct gag aac gtg gct cac tct gtc ttg ctc tgg gct gac aag ctc    2159
Ser Ser Glu Asn Val Ala His Ser Val Leu Leu Trp Ala Asp Lys Leu
705                 710                 715 caa cct ggt gat ggt gcc atg act gct gag aag ttc tgg gac tgg ctc    2207
Gln Pro Gly Asp Gly Ala Met Thr Ala Glu Lys Phe Trp Asp Trp Leu
720                 725                 730                 735 aac acc aag tac aca cca ggc tcc tct gag gct gtt gag act caa gag    2255
Asn Thr Lys Tyr Thr Pro Gly Ser Ser Glu Ala Val Glu Thr Gln Glu
            740                 745                 750 cac att gtg caa tac tgc cag gct ctt gca cag ttg gag atg gtc tac    2303
His Ile Val Gln Tyr Cys Gln Ala Leu Ala Gln Leu Glu Met Val Tyr
        755                 760                 765 cac tcc act ggc atc aac gag aac gct ttc aga ctc ttc gtc acc aag    2351
His Ser Thr Gly Ile Asn Glu Asn Ala Phe Arg Leu Phe Val Thr Lys
770                 775                 780 cct gag atg ttc ggt gct gcc aca ggt gct gca cct gct cat gat gct    2399
Pro Glu Met Phe Gly Ala Ala Thr Gly Ala Ala Pro Ala His Asp Ala
785                 790                 795 ctc tcc ctc atc atg ttg acc agg ttc gct gac tgg gtc aac gct ctt    2447
Leu Ser Leu Ile Met Leu Thr Arg Phe Ala Asp Trp Val Asn Ala Leu
800                 805                 810                 815 ggt gag aag gct tcc tct gtc ttg gct gcc ttc gag gcc aac tcc ctc    2495
Gly Glu Lys Ala Ser Ser Val Leu Ala Ala Phe Glu Ala Asn Ser Leu
            820                 825                 830 act gct gag caa ctt gct gat gcc atg aac ctt gat gcc aac ctc ttg    2543
Thr Ala Glu Gln Leu Ala Asp Ala Met Asn Leu Asp Ala Asn Leu Leu
        835                 840                 845 ctc caa gct tcc att caa gct cag aac cac caa cac ctc cca cct gtc    2591
Leu Gln Ala Ser Ile Gln Ala Gln Asn His Gln His Leu Pro Pro Val
850                 855                 860 act cca gag aac gct ttc tcc tgc tgg acc tcc atc aac acc atc ctc    2639
Thr Pro Glu Asn Ala Phe Ser Cys Trp Thr Ser Ile Asn Thr Ile Leu
865                 870                 875 caa tgg gtc aac gtg gct cag caa ctc aac gtg gct cca caa ggt gtc    2687
Gln Trp Val Asn Val Ala Gln Gln Leu Asn Val Ala Pro Gln Gly Val
880                 885                 890                 895 tct gct ttg gtc ggt ctt gac tac atc cag tcc atg aag gag aca cca    2735
Ser Ala Leu Val Gly Leu Asp Tyr Ile Gln Ser Met Lys Glu Thr Pro
            900                 905                 910 acc tac gct caa tgg gag aac gca gct ggt gtc ttg act gct ggt ctc    2783
Thr Tyr Ala Gln Trp Glu Asn Ala Ala Gly Val Leu Thr Ala Gly Leu
        915                 920                 925 aac tcc caa cag gcc aac acc ctc cat gct ttc ttg gat gag tct cgc    2831
Asn Ser Gln Gln Ala Asn Thr Leu His Ala Phe Leu Asp Glu Ser Arg
930                 935                 940 tct gct gcc ctc tcc acc tac tac atc agg caa gtc gcc aag gca gct    2879
Ser Ala Ala Leu Ser Thr Tyr Tyr Ile Arg Gln Val Ala Lys Ala Ala
945                 950                 955 gct gcc atc aag tct cgc gat gac ctc tac caa tac ctc ctc att gac    2927
Ala Ala Ile Lys Ser Arg Asp Asp Leu Tyr Gln Tyr Leu Leu Ile Asp
960                 965                 970                 975 aac cag gtc tct gct gcc atc aag acc acc agg atc gct gag gcc atc    2975
Asn Gln Val Ser Ala Ala Ile Lys Thr Thr Arg Ile Ala Glu Ala Ile
            980                 985                 990
```

```
gct tcc atc caa ctc tac gtc aac cgc gct ctt gag aac gtt gag gag    3023
Ala Ser Ile Gln Leu Tyr Val Asn Arg Ala Leu Glu Asn Val Glu Glu
            995                 1000                1005 aac gcc aac tct ggt gtc atc tct cgc caa ttc ttc atc gac tgg gac    3071
Asn Ala Asn Ser Gly Val Ile Ser Arg Gln Phe Phe Ile Asp Trp Asp
        1010                1015                1020 aag tac aac aag agg tac tcc acc tgg gct ggt gtc tct caa ctt gtc    3119
Lys Tyr Asn Lys Arg Tyr Ser Thr Trp Ala Gly Val Ser Gln Leu Val
    1025                1030                1035 tac tac cca gag aac tac att gac cca acc atg agg att ggt cag acc    3167
Tyr Tyr Pro Glu Asn Tyr Ile Asp Pro Thr Met Arg Ile Gly Gln Thr
1040                1045                1050                1055 aag atg atg gat gct ctc ttg caa tct gtc tcc caa agc caa ctc aac    3215
Lys Met Met Asp Ala Leu Leu Gln Ser Val Ser Gln Ser Gln Leu Asn
            1060                1065                1070 gct gac act gtg gag gat gcc ttc atg agc tac ctc acc tcc ttc gag    3263
Ala Asp Thr Val Glu Asp Ala Phe Met Ser Tyr Leu Thr Ser Phe Glu
        1075                1080                1085 caa gtt gcc aac ctc aag gtc atc tct gct tac cat gac aac atc aac    3311
Gln Val Ala Asn Leu Lys Val Ile Ser Ala Tyr His Asp Asn Ile Asn
    1090                1095                1100 aac gac caa ggt ctc acc tac ttc att ggt ctc tct gag act gat gct    3359
Asn Asp Gln Gly Leu Thr Tyr Phe Ile Gly Leu Ser Glu Thr Asp Ala
1105                1110                1115 ggt gag tac tac tgg aga tcc gtg gac cac agc aag ttc aac gat ggc    3407
Gly Glu Tyr Tyr Trp Arg Ser Val Asp His Ser Lys Phe Asn Asp Gly
1120                1125                1130                1135 aag ttc gct gca aac gct tgg tct gag tgg cac aag att gac tgc cct    3455
Lys Phe Ala Ala Asn Ala Trp Ser Glu Trp His Lys Ile Asp Cys Pro
            1140                1145                1150 atc aac cca tac aag tcc acc atc aga cct gtc atc tac aag agc cgc    3503
Ile Asn Pro Tyr Lys Ser Thr Ile Arg Pro Val Ile Tyr Lys Ser Arg
        1155                1160                1165 ctc tac ttg ctc tgg ctt gag cag aag gag atc acc aag caa act ggc    3551
Leu Tyr Leu Leu Trp Leu Glu Gln Lys Glu Ile Thr Lys Gln Thr Gly
    1170                1175                1180 aac tcc aag gat ggt tac caa act gag act gac tac cgc tac gag ttg    3599
Asn Ser Lys Asp Gly Tyr Gln Thr Glu Thr Asp Tyr Arg Tyr Glu Leu
1185                1190                1195 aag ttg gct cac atc cgc tac gat ggt acc tgg aac act cca atc acc    3647
Lys Leu Ala His Ile Arg Tyr Asp Gly Thr Trp Asn Thr Pro Ile Thr
1200                1205                1210                1215 ttc gat gtc aac aag aag atc agc gag ttg aag ttg gag aag aac cgt    3695
Phe Asp Val Asn Lys Lys Ile Ser Glu Leu Lys Leu Glu Lys Asn Arg
            1220                1225                1230 gct cct ggt ctc tac tgc gct ggt tac caa ggt gag gac acc ctc ttg    3743
Ala Pro Gly Leu Tyr Cys Ala Gly Tyr Gln Gly Glu Asp Thr Leu Leu
        1235                1240                1245 gtc atg ttc tac aac cag caa gac acc ctt gac tcc tac aag aac gct    3791
Val Met Phe Tyr Asn Gln Gln Asp Thr Leu Asp Ser Tyr Lys Asn Ala
    1250                1255                1260 tcc atg caa ggt ctc tac atc ttc gct gac atg gct tcc aag gac atg    3839
Ser Met Gln Gly Leu Tyr Ile Phe Ala Asp Met Ala Ser Lys Asp Met
1265                1270                1275 act cca gag caa agc aac gtc tac cgt gac aac tcc tac caa cag ttc    3887
Thr Pro Glu Gln Ser Asn Val Tyr Arg Asp Asn Ser Tyr Gln Gln Phe
1280                1285                1290                1295 gac acc aac aac gtc agg cgt gtc aac aac aga tac gct gag gac tac    3935
Asp Thr Asn Asn Val Arg Arg Val Asn Asn Arg Tyr Ala Glu Asp Tyr
```

-continued

|  |  |  |
|---|---|---|
| | 1300 | 1305 | 1310 | gag atc cca agc tct gtc agc tct cgc aag gac tac ggc tgg ggt gac    3983
Glu Ile Pro Ser Ser Val Ser Ser Arg Lys Asp Tyr Gly Trp Gly Asp
            1315                1320                1325 tac tac ctc agc atg gtg tac aac ggt gac atc cca acc atc aac tac    4031
Tyr Tyr Leu Ser Met Val Tyr Asn Gly Asp Ile Pro Thr Ile Asn Tyr
        1330                1335                1340 aag gct gcc tct tcc gac ctc aaa atc tac atc agc cca aag ctc agg    4079
Lys Ala Ala Ser Ser Asp Leu Lys Ile Tyr Ile Ser Pro Lys Leu Arg
    1345                1350                1355 atc atc cac aac ggc tac gag ggt cag aag agg aac cag tgc aac ttg    4127
Ile Ile His Asn Gly Tyr Glu Gly Gln Lys Arg Asn Gln Cys Asn Leu
1360                1365                1370                1375 atg aac aag tac ggc aag ttg ggt gac aag ttc att gtc tac acc tct    4175
Met Asn Lys Tyr Gly Lys Leu Gly Asp Lys Phe Ile Val Tyr Thr Ser
                1380                1385                1390 ctt ggt gtc aac cca aac aac agc tcc aac aag ctc atg ttc tac cca    4223
Leu Gly Val Asn Pro Asn Asn Ser Ser Asn Lys Leu Met Phe Tyr Pro
            1395                1400                1405 gtc tac caa tac tct ggc aac acc tct ggt ctc aac cag ggt aga ctc    4271
Val Tyr Gln Tyr Ser Gly Asn Thr Ser Gly Leu Asn Gln Gly Arg Leu
        1410                1415                1420 ttg ttc cac agg gac acc acc tac cca agc aag gtg gag gct tgg att    4319
Leu Phe His Arg Asp Thr Thr Tyr Pro Ser Lys Val Glu Ala Trp Ile
    1425                1430                1435 cct ggt gcc aag agg tcc ctc acc aac cag aac gct gcc att ggt gat    4367
Pro Gly Ala Lys Arg Ser Leu Thr Asn Gln Asn Ala Ala Ile Gly Asp
1440                1445                1450                1455 gac tac gcc aca gac tcc ctc aac aag cct gat gac ctc aag cag tac    4415
Asp Tyr Ala Thr Asp Ser Leu Asn Lys Pro Asp Asp Leu Lys Gln Tyr
                1460                1465                1470 atc ttc atg act gac tcc aag ggc aca gcc act gat gtc tct ggt cca    4463
Ile Phe Met Thr Asp Ser Lys Gly Thr Ala Thr Asp Val Ser Gly Pro
            1475                1480                1485 gtg gag atc aac act gca atc agc cca gcc aag gtc caa atc att gtc    4511
Val Glu Ile Asn Thr Ala Ile Ser Pro Ala Lys Val Gln Ile Ile Val
        1490                1495                1500 aag gct ggt ggc aag gag caa acc ttc aca gct gac aag gat gtc tcc    4559
Lys Ala Gly Gly Lys Glu Gln Thr Phe Thr Ala Asp Lys Asp Val Ser
    1505                1510                1515 atc cag cca agc cca tcc ttc gat gag atg aac tac caa ttc aac gct    4607
Ile Gln Pro Ser Pro Ser Phe Asp Glu Met Asn Tyr Gln Phe Asn Ala
1520                1525                1530                1535 ctt gag att gat ggt tct ggc ctc aac ttc atc aac aac tct gct tcc    4655
Leu Glu Ile Asp Gly Ser Gly Leu Asn Phe Ile Asn Asn Ser Ala Ser
                1540                1545                1550 att gat gtc acc ttc act gcc ttc gct gag gat ggc cgc aag ttg ggt    4703
Ile Asp Val Thr Phe Thr Ala Phe Ala Glu Asp Gly Arg Lys Leu Gly
            1555                1560                1565 tac gag agc ttc tcc atc cca gtc acc ctt aag gtt tcc act gac aac    4751
Tyr Glu Ser Phe Ser Ile Pro Val Thr Leu Lys Val Ser Thr Asp Asn
        1570                1575                1580 gca ctc acc ctt cat cac aac gag aac ggt gct cag tac atg caa tgg    4799
Ala Leu Thr Leu His His Asn Glu Asn Gly Ala Gln Tyr Met Gln Trp
    1585                1590                1595 caa agc tac cgc acc agg ttg aac acc ctc ttc gca agg caa ctt gtg    4847
Gln Ser Tyr Arg Thr Arg Leu Asn Thr Leu Phe Ala Arg Gln Leu Val
1600                1605                1610                1615 gcc cgt gcc acc aca ggc att gac acc atc ctc agc atg gag acc cag    4895

```
                                                               -continued

Ala Arg Ala Thr Thr Gly Ile Asp Thr Ile Leu Ser Met Glu Thr Gln
            1620                1625                1630 aac atc caa gag cca cag ttg ggc aag ggt ttc tac gcc acc ttc gtc    4943
Asn Ile Gln Glu Pro Gln Leu Gly Lys Gly Phe Tyr Ala Thr Phe Val
            1635                1640                1645 atc cca cct tac aac ctc agc act cat ggt gat gag agg tgg ttc aag    4991
Ile Pro Pro Tyr Asn Leu Ser Thr His Gly Asp Glu Arg Trp Phe Lys
    1650                1655                1660 ctc tac atc aag cac gtg gtt gac aac aac tcc cac atc atc tac tct    5039
Leu Tyr Ile Lys His Val Val Asp Asn Asn Ser His Ile Ile Tyr Ser
        1665                1670                1675 ggt caa ctc act gac acc aac atc aac atc acc ctc ttc atc cca ctt    5087
Gly Gln Leu Thr Asp Thr Asn Ile Asn Ile Thr Leu Phe Ile Pro Leu
1680                1685                1690                1695 gac gat gtc cca ctc aac cag gac tac cat gcc aag gtc tac atg acc    5135
Asp Asp Val Pro Leu Asn Gln Asp Tyr His Ala Lys Val Tyr Met Thr
                1700                1705                1710 ttc aag aag tct cca tct gat ggc acc tgg tgg ggt cca cac ttc gtc    5183
Phe Lys Lys Ser Pro Ser Asp Gly Thr Trp Trp Gly Pro His Phe Val
            1715                1720                1725 cgt gat gac aag ggc atc gtc acc atc aac cca aag tcc atc ctc acc    5231
Arg Asp Asp Lys Gly Ile Val Thr Ile Asn Pro Lys Ser Ile Leu Thr
        1730                1735                1740 cac ttc gag tct gtc aac gtt ctc aac aac atc tcc tct gag cca atg    5279
His Phe Glu Ser Val Asn Val Leu Asn Asn Ile Ser Ser Glu Pro Met
    1745                1750                1755 gac ttc tct ggt gcc aac tcc ctc tac ttc tgg gag ttg ttc tac tac    5327
Asp Phe Ser Gly Ala Asn Ser Leu Tyr Phe Trp Glu Leu Phe Tyr Tyr
1760                1765                1770                1775 aca cca atg ctt gtg gct caa agg ttg ctc cat gag cag aac ttc gat    5375
Thr Pro Met Leu Val Ala Gln Arg Leu Leu His Glu Gln Asn Phe Asp
                1780                1785                1790 gag gcc aac agg tgg ctc aag tac gtc tgg agc cca tct ggt tac att    5423
Glu Ala Asn Arg Trp Leu Lys Tyr Val Trp Ser Pro Ser Gly Tyr Ile
            1795                1800                1805 gtg cat ggt caa atc cag aac tac caa tgg aac gtc agg cca ttg ctt    5471
Val His Gly Gln Ile Gln Asn Tyr Gln Trp Asn Val Arg Pro Leu Leu
        1810                1815                1820 gag gac acc tcc tgg aac tct gac cca ctt gac tct gtg gac cct gat    5519
Glu Asp Thr Ser Trp Asn Ser Asp Pro Leu Asp Ser Val Asp Pro Asp
    1825                1830                1835 gct gtg gct caa cat gac cca atg cac tac aag gtc tcc acc ttc atg    5567
Ala Val Ala Gln His Asp Pro Met His Tyr Lys Val Ser Thr Phe Met
1840                1845                1850                1855 agg acc ttg gac ctc ttg att gcc aga ggt gac cat gct tac cgc caa    5615
Arg Thr Leu Asp Leu Leu Ile Ala Arg Gly Asp His Ala Tyr Arg Gln
                1860                1865                1870 ttg gag agg gac acc ctc aac gag gca aag atg tgg tac atg caa gct    5663
Leu Glu Arg Asp Thr Leu Asn Glu Ala Lys Met Trp Tyr Met Gln Ala
            1875                1880                1885 ctc cac ctc ttg ggt gac aag cca tac ctc cca ctc agc acc act tgg    5711
Leu His Leu Leu Gly Asp Lys Pro Tyr Leu Pro Leu Ser Thr Thr Trp
        1890                1895                1900 tcc gac cca agg ttg gac cgt gct gct gac atc acc act cag aac gct    5759
Ser Asp Pro Arg Leu Asp Arg Ala Ala Asp Ile Thr Thr Gln Asn Ala
    1905                1910                1915 cat gac tct gcc att gtt gct ctc agg cag aac atc cca act cct gct    5807
His Asp Ser Ala Ile Val Ala Leu Arg Gln Asn Ile Pro Thr Pro Ala
1920                1925                1930                1935
```

```
                                              -continued cca ctc tcc ctc aga tct gct aac acc ctc act gac ttg ttc ctc cca    5855
Pro Leu Ser Leu Arg Ser Ala Asn Thr Leu Thr Asp Leu Phe Leu Pro
            1940                1945                1950 cag atc aac gag gtc atg atg aac tac tgg caa acc ttg gct caa agg    5903
Gln Ile Asn Glu Val Met Met Asn Tyr Trp Gln Thr Leu Ala Gln Arg
            1955                1960                1965 gtc tac aac ctc aga cac aac ctc tcc att gat ggt caa cca ctc tac    5951
Val Tyr Asn Leu Arg His Asn Leu Ser Ile Asp Gly Gln Pro Leu Tyr
            1970                1975                1980 ctc cca atc tac gcc aca cca gct gac cca aag gct ctt ctc tct gct    5999
Leu Pro Ile Tyr Ala Thr Pro Ala Asp Pro Lys Ala Leu Leu Ser Ala
            1985                1990                1995 gct gtg gct acc agc caa ggt ggt ggc aag ctc cca gag tcc ttc atg    6047
Ala Val Ala Thr Ser Gln Gly Gly Gly Lys Leu Pro Glu Ser Phe Met
2000            2005                2010                2015 tcc ctc tgg agg ttc cca cac atg ttg gag aac gcc cgt ggc atg gtc    6095
Ser Leu Trp Arg Phe Pro His Met Leu Glu Asn Ala Arg Gly Met Val
                2020                2025                2030 tcc caa ctc acc cag ttc ggt tcc acc ctc cag aac atc att gag agg    6143
Ser Gln Leu Thr Gln Phe Gly Ser Thr Leu Gln Asn Ile Ile Glu Arg
            2035                2040                2045 caa gat gct gag gct ctc aac gct ttg ctc cag aac cag gca gct gag    6191
Gln Asp Ala Glu Ala Leu Asn Ala Leu Leu Gln Asn Gln Ala Ala Glu
            2050                2055                2060 ttg atc ctc acc aac ttg tcc atc caa gac aag acc att gag gag ctt    6239
Leu Ile Leu Thr Asn Leu Ser Ile Gln Asp Lys Thr Ile Glu Glu Leu
            2065                2070                2075 gat gct gag aag aca gtc ctt gag aag agc aag gct ggt gcc caa tct    6287
Asp Ala Glu Lys Thr Val Leu Glu Lys Ser Lys Ala Gly Ala Gln Ser
2080            2085                2090                2095 cgc ttc gac tcc tac ggc aag ctc tac gat gag aac atc aac gct ggt    6335
Arg Phe Asp Ser Tyr Gly Lys Leu Tyr Asp Glu Asn Ile Asn Ala Gly
                2100                2105                2110 gag aac cag gcc atg acc ctc agg gct tcc gca gct ggt ctc acc act    6383
Glu Asn Gln Ala Met Thr Leu Arg Ala Ser Ala Ala Gly Leu Thr Thr
            2115                2120                2125 gct gtc caa gcc tct cgc ttg gct ggt gca gct gct gac ctc gtt cca    6431
Ala Val Gln Ala Ser Arg Leu Ala Gly Ala Ala Ala Asp Leu Val Pro
            2130                2135                2140 aac atc ttc ggt ttc gct ggt ggt ggc tcc aga tgg ggt gcc att gct    6479
Asn Ile Phe Gly Phe Ala Gly Gly Gly Ser Arg Trp Gly Ala Ile Ala
            2145                2150                2155 gag gct acc ggt tac gtc atg gag ttc tct gcc aac gtc atg aac act    6527
Glu Ala Thr Gly Tyr Val Met Glu Phe Ser Ala Asn Val Met Asn Thr
2160            2165                2170                2175 gag gct gac aag atc agc caa tct gag acc tac aga agg cgc cgt caa    6575
Glu Ala Asp Lys Ile Ser Gln Ser Glu Thr Tyr Arg Arg Arg Arg Gln
                2180                2185                2190 gag tgg gag atc caa agg aac aac gct gag gca gag ttg aag caa atc    6623
Glu Trp Glu Ile Gln Arg Asn Asn Ala Glu Ala Glu Leu Lys Gln Ile
            2195                2200                2205 gat gct caa ctc aag tcc ttg gct gtc aga agg gag gct gct gtc ctc    6671
Asp Ala Gln Leu Lys Ser Leu Ala Val Arg Arg Glu Ala Ala Val Leu
            2210                2215                2220 cag aag acc tcc ctc aag acc caa cag gag caa acc cag tcc cag ttg    6719
Gln Lys Thr Ser Leu Lys Thr Gln Gln Glu Gln Thr Gln Ser Gln Leu
            2225                2230                2235 gct ttc ctc caa agg aag ttc tcc aac cag gct ctc tac aac tgg ctc    6767
Ala Phe Leu Gln Arg Lys Phe Ser Asn Gln Ala Leu Tyr Asn Trp Leu
2240            2245                2250                2255
```

```
aga ggc cgc ttg gct gcc atc tac ttc caa ttc tac gac ctt gct gtg      6815
Arg Gly Arg Leu Ala Ala Ile Tyr Phe Gln Phe Tyr Asp Leu Ala Val
                2260                2265                2270 gcc agg tgc ctc atg gct gag caa gcc tac cgc tgg gag ttg aac gat      6863
Ala Arg Cys Leu Met Ala Glu Gln Ala Tyr Arg Trp Glu Leu Asn Asp
            2275                2280                2285 gac tcc gcc agg ttc atc aag cca ggt gct tgg caa ggc acc tac gct      6911
Asp Ser Ala Arg Phe Ile Lys Pro Gly Ala Trp Gln Gly Thr Tyr Ala
        2290                2295                2300 ggt ctc ctt gct ggt gag acc ctc atg ctc tcc ttg gct caa atg gag      6959
Gly Leu Leu Ala Gly Glu Thr Leu Met Leu Ser Leu Ala Gln Met Glu
    2305                2310                2315 gat gct cac ctc aag agg gac aag agg gct ttg gag gtg gag agg aca      7007
Asp Ala His Leu Lys Arg Asp Lys Arg Ala Leu Glu Val Glu Arg Thr
2320                2325                2330                2335 gtc tcc ctt gct gag gtc tac gct ggt ctc cca aag gac aac ggt cca      7055
Val Ser Leu Ala Glu Val Tyr Ala Gly Leu Pro Lys Asp Asn Gly Pro
                2340                2345                2350 ttc tcc ctt gct caa gag att gac aag ttg gtc agc caa ggt tct ggt      7103
Phe Ser Leu Ala Gln Glu Ile Asp Lys Leu Val Ser Gln Gly Ser Gly
            2355                2360                2365 tct gct ggt tct ggt aac aac aac ttg gct ttc ggc gct ggt act gac      7151
Ser Ala Gly Ser Gly Asn Asn Asn Leu Ala Phe Gly Ala Gly Thr Asp
        2370                2375                2380 acc aag acc tcc ctc caa gcc tct gtc tcc ttc gct gac ctc aag atc      7199
Thr Lys Thr Ser Leu Gln Ala Ser Val Ser Phe Ala Asp Leu Lys Ile
    2385                2390                2395 agg gag gac tac cca gct tcc ctt ggc aag atc agg cgc atc aag caa      7247
Arg Glu Asp Tyr Pro Ala Ser Leu Gly Lys Ile Arg Arg Ile Lys Gln
2400                2405                2410                2415 atc tct gtc acc ctc cca gct ctc ttg ggt cca tac caa gat gtc caa      7295
Ile Ser Val Thr Leu Pro Ala Leu Leu Gly Pro Tyr Gln Asp Val Gln
                2420                2425                2430 gca atc ctc tcc tac ggt gac aag gct ggt ttg gcg aac ggt tgc gag      7343
Ala Ile Leu Ser Tyr Gly Asp Lys Ala Gly Leu Ala Asn Gly Cys Glu
            2435                2440                2445 gct ctt gct gtc tct cat ggc atg aac gac tct ggt caa ttc caa ctt      7391
Ala Leu Ala Val Ser His Gly Met Asn Asp Ser Gly Gln Phe Gln Leu
        2450                2455                2460 gac ttc aac gat ggc aag ttc ctc cca ttc gag ggc att gcc att gac      7439
Asp Phe Asn Asp Gly Lys Phe Leu Pro Phe Glu Gly Ile Ala Ile Asp
    2465                2470                2475 caa ggc acc ctc acc ctc tcc ttc cca aac gct tcc atg cca gag aag      7487
Gln Gly Thr Leu Thr Leu Ser Phe Pro Asn Ala Ser Met Pro Glu Lys
2480                2485                2490                2495 gga aag caa gcc acc atg ctc aag acc ctc aac gat atc atc ctc cac      7535
Gly Lys Gln Ala Thr Met Leu Lys Thr Leu Asn Asp Ile Ile Leu His
                2500                2505                2510 atc agg tac acc atc aag tgagctcgag aggcctgcgg ccgc                   7577
Ile Arg Tyr Thr Ile Lys
            2515

<210> SEQ ID NO 4
<211> LENGTH: 7541
<212> TYPE: DNA
<213> ORGANISM: Artificial Sequence
<220> FEATURE:
<221> NAME/KEY: CDS
<222> LOCATION: (3)..(7517)
<220> FEATURE:
<223> OTHER INFORMATION: Description of Artificial Sequence:hemicot tcbA
```

-continued

<400> SEQUENCE: 4

```
cc atg gct cag aac tcc ctc agc tcc acc att gac acc atc tgc cag         47
   Met Ala Gln Asn Ser Leu Ser Ser Thr Ile Asp Thr Ile Cys Gln
   1               5                   10                  15 aag ctt caa ctc acc tgc cca gct gag atc gcc ctc tac cca ttc gac        95
Lys Leu Gln Leu Thr Cys Pro Ala Glu Ile Ala Leu Tyr Pro Phe Asp
            20                  25                  30 acc ttc cgt gag aag acc aga ggc atg gtc aac tgg ggt gag gcc aag       143
Thr Phe Arg Glu Lys Thr Arg Gly Met Val Asn Trp Gly Glu Ala Lys
        35                  40                  45 agg atc tac gag att gct caa gct gag caa gac agg aac ctc ctt cat       191
Arg Ile Tyr Glu Ile Ala Gln Ala Glu Gln Asp Arg Asn Leu Leu His
            50                  55                  60 gag aag agg atc ttc gcc tac gct aac cca ttg ctc aag aac gct gtc       239
Glu Lys Arg Ile Phe Ala Tyr Ala Asn Pro Leu Leu Lys Asn Ala Val
65                  70                  75 agg ctt ggt acc agg caa atg ttg ggt ttc atc caa ggt tac tct gac       287
Arg Leu Gly Thr Arg Gln Met Leu Gly Phe Ile Gln Gly Tyr Ser Asp
        80                  85                  90              95 ttg ttc ggc aac agg gct gac aac tac gca gct cct ggt tct gtt gct       335
Leu Phe Gly Asn Arg Ala Asp Asn Tyr Ala Ala Pro Gly Ser Val Ala
                100                 105                 110 agc atg ttc agc cca gct gcc tac ctc act gag ttg tac cgt gag gcc       383
Ser Met Phe Ser Pro Ala Ala Tyr Leu Thr Glu Leu Tyr Arg Glu Ala
            115                 120                 125 aag aac ctc cat gac agc tcc agc atc tac tac ctt gac aag agg cgc       431
Lys Asn Leu His Asp Ser Ser Ser Ile Tyr Tyr Leu Asp Lys Arg Arg
        130                 135                 140 cca gac ctt gct tcc ttg atg ctc tcc cag aag aac atg gat gag gag       479
Pro Asp Leu Ala Ser Leu Met Leu Ser Gln Lys Asn Met Asp Glu Glu
    145                 150                 155 atc agc acc ttg gct ctc tcc aac gag ctt tgc ttg gct ggc att gag       527
Ile Ser Thr Leu Ala Leu Ser Asn Glu Leu Cys Leu Ala Gly Ile Glu
160                 165                 170                 175 acc aag act ggc aag tcc caa gat gag gtc atg gac atg ctc tcc acc       575
Thr Lys Thr Gly Lys Ser Gln Asp Glu Val Met Asp Met Leu Ser Thr
                180                 185                 190 tac cgc ctc tct ggt gag act cca tac cac cat gct tac gag act gtc       623
Tyr Arg Leu Ser Gly Glu Thr Pro Tyr His His Ala Tyr Glu Thr Val
            195                 200                 205 agg gag att gtc cat gag agg gac cca ggt ttc cgc cac ctc tcc caa       671
Arg Glu Ile Val His Glu Arg Asp Pro Gly Phe Arg His Leu Ser Gln
        210                 215                 220 gct ccc att gtg gct gcc aag ttg gac cca gtc acc ctc ttg ggc atc       719
Ala Pro Ile Val Ala Ala Lys Leu Asp Pro Val Thr Leu Leu Gly Ile
225                 230                 235 tcc agc cac atc agc cca gag ttg tac aac ctt ctc att gag gag atc       767
Ser Ser His Ile Ser Pro Glu Leu Tyr Asn Leu Leu Ile Glu Glu Ile
240                 245                 250                 255 cca gag aag gat gag gca gct ttg gac acc ctc tac aag acc aac ttc       815
Pro Glu Lys Asp Glu Ala Ala Leu Asp Thr Leu Tyr Lys Thr Asn Phe
                260                 265                 270 ggt gac atc acc act gct caa ctc atg agc cca tcc tac ttg gcc agg       863
Gly Asp Ile Thr Thr Ala Gln Leu Met Ser Pro Ser Tyr Leu Ala Arg
            275                 280                 285 tac tac ggt gtc tct cca gag gac att gct tac gtc acc aca agc ctc       911
Tyr Tyr Gly Val Ser Pro Glu Asp Ile Ala Tyr Val Thr Thr Ser Leu
        290                 295                 300
```

-continued

| | |
|---|---|
| tcc cat gtg ggt tac tcc tct gac atc ctt gtc atc cca ctc gtg gat<br>Ser His Val Gly Tyr Ser Ser Asp Ile Leu Val Ile Pro Leu Val Asp<br>305                        310                      315 | 959 |
| ggt gtg ggc aag atg gag gtt gtc agg gtc acc agg act cca tct gac<br>Gly Val Gly Lys Met Glu Val Val Arg Val Thr Arg Thr Pro Ser Asp<br>320                        325                      330                      335 | 1007 |
| aac tac acc tcc cag acc aac tac att gag ttg tac cca caa ggt ggt<br>Asn Tyr Thr Ser Gln Thr Asn Tyr Ile Glu Leu Tyr Pro Gln Gly Gly<br>                      340                      345                      350 | 1055 |
| gac aac tac ctc atc aag tac aac ctc tcc aac tct ttc ggt ttg gat<br>Asp Asn Tyr Leu Ile Lys Tyr Asn Leu Ser Asn Ser Phe Gly Leu Asp<br>                355                      360                      365 | 1103 |
| gac ttc tac ctc cag tac aag gat ggt tct gct gac tgg act gag att<br>Asp Phe Tyr Leu Gln Tyr Lys Asp Gly Ser Ala Asp Trp Thr Glu Ile<br>      370                      375                      380 | 1151 |
| gct cac aac cca tac cca gac atg gtc atc aac cag aag tac gag tcc<br>Ala His Asn Pro Tyr Pro Asp Met Val Ile Asn Gln Lys Tyr Glu Ser<br>385                        390                      395 | 1199 |
| caa gcc acc atc aag aga tct gac tct gac aac atc ctc tcc att ggt<br>Gln Ala Thr Ile Lys Arg Ser Asp Ser Asp Asn Ile Leu Ser Ile Gly<br>400                        405                      410                      415 | 1247 |
| ctc caa agg tgg cac tct ggt tcc tac aac ttc gct gct gcc aac ttc<br>Leu Gln Arg Trp His Ser Gly Ser Tyr Asn Phe Ala Ala Ala Asn Phe<br>                      420                      425                      430 | 1295 |
| aag att gac caa tac tct cca aag gct ttc ctc ttg aag atg aac aag<br>Lys Ile Asp Gln Tyr Ser Pro Lys Ala Phe Leu Leu Lys Met Asn Lys<br>                435                      440                      445 | 1343 |
| gcc atc agg ctc ttg aag gcc act ggt ctc tcc ttc gcc acc ctt gag<br>Ala Ile Arg Leu Leu Lys Ala Thr Gly Leu Ser Phe Ala Thr Leu Glu<br>      450                      455                      460 | 1391 |
| agg att gtg gac tct gtc aac tcc acc aag tcc atc act gtg gag gtc<br>Arg Ile Val Asp Ser Val Asn Ser Thr Lys Ser Ile Thr Val Glu Val<br>465                        470                      475 | 1439 |
| ctc aac aag gtc tac aga gtc aag ttc tac att gac cgc tac ggc atc<br>Leu Asn Lys Val Tyr Arg Val Lys Phe Tyr Ile Asp Arg Tyr Gly Ile<br>480                        485                      490                      495 | 1487 |
| tct gag gag act gct gcc atc ctt gcc aac atc aac atc tcc cag caa<br>Ser Glu Glu Thr Ala Ala Ile Leu Ala Asn Ile Asn Ile Ser Gln Gln<br>                      500                      505                      510 | 1535 |
| gct gtc ggc aac cag ctc tcc caa ttc gag caa ctc ttc aac cac cct<br>Ala Val Gly Asn Gln Leu Ser Gln Phe Glu Gln Leu Phe Asn His Pro<br>                515                      520                      525 | 1583 |
| cca ctc aac ggc atc cgc tac gag atc agc gag gac aac tcc aag cac<br>Pro Leu Asn Gly Ile Arg Tyr Glu Ile Ser Glu Asp Asn Ser Lys His<br>      530                      535                      540 | 1631 |
| ctc cca aac cca gac ctc aac ctc aag cca gac tcc act ggt gat gac<br>Leu Pro Asn Pro Asp Leu Asn Leu Lys Pro Asp Ser Thr Gly Asp Asp<br>545                        550                      555 | 1679 |
| caa agg aag gct gtc ctc aag agg gct ttc caa gtc aac gct tct gag<br>Gln Arg Lys Ala Val Leu Lys Arg Ala Phe Gln Val Asn Ala Ser Glu<br>560                        565                      570                      575 | 1727 |
| ctt tac caa atg ctc ttg atc act gac agg aag gag gat ggt gtc atc<br>Leu Tyr Gln Met Leu Leu Ile Thr Asp Arg Lys Glu Asp Gly Val Ile<br>                      580                      585                      590 | 1775 |
| aag aac aac ttg gag aac ctc tct gac ctc tac ctt gtc tcc ctc ttg<br>Lys Asn Asn Leu Glu Asn Leu Ser Asp Leu Tyr Leu Val Ser Leu Leu<br>                595                      600                      605 | 1823 |
| gcc caa atc cac aac ttg acc att gct gag ttg aac atc ctc ttg gtc<br>Ala Gln Ile His Asn Leu Thr Ile Ala Glu Leu Asn Ile Leu Leu Val<br>      610                      615                      620 | 1871 |

```
atc tgc ggt tac ggt gac acc aac atc tac caa atc act gac gac aac       1919
Ile Cys Gly Tyr Gly Asp Thr Asn Ile Tyr Gln Ile Thr Asp Asp Asn
        625                 630                 635 ctt gcc aag att gtg gag acc ctc ttg tgg atc acc caa tgg ctc aag       1967
Leu Ala Lys Ile Val Glu Thr Leu Leu Trp Ile Thr Gln Trp Leu Lys
640                 645                 650                 655 acc cag aag tgg act gtc aca gac ctc ttc ctc atg acc act gcc acc       2015
Thr Gln Lys Trp Thr Val Thr Asp Leu Phe Leu Met Thr Thr Ala Thr
                660                 665                 670 tac tcc acc act ctc act cca gag att tcc aac ctc act gcc acc ctc       2063
Tyr Ser Thr Thr Leu Thr Pro Glu Ile Ser Asn Leu Thr Ala Thr Leu
                675                 680                 685 agc tcc acc ctc cac ggc aag gag tcc ctc att ggt gag gac ctc aag       2111
Ser Ser Thr Leu His Gly Lys Glu Ser Leu Ile Gly Glu Asp Leu Lys
                690                 695                 700 agg gca atg gct cca tgc ttc acc tct gct ctc cac ctc acc tcc caa       2159
Arg Ala Met Ala Pro Cys Phe Thr Ser Ala Leu His Leu Thr Ser Gln
        705                 710                 715 gag gtg gct tac gac ctc ctt ctc tgg att gac caa atc caa cca gct       2207
Glu Val Ala Tyr Asp Leu Leu Leu Trp Ile Asp Gln Ile Gln Pro Ala
720                 725                 730                 735 caa atc act gtg gat ggt ttc tgg gag gag gtc caa acc act cca acc       2255
Gln Ile Thr Val Asp Gly Phe Trp Glu Glu Val Gln Thr Thr Pro Thr
                740                 745                 750 tcc ctc aag gtc atc acc ttc gct caa gtc ttg gct caa ctc tcc ctc       2303
Ser Leu Lys Val Ile Thr Phe Ala Gln Val Leu Ala Gln Leu Ser Leu
                755                 760                 765 atc tac aga agg att ggt ctc tct gag act gag ttg tcc ctc att gtc       2351
Ile Tyr Arg Arg Ile Gly Leu Ser Glu Thr Glu Leu Ser Leu Ile Val
        770                 775                 780 acc caa tcc agc ctc ttg gtc gct ggc aag tcc atc ctt gat cat ggt       2399
Thr Gln Ser Ser Leu Leu Val Ala Gly Lys Ser Ile Leu Asp His Gly
785                 790                 795 ctc ttg acc ctc atg gct ctt gag ggt ttc cac acc tgg gtc aac ggt       2447
Leu Leu Thr Leu Met Ala Leu Glu Gly Phe His Thr Trp Val Asn Gly
800                 805                 810                 815 ttg ggt caa cat gct tcc ctc atc ttg gct gca ctc aag gat ggt gct       2495
Leu Gly Gln His Ala Ser Leu Ile Leu Ala Ala Leu Lys Asp Gly Ala
                820                 825                 830 ctc acc gtc acc gat gtg gct caa gcc atg aac aag gag gag tcc ctc       2543
Leu Thr Val Thr Asp Val Ala Gln Ala Met Asn Lys Glu Glu Ser Leu
                835                 840                 845 ttg caa atg gct gcc aac cag gtg gag aag gac ctc acc aag ctc acc       2591
Leu Gln Met Ala Ala Asn Gln Val Glu Lys Asp Leu Thr Lys Leu Thr
        850                 855                 860 tcc tgg acc caa atc gat gcc atc ctc caa tgg ctc caa atg tcc tct       2639
Ser Trp Thr Gln Ile Asp Ala Ile Leu Gln Trp Leu Gln Met Ser Ser
865                 870                 875 gct ctt gct gtc agc cca ttg gac ctt gct ggc atg atg gct ctc aag       2687
Ala Leu Ala Val Ser Pro Leu Asp Leu Ala Gly Met Met Ala Leu Lys
880                 885                 890                 895 tac ggc att gat cac aac tac gct gcc tgg caa gca gct gcc gct gcc       2735
Tyr Gly Ile Asp His Asn Tyr Ala Ala Trp Gln Ala Ala Ala Ala Ala
                900                 905                 910 ctc atg gct gac cat gcc aac cag gct cag aag aag ttg gat gag acc       2783
Leu Met Ala Asp His Ala Asn Gln Ala Gln Lys Lys Leu Asp Glu Thr
                915                 920                 925 ttc tcc aag gct ctc tgc aac tac tac atc aac gcc gtg gtt gac tct       2831
Phe Ser Lys Ala Leu Cys Asn Tyr Tyr Ile Asn Ala Val Val Asp Ser
```

-continued

```
              930                 935                 940
gct gcc ggt gtc agg gac agg aac ggt ctc tac acc tac ctc ttg att    2879
Ala Ala Gly Val Arg Asp Arg Asn Gly Leu Tyr Thr Tyr Leu Leu Ile
    945                 950                 955 gac aac cag gtc tct gct gat gtc atc acc tcc aga att gct gag gcc    2927
Asp Asn Gln Val Ser Ala Asp Val Ile Thr Ser Arg Ile Ala Glu Ala
960                 965                 970                 975 att gct ggc atc caa ctc tac gtc aac agg gct ctc aac agg gat gag    2975
Ile Ala Gly Ile Gln Leu Tyr Val Asn Arg Ala Leu Asn Arg Asp Glu
                980                 985                 990 ggt cag ttg gct tct gat gtc tcc acc agg caa ttc ttc acc gac tgg    3023
Gly Gln Leu Ala Ser Asp Val Ser Thr Arg Gln Phe Phe Thr Asp Trp
            995                 1000                1005 gag agg tac aac aag agg tac tcc acc tgg gct ggt gtc tct gag ttg    3071
Glu Arg Tyr Asn Lys Arg Tyr Ser Thr Trp Ala Gly Val Ser Glu Leu
        1010                1015                1020 gtc tac tac cca gag aac tac gtg gac cca acc caa agg att ggt cag    3119
Val Tyr Tyr Pro Glu Asn Tyr Val Asp Pro Thr Gln Arg Ile Gly Gln
    1025                1030                1035 acc aag atg atg gat gct ttg ctc caa tcc atc aac cag tcc caa ctc    3167
Thr Lys Met Met Asp Ala Leu Leu Gln Ser Ile Asn Gln Ser Gln Leu
1040                1045                1050                1055 aac gct gac act gtg gag gat gct ttc aag acc tac ctc acc tcc ttc    3215
Asn Ala Asp Thr Val Glu Asp Ala Phe Lys Thr Tyr Leu Thr Ser Phe
                1060                1065                1070 gag caa gtg gcc aac ctc aag gtc atc tct gct tac cat gac aac gtc    3263
Glu Gln Val Ala Asn Leu Lys Val Ile Ser Ala Tyr His Asp Asn Val
            1075                1080                1085 aac gtg gac caa ggt ctc acc tac ttc att ggc att gac caa gcc gct    3311
Asn Val Asp Gln Gly Leu Thr Tyr Phe Ile Gly Ile Asp Gln Ala Ala
        1090                1095                1100 cct ggc acc tac tac tgg agg tct gtg gac cac tcc aag tgc gag aac    3359
Pro Gly Thr Tyr Tyr Trp Arg Ser Val Asp His Ser Lys Cys Glu Asn
    1105                1110                1115 ggc aag ttc gct gcc aac gct tgg ggt gag tgg aac aag atc acc tgc    3407
Gly Lys Phe Ala Ala Asn Ala Trp Gly Glu Trp Asn Lys Ile Thr Cys
1120                1125                1130                1135 gct gtc aac cct tgg aag aac atc atc agg cca gtg gtc tac atg tcc    3455
Ala Val Asn Pro Trp Lys Asn Ile Ile Arg Pro Val Val Tyr Met Ser
                1140                1145                1150 aga ctc tac ttg ctc tgg ctt gag caa cag tcc aag aag tct gat gac    3503
Arg Leu Tyr Leu Leu Trp Leu Glu Gln Gln Ser Lys Lys Ser Asp Asp
            1155                1160                1165 ggc aag aca act atc tac cag tac aac ctc aag ttg gct cac atc cgc    3551
Gly Lys Thr Thr Ile Tyr Gln Tyr Asn Leu Lys Leu Ala His Ile Arg
        1170                1175                1180 tac gat ggt tcc tgg aac act cca ttc acc ttc gat gtc act gag aag    3599
Tyr Asp Gly Ser Trp Asn Thr Pro Phe Thr Phe Asp Val Thr Glu Lys
    1185                1190                1195 gtc aag aac tac acc tcc agc act gat gca gct gag tcc ctt ggt ctc    3647
Val Lys Asn Tyr Thr Ser Ser Thr Asp Ala Ala Glu Ser Leu Gly Leu
1200                1205                1210                1215 tac tgc act ggt tac caa ggt gag gac acc ctc ttg gtc atg ttc tac    3695
Tyr Cys Thr Gly Tyr Gln Gly Glu Asp Thr Leu Leu Val Met Phe Tyr
                1220                1225                1230 tcc atg caa tcc agc tac tcc agc tac act gac aac aac gct cca gtc    3743
Ser Met Gln Ser Ser Tyr Ser Ser Tyr Thr Asp Asn Asn Ala Pro Val
            1235                1240                1245 act ggt ctc tac atc ttc gct gac atg tcc tct gac aac atg acc aac    3791
```

```
                                                              -continued

Thr Gly Leu Tyr Ile Phe Ala Asp Met Ser Ser Asp Asn Met Thr Asn
        1250                1255                1260 gct caa gcc acc aac tac tgg aac aac tcc tac cca caa ttc gac act        3839
Ala Gln Ala Thr Asn Tyr Trp Asn Asn Ser Tyr Pro Gln Phe Asp Thr
    1265                1270                1275 gtc atg gct gac cca gac tct gac aac aag aag gtc atc acc agg cgt        3887
Val Met Ala Asp Pro Asp Ser Asp Asn Lys Lys Val Ile Thr Arg Arg
1280                1285                1290                1295 gtc aac aac cgc tac gct gag gac tac gag atc cca agc tct gtc acc        3935
Val Asn Asn Arg Tyr Ala Glu Asp Tyr Glu Ile Pro Ser Ser Val Thr
                1300                1305                1310 tcc aac agc aac tac tcc tgg ggt gac cac tcc ctc acc atg ctc tac        3983
Ser Asn Ser Asn Tyr Ser Trp Gly Asp His Ser Leu Thr Met Leu Tyr
            1315                1320                1325 ggt ggc tct gtc cca aac atc acc ttc gag tct gca gct gag gac ctc        4031
Gly Gly Ser Val Pro Asn Ile Thr Phe Glu Ser Ala Ala Glu Asp Leu
        1330                1335                1340 agg ctc tcc acc aac atg gct ctc tcc atc att cac aac ggt tac gct        4079
Arg Leu Ser Thr Asn Met Ala Leu Ser Ile Ile His Asn Gly Tyr Ala
    1345                1350                1355 ggc acc agg cgc atc caa tgc aac ctc atg aag caa tac gct tcc ctt        4127
Gly Thr Arg Arg Ile Gln Cys Asn Leu Met Lys Gln Tyr Ala Ser Leu
1360                1365                1370                1375 ggt gac aag ttc att atc tac gac tcc agc ttc gat gac gcc aac agg        4175
Gly Asp Lys Phe Ile Ile Tyr Asp Ser Ser Phe Asp Asp Ala Asn Arg
                1380                1385                1390 ttc aac ttg gtc cca ctc ttc aag ttc ggc aag gat gag aac tct gat        4223
Phe Asn Leu Val Pro Leu Phe Lys Phe Gly Lys Asp Glu Asn Ser Asp
            1395                1400                1405 gac tcc atc tgc atc tac aac gag aac cca agc tct gag gac aag aag        4271
Asp Ser Ile Cys Ile Tyr Asn Glu Asn Pro Ser Ser Glu Asp Lys Lys
        1410                1415                1420 tgg tac ttc agc tcc aag gac gac aac aag act gct gac tac aac ggt        4319
Trp Tyr Phe Ser Ser Lys Asp Asp Asn Lys Thr Ala Asp Tyr Asn Gly
    1425                1430                1435 ggc acc caa tgc att gat gct ggc acc tcc aac aag gac ttc tac tac        4367
Gly Thr Gln Cys Ile Asp Ala Gly Thr Ser Asn Lys Asp Phe Tyr Tyr
1440                1445                1450                1455 aac ctc caa gag att gag gtc atc tct gtc act ggt ggc tac tgg tcc        4415
Asn Leu Gln Glu Ile Glu Val Ile Ser Val Thr Gly Gly Tyr Trp Ser
                1460                1465                1470 agc tac aag atc agc aac ccc atc aac atc aac act ggc att gac tct        4463
Ser Tyr Lys Ile Ser Asn Pro Ile Asn Ile Asn Thr Gly Ile Asp Ser
            1475                1480                1485 gcc aag gtc aag gtc act gtc aag gct ggt ggc gat gac caa atc ttc        4511
Ala Lys Val Lys Val Thr Val Lys Ala Gly Gly Asp Asp Gln Ile Phe
        1490                1495                1500 act gct gac aac tcc acc tac gtc cca cag caa cct gct cca tcc ttc        4559
Thr Ala Asp Asn Ser Thr Tyr Val Pro Gln Gln Pro Ala Pro Ser Phe
    1505                1510                1515 gag gag atg atc tac caa ttc aac aac ctc acc att gac tgc aag aac        4607
Glu Glu Met Ile Tyr Gln Phe Asn Asn Leu Thr Ile Asp Cys Lys Asn
1520                1525                1530                1535 ctc aac ttc att gac aac cag gct cac att gag att gac ttc act gcc        4655
Leu Asn Phe Ile Asp Asn Gln Ala His Ile Glu Ile Asp Phe Thr Ala
                1540                1545                1550 aca gct caa gat ggc cgc ttc ttg ggt gct gag acc ttc atc att cca        4703
Thr Ala Gln Asp Gly Arg Phe Leu Gly Ala Glu Thr Phe Ile Ile Pro
            1555                1560                1565
```

```
                                                        -continued gtc acc aag aag gtc ctt ggc act gag aac gtc att gct ctc tac tct    4751
Val Thr Lys Lys Val Leu Gly Thr Glu Asn Val Ile Ala Leu Tyr Ser
    1570                1575                1580 gag aac aac ggt gtc cag tac atg caa att ggt gct tac aga acc agg    4799
Glu Asn Asn Gly Val Gln Tyr Met Gln Ile Gly Ala Tyr Arg Thr Arg
1585                1590                1595 ctc aac acc ctc ttc gct caa cag ttg gtc tcc cgt gcc aac aga ggc    4847
Leu Asn Thr Leu Phe Ala Gln Gln Leu Val Ser Arg Ala Asn Arg Gly
1600                1605                1610                1615 att gat gct gtc ctc agc atg gag act cag aac atc caa gag cca caa    4895
Ile Asp Ala Val Leu Ser Met Glu Thr Gln Asn Ile Gln Glu Pro Gln
            1620                1625                1630 ctt ggt gct ggc acc tac gtc caa ctt gtc ttg gac aag tac gat gag    4943
Leu Gly Ala Gly Thr Tyr Val Gln Leu Val Leu Asp Lys Tyr Asp Glu
        1635                1640                1645 tcc att cat ggc acc aac aag tcc ttc gcc att gag tac gtg gac atc    4991
Ser Ile His Gly Thr Asn Lys Ser Phe Ala Ile Glu Tyr Val Asp Ile
    1650                1655                1660 ttc aag gag aac gac tcc ttc gtc atc tac caa ggt gag ttg tct gag    5039
Phe Lys Glu Asn Asp Ser Phe Val Ile Tyr Gln Gly Glu Leu Ser Glu
1665                1670                1675 acc tcc caa act gtg gtc aag gtc ttc ctc tcc tac ttc att gag gcc    5087
Thr Ser Gln Thr Val Val Lys Val Phe Leu Ser Tyr Phe Ile Glu Ala
1680                1685                1690                1695 acc ggt aac aag aac cac ctc tgg gtc agg gcc aag tac cag aag gag    5135
Thr Gly Asn Lys Asn His Leu Trp Val Arg Ala Lys Tyr Gln Lys Glu
            1700                1705                1710 acc act gac aag atc ctc ttc gac agg act gat gag aag gac cca cat    5183
Thr Thr Asp Lys Ile Leu Phe Asp Arg Thr Asp Glu Lys Asp Pro His
        1715                1720                1725 ggt tgg ttc ctc tct gat gac cac aag acc ttc tct ggt ctc agc tct    5231
Gly Trp Phe Leu Ser Asp Asp His Lys Thr Phe Ser Gly Leu Ser Ser
    1730                1735                1740 gct caa gct ctc aag aac gac tct gag cca atg gac ttc tct ggt gcc    5279
Ala Gln Ala Leu Lys Asn Asp Ser Glu Pro Met Asp Phe Ser Gly Ala
1745                1750                1755 aac gct ctc tac ttc tgg gag ttg ttc tac tac act cca atg atg atg    5327
Asn Ala Leu Tyr Phe Trp Glu Leu Phe Tyr Tyr Thr Pro Met Met Met
1760                1765                1770                1775 gct cac agg ctc ctt caa gag cag aac ttc gat gct gcc aac cac tgg    5375
Ala His Arg Leu Leu Gln Glu Gln Asn Phe Asp Ala Ala Asn His Trp
            1780                1785                1790 ttc cgc tac gtc tgg agc cca tct ggt tac att gtg gat ggc aag att    5423
Phe Arg Tyr Val Trp Ser Pro Ser Gly Tyr Ile Val Asp Gly Lys Ile
        1795                1800                1805 gcc atc tac cac tgg aac gtc agg cca ttg gag gag gac acc tcc tgg    5471
Ala Ile Tyr His Trp Asn Val Arg Pro Leu Glu Glu Asp Thr Ser Trp
    1810                1815                1820 aac gct cag caa ctt gac tcc act gac cca gat gct gtg gct caa gat    5519
Asn Ala Gln Gln Leu Asp Ser Thr Asp Pro Asp Ala Val Ala Gln Asp
1825                1830                1835 gac cca atg cac tac aag gtg gcc acc ttc atg gcc acc ttg gac ctt    5567
Asp Pro Met His Tyr Lys Val Ala Thr Phe Met Ala Thr Leu Asp Leu
1840                1845                1850                1855 ctc atg gcc aga ggt gat gct gcc tac cgc caa ttg gag agg gac acc    5615
Leu Met Ala Arg Gly Asp Ala Ala Tyr Arg Gln Leu Glu Arg Asp Thr
            1860                1865                1870 ttg gct gag gcc aag atg tgg tac acc caa gct ctc aac ttg ctg ggt    5663
Leu Ala Glu Ala Lys Met Trp Tyr Thr Gln Ala Leu Asn Leu Leu Gly
        1875                1880                1885
```

```
gat gag cca caa gtc atg ctc tcc aca acc tgg gcc aac cca acc ttg    5711
Asp Glu Pro Gln Val Met Leu Ser Thr Thr Trp Ala Asn Pro Thr Leu
        1890                1895                1900 ggc aac gct gcc tcc aag acc aca caa cag gtc agg caa cag gtc ctc    5759
Gly Asn Ala Ala Ser Lys Thr Thr Gln Gln Val Arg Gln Gln Val Leu
1905                1910                1915 acc caa ctc agg ctc aac tct aga gtc aag act cca ctc ttg ggc act    5807
Thr Gln Leu Arg Leu Asn Ser Arg Val Lys Thr Pro Leu Leu Gly Thr
1920                1925                1930                1935 gcc aac tcc ctc act gct ctc ttc ctc cca caa gag aac tcc aaa ctt    5855
Ala Asn Ser Leu Thr Ala Leu Phe Leu Pro Gln Glu Asn Ser Lys Leu
        1940                1945                1950 aag ggt tac tgg agg acc ctt gct caa cgc atg ttc aac ctc agg cac    5903
Lys Gly Tyr Trp Arg Thr Leu Ala Gln Arg Met Phe Asn Leu Arg His
        1955                1960                1965 aac ctc tcc att gat ggt caa cca ctc tcc ttg cca ctc tac gct aag    5951
Asn Leu Ser Ile Asp Gly Gln Pro Leu Ser Leu Pro Leu Tyr Ala Lys
        1970                1975                1980 cca gct gac cca aag gct ctc ctt tcc gct gct gtc tcc gca tcc caa    5999
Pro Ala Asp Pro Lys Ala Leu Leu Ser Ala Ala Val Ser Ala Ser Gln
1985                1990                1995 ggt ggt gct gac ctc cca aag gct cca ctc acc atc cac agg ttc cca    6047
Gly Gly Ala Asp Leu Pro Lys Ala Pro Leu Thr Ile His Arg Phe Pro
2000                2005                2010                2015 caa atg ttg gag ggt gcc cgt ggt ctt gtc aac cag ctc atc caa ttc    6095
Gln Met Leu Glu Gly Ala Arg Gly Leu Val Asn Gln Leu Ile Gln Phe
        2020                2025                2030 ggt tcc tct ctc ctt ggt tac tct gag agg caa gat gct gag gcc atg    6143
Gly Ser Ser Leu Leu Gly Tyr Ser Glu Arg Gln Asp Ala Glu Ala Met
        2035                2040                2045 tcc caa ctc ttg caa acc cag gct tct gag ttg atc ctc acc tcc atc    6191
Ser Gln Leu Leu Gln Thr Gln Ala Ser Glu Leu Ile Leu Thr Ser Ile
        2050                2055                2060 agg atg caa gac aac cag ctt gct gag ttg gac tct gag aag act gct    6239
Arg Met Gln Asp Asn Gln Leu Ala Glu Leu Asp Ser Glu Lys Thr Ala
        2065                2070                2075 ctc caa gtc tcc ctt gct ggt gtc caa cag agg ttc gac agc tac tcc    6287
Leu Gln Val Ser Leu Ala Gly Val Gln Gln Arg Phe Asp Ser Tyr Ser
2080                2085                2090                2095 caa ctc tac gag gag aac atc aac gct ggt gag caa agg gct ttg gct    6335
Gln Leu Tyr Glu Glu Asn Ile Asn Ala Gly Glu Gln Arg Ala Leu Ala
        2100                2105                2110 ctc agg tct gag tct gcc att gag tcc caa ggt gct caa atc tcc cgc    6383
Leu Arg Ser Glu Ser Ala Ile Glu Ser Gln Gly Ala Gln Ile Ser Arg
        2115                2120                2125 atg gct ggt gct ggc gtg gac atg gct cca aac atc ttc ggt ctt gct    6431
Met Ala Gly Ala Gly Val Asp Met Ala Pro Asn Ile Phe Gly Leu Ala
        2130                2135                2140 gat ggt ggc atg cac tac ggt gcc att gct tac gcc att gct gat ggc    6479
Asp Gly Gly Met His Tyr Gly Ala Ile Ala Tyr Ala Ile Ala Asp Gly
        2145                2150                2155 att gag ctt tct gct tct gcc aag atg gtt gat gct gag aag gtg gct    6527
Ile Glu Leu Ser Ala Ser Ala Lys Met Val Asp Ala Glu Lys Val Ala
2160                2165                2170                2175 caa tct gaa atc tac cgt cgc aga cgc caa gaa tgg aag atc caa agg    6575
Gln Ser Glu Ile Tyr Arg Arg Arg Gln Glu Trp Lys Ile Gln Arg
        2180                2185                2190 gac aac gct caa gct gag atc aac cag ctc aac gct caa ctt gag tcc    6623
Asp Asn Ala Gln Ala Glu Ile Asn Gln Leu Asn Ala Gln Leu Glu Ser
```

```
                    2195                2200                2205
ctc agc atc agg cgt gag gct gct gag atg cag aag gag tac ctc aag      6671
Leu Ser Ile Arg Arg Glu Ala Ala Glu Met Gln Lys Glu Tyr Leu Lys
        2210                2215                2220 acc caa cag gct caa gct cag gct caa ctc acc ttc ctc agg tcc aag      6719
Thr Gln Gln Ala Gln Ala Gln Ala Gln Leu Thr Phe Leu Arg Ser Lys
        2225                2230                2235 ttc tcc aac cag gct ctc tac tcc tgg ctc aga ggc cgc ctc tct ggc      6767
Phe Ser Asn Gln Ala Leu Tyr Ser Trp Leu Arg Gly Arg Leu Ser Gly
2240                2245                2250                2255 atc tac ttc caa ttc tac gac ttg gct gtc tcc cgc tgc ctc atg gct      6815
Ile Tyr Phe Gln Phe Tyr Asp Leu Ala Val Ser Arg Cys Leu Met Ala
            2260                2265                2270 gag caa tcc tac caa tgg gag gcc aac gac aac agc atc tcc ttc gtc      6863
Glu Gln Ser Tyr Gln Trp Glu Ala Asn Asp Asn Ser Ile Ser Phe Val
            2275                2280                2285 aag cca ggt gct tgg caa ggc acc tac gct ggt ctc ctt tgc ggt gag      6911
Lys Pro Gly Ala Trp Gln Gly Thr Tyr Ala Gly Leu Leu Cys Gly Glu
            2290                2295                2300 gct ctc atc cag aac ttg gct caa atg gag gag gct tac ctc aag tgg      6959
Ala Leu Ile Gln Asn Leu Ala Gln Met Glu Glu Ala Tyr Leu Lys Trp
        2305                2310                2315 gag tcc aga gct ttg gag gta gag agg act gtc tcc ctt gct gta gtc      7007
Glu Ser Arg Ala Leu Glu Val Glu Arg Thr Val Ser Leu Ala Val Val
2320                2325                2330                2335 tac gac tcc ttg gag ggc aac gac agg ttc aac ctt gct gag caa atc      7055
Tyr Asp Ser Leu Glu Gly Asn Asp Arg Phe Asn Leu Ala Glu Gln Ile
            2340                2345                2350 cca gct ctc ttg gac aag ggt gag ggc act gct ggc acc aag gag aac      7103
Pro Ala Leu Leu Asp Lys Gly Glu Gly Thr Ala Gly Thr Lys Glu Asn
            2355                2360                2365 ggt ctc tcc ttg gcc aac gcc atc ctc tct gct tct gtc aag ctc tct      7151
Gly Leu Ser Leu Ala Asn Ala Ile Leu Ser Ala Ser Val Lys Leu Ser
            2370                2375                2380 gac ctc aag ttg ggt act gac tac cca gac tcc att gtg ggt tcc aac      7199
Asp Leu Lys Leu Gly Thr Asp Tyr Pro Asp Ser Ile Val Gly Ser Asn
        2385                2390                2395 aag gtc aga agg atc aag caa atc tct gtc tcc ctc cca gct ttg gtg      7247
Lys Val Arg Arg Ile Lys Gln Ile Ser Val Ser Leu Pro Ala Leu Val
2400                2405                2410                2415 ggt cca tac caa gat gtc caa gcc atg ctc tcc tac ggt ggc tcc acc      7295
Gly Pro Tyr Gln Asp Val Gln Ala Met Leu Ser Tyr Gly Gly Ser Thr
            2420                2425                2430 caa ctc cca aag ggt tgc tct gct ttg gct gtc tcc cac ggc acc aac      7343
Gln Leu Pro Lys Gly Cys Ser Ala Leu Ala Val Ser His Gly Thr Asn
            2435                2440                2445 gac tct ggt caa ttc caa ctt gac ttc aac gat ggc aag tac ctc cca      7391
Asp Ser Gly Gln Phe Gln Leu Asp Phe Asn Asp Gly Lys Tyr Leu Pro
        2450                2455                2460 ttc gaa ggc att gct ttg gat gac caa ggc acc ctc aac ctc caa ttc      7439
Phe Glu Gly Ile Ala Leu Asp Asp Gln Gly Thr Leu Asn Leu Gln Phe
        2465                2470                2475 cca aac gcc act gac aag cag aag gcc atc ctc caa acc atg tct gac      7487
Pro Asn Ala Thr Asp Lys Gln Lys Ala Ile Leu Gln Thr Met Ser Asp
2480                2485                2490                2495 atc atc ctc cac atc agg tac acc atc agg tgagctcgag aggcctgcgg        7537
Ile Ile Leu His Ile Arg Tyr Thr Ile Arg
            2500                2505
```

-continued

```
ccgc                                                                 7541

<210> SEQ ID NO 5
<211> LENGTH: 63
<212> TYPE: DNA
<213> ORGANISM: Artificial Sequence
<220> FEATURE:
<223> OTHER INFORMATION: Description of Artificial Sequence:hemicot
      sequence encoding ER signal from 15 kDa zein from Black
      Mexican Sweet maize
<220> FEATURE:
<221> NAME/KEY: CDS
<222> LOCATION: (1)..(63)

<400> SEQUENCE: 5 atg gct aag atg gtc att gtg ctt gtg gtc tgc ttg gct ctc tct gct       48
Met Ala Lys Met Val Ile Val Leu Val Val Cys Leu Ala Leu Ser Ala
  1               5                  10                  15 gcc tgt gct tca gcc                                                   63
Ala Cys Ala Ser Ala
             20

<210> SEQ ID NO 6
<211> LENGTH: 7621
<212> TYPE: DNA
<213> ORGANISM: Artificial Sequence
<220> FEATURE:
<223> OTHER INFORMATION: Description of Artificial Sequence:hemicot tcdA
      fused to the modified 15 kDa zein endoplasmic
      reticulum signal peptide
<220> FEATURE:
<221> NAME/KEY: CDS
<222> LOCATION: (4)..(7614)
<220> FEATURE: unsure
<221> NAME/KEY: (1)
<223> OTHER INFORMATION: n can be a, t, g, or c

<400> SEQUENCE: 6 ncc atg gct aag atg gtc att gtg ctt gtg gtc tgc ttg gct ctc tct       48
    Met Ala Lys Met Val Ile Val Leu Val Val Cys Leu Ala Leu Ser
      1               5                  10                  15 gct gcc tgt gct tca gcc atg aac gag tcc gtc aag gag atc cca gac       96
Ala Ala Cys Ala Ser Ala Met Asn Glu Ser Val Lys Glu Ile Pro Asp
                 20                  25                  30 gtc ctc aag tcc caa tgc ggt ttc aac tgc ctc act gac atc tcc cac      144
Val Leu Lys Ser Gln Cys Gly Phe Asn Cys Leu Thr Asp Ile Ser His
             35                  40                  45 agc tcc ttc aac gag ttc aga caa caa gtc tct gag cac ctc tcc tgg      192
Ser Ser Phe Asn Glu Phe Arg Gln Gln Val Ser Glu His Leu Ser Trp
         50                  55                  60 tcc gag acc cat gac ctc tac cat gac gct cag caa gct cag aag gac      240
Ser Glu Thr His Asp Leu Tyr His Asp Ala Gln Gln Ala Gln Lys Asp
     65                  70                  75 aac agg ctc tac gag gct agg atc ctc aag agg gct aac cca caa ctc      288
Asn Arg Leu Tyr Glu Ala Arg Ile Leu Lys Arg Ala Asn Pro Gln Leu
 80                  85                  90                  95 cag aac gct gtc cac ctc gcc atc ttg gct cca aac gct gag ttg att      336
Gln Asn Ala Val His Leu Ala Ile Leu Ala Pro Asn Ala Glu Leu Ile
                100                 105                 110 ggt tac aac aac cag ttc tct ggc aga gct agc cag tac gtg gct cct      384
Gly Tyr Asn Asn Gln Phe Ser Gly Arg Ala Ser Gln Tyr Val Ala Pro
            115                 120                 125 ggt aca gtc tcc tcc atg ttc agc cca gcc gct tac ctc act gag ttg      432
Gly Thr Val Ser Ser Met Phe Ser Pro Ala Ala Tyr Leu Thr Glu Leu
        130                 135                 140
```

```
tac cgc gag gct agg aac ctt cat gct tct gac tcc gtc tac tac ttg      480
Tyr Arg Glu Ala Arg Asn Leu His Ala Ser Asp Ser Val Tyr Tyr Leu
    145                 150                 155 gac aca cgc aga cca gac ctc aag agc atg gcc ctc agc caa cag aac      528
Asp Thr Arg Arg Pro Asp Leu Lys Ser Met Ala Leu Ser Gln Gln Asn
160                 165                 170                 175 atg gac att gag ttg tcc acc ctc tcc ttg agc aac gag ctt ctc ttg      576
Met Asp Ile Glu Leu Ser Thr Leu Ser Leu Ser Asn Glu Leu Leu Leu
                180                 185                 190 gag tcc atc aag act gag agc aag ttg gag aac tac acc aag gtc atg      624
Glu Ser Ile Lys Thr Glu Ser Lys Leu Glu Asn Tyr Thr Lys Val Met
            195                 200                 205 gag atg ctc tcc acc ttc aga cca agc ggt gca act cca tac cat gat      672
Glu Met Leu Ser Thr Phe Arg Pro Ser Gly Ala Thr Pro Tyr His Asp
        210                 215                 220 gcc tac gag aac gtc agg gag gtc atc caa ctt caa gac cct ggt ctt      720
Ala Tyr Glu Asn Val Arg Glu Val Ile Gln Leu Gln Asp Pro Gly Leu
    225                 230                 235 gag caa ctc aac gct tct cca gcc att gct ggt ttg atg cac cag gca      768
Glu Gln Leu Asn Ala Ser Pro Ala Ile Ala Gly Leu Met His Gln Ala
240                 245                 250                 255 tcc ttg ctc ggt atc aac gcc tcc atc tct cct gag ttg ttc aac atc      816
Ser Leu Leu Gly Ile Asn Ala Ser Ile Ser Pro Glu Leu Phe Asn Ile
                260                 265                 270 ttg act gag gag atc act gag ggc aac gct gag gag ttg tac aag aag      864
Leu Thr Glu Glu Ile Thr Glu Gly Asn Ala Glu Glu Leu Tyr Lys Lys
            275                 280                 285 aac ttc ggc aac att gag cca gcc tct ctt gca atg cct gag tac ctc      912
Asn Phe Gly Asn Ile Glu Pro Ala Ser Leu Ala Met Pro Glu Tyr Leu
        290                 295                 300 aag agg tac tac aac ttg tct gat gag gag ctt tct caa ttc att ggc      960
Lys Arg Tyr Tyr Asn Leu Ser Asp Glu Glu Leu Ser Gln Phe Ile Gly
    305                 310                 315 aag gct tcc aac ttc ggt caa cag gag tac agc aac aac cag ctc atc     1008
Lys Ala Ser Asn Phe Gly Gln Gln Glu Tyr Ser Asn Asn Gln Leu Ile
320                 325                 330                 335 act cca gtt gtg aac tcc tct gat ggc act gtg aag gtc tac cgc atc     1056
Thr Pro Val Val Asn Ser Ser Asp Gly Thr Val Lys Val Tyr Arg Ile
                340                 345                 350 aca cgt gag tac acc aca aac gcc tac caa atg gat gtt gag ttg ttc     1104
Thr Arg Glu Tyr Thr Thr Asn Ala Tyr Gln Met Asp Val Glu Leu Phe
            355                 360                 365 cca ttc ggt ggt gag aac tac aga ctt gac tac aag ttc aag aac ttc     1152
Pro Phe Gly Gly Glu Asn Tyr Arg Leu Asp Tyr Lys Phe Lys Asn Phe
        370                 375                 380 tac aac gcc tcc tac ctc tcc atc aag ttg aac gac aag agg gag ctt     1200
Tyr Asn Ala Ser Tyr Leu Ser Ile Lys Leu Asn Asp Lys Arg Glu Leu
    385                 390                 395 gtc agg act gag ggt gct cct caa gtg aac att gag tac tct gcc aac     1248
Val Arg Thr Glu Gly Ala Pro Gln Val Asn Ile Glu Tyr Ser Ala Asn
400                 405                 410                 415 atc acc ctc aac aca gct gac atc tct caa cca ttc gag att ggt ttg     1296
Ile Thr Leu Asn Thr Ala Asp Ile Ser Gln Pro Phe Glu Ile Gly Leu
                420                 425                 430 acc aga gtc ctt ccc tct ggc tcc tgg gcc tac gct gca gcc aag ttc     1344
Thr Arg Val Leu Pro Ser Gly Ser Trp Ala Tyr Ala Ala Ala Lys Phe
            435                 440                 445 act gtt gag gag tac aac cag tac tct ttc ctc ttg aag ctc aac aag     1392
Thr Val Glu Glu Tyr Asn Gln Tyr Ser Phe Leu Leu Lys Leu Asn Lys
        450                 455                 460
```

```
gca att cgt ctc agc aga gcc act gag ttg tct ccc acc atc ttg gag      1440
Ala Ile Arg Leu Ser Arg Ala Thr Glu Leu Ser Pro Thr Ile Leu Glu
    465                 470                 475 ggc att gtg agg tct gtc aac ctt caa ctt gac atc aac act gat gtg      1488
Gly Ile Val Arg Ser Val Asn Leu Gln Leu Asp Ile Asn Thr Asp Val
480                 485                 490                 495 ctt ggc aag gtc ttc ctc acc aag tac tac atg caa cgc tac gcc atc      1536
Leu Gly Lys Val Phe Leu Thr Lys Tyr Tyr Met Gln Arg Tyr Ala Ile
                500                 505                 510 cat gct gag act gca ctc atc ctc tgc aac gca ccc atc tct caa cgc      1584
His Ala Glu Thr Ala Leu Ile Leu Cys Asn Ala Pro Ile Ser Gln Arg
            515                 520                 525 tcc tac gac aac cag cct tcc cag ttc gac agg ctc ttc aac act cct      1632
Ser Tyr Asp Asn Gln Pro Ser Gln Phe Asp Arg Leu Phe Asn Thr Pro
        530                 535                 540 ctc ttg aac ggc cag tac ttc tcc act ggt gat gag gag att gac ctc      1680
Leu Leu Asn Gly Gln Tyr Phe Ser Thr Gly Asp Glu Glu Ile Asp Leu
    545                 550                 555 aac tct ggc tcc aca ggt gac tgg aga aag acc atc ttg aag agg gcc      1728
Asn Ser Gly Ser Thr Gly Asp Trp Arg Lys Thr Ile Leu Lys Arg Ala
560                 565                 570                 575 ttc aac att gat gat gtc tct ctc ttc cgt ctc ttg aag atc aca gat      1776
Phe Asn Ile Asp Asp Val Ser Leu Phe Arg Leu Leu Lys Ile Thr Asp
                580                 585                 590 cac gac aac aag gat ggc aag atc aag aac aac ttg aag aac ctt tcc      1824
His Asp Asn Lys Asp Gly Lys Ile Lys Asn Asn Leu Lys Asn Leu Ser
            595                 600                 605 aac ctc tac att ggc aag ttg ctt gca gac atc cac caa ctc acc att      1872
Asn Leu Tyr Ile Gly Lys Leu Leu Ala Asp Ile His Gln Leu Thr Ile
        610                 615                 620 gat gag ttg gac ctc ttg ctc att gca gtc ggt gag ggc aag acc aac      1920
Asp Glu Leu Asp Leu Leu Leu Ile Ala Val Gly Glu Gly Lys Thr Asn
    625                 630                 635 ctc tct gca atc tct gac aag cag ttg gca acc ctc atc agg aag ttg      1968
Leu Ser Ala Ile Ser Asp Lys Gln Leu Ala Thr Leu Ile Arg Lys Leu
640                 645                 650                 655 aac acc atc acc tcc tgg ctt cac acc cag aag tgg tct gtc ttc caa      2016
Asn Thr Ile Thr Ser Trp Leu His Thr Gln Lys Trp Ser Val Phe Gln
                660                 665                 670 ctc ttc atc atg acc agc acc tcc tac aac aag acc ctc act cct gag      2064
Leu Phe Ile Met Thr Ser Thr Ser Tyr Asn Lys Thr Leu Thr Pro Glu
            675                 680                 685 atc aag aac ctc ttg gac aca gtc tac cac ggt ctc caa ggc ttc gac      2112
Ile Lys Asn Leu Leu Asp Thr Val Tyr His Gly Leu Gln Gly Phe Asp
        690                 695                 700 aag gac aag gct gac ttg ctt cat gtc atg gct ccc tac att gca gcc      2160
Lys Asp Lys Ala Asp Leu Leu His Val Met Ala Pro Tyr Ile Ala Ala
    705                 710                 715 acc ctc caa ctc tcc tct gag aac gtg gct cac tct gtc ttg ctc tgg      2208
Thr Leu Gln Leu Ser Ser Glu Asn Val Ala His Ser Val Leu Leu Trp
720                 725                 730                 735 gct gac aag ctc caa cct ggt gat ggt gcc atg act gct gag aag ttc      2256
Ala Asp Lys Leu Gln Pro Gly Asp Gly Ala Met Thr Ala Glu Lys Phe
                740                 745                 750 tgg gac tgg ctc aac acc aag tac aca cca ggc tcc tct gag gct gtt      2304
Trp Asp Trp Leu Asn Thr Lys Tyr Thr Pro Gly Ser Ser Glu Ala Val
            755                 760                 765 gag act caa gag cac att gtg caa tac tgc cag gct ctt gca cag ttg      2352
Glu Thr Gln Glu His Ile Val Gln Tyr Cys Gln Ala Leu Ala Gln Leu
```

-continued

```
              770                 775                 780
gag atg gtc tac cac tcc act ggc atc aac gag aac gct ttc aga ctc    2400
Glu Met Val Tyr His Ser Thr Gly Ile Asn Glu Asn Ala Phe Arg Leu
    785                 790                 795 ttc gtc acc aag cct gag atg ttc ggt gct gcc aca ggt gct gca cct    2448
Phe Val Thr Lys Pro Glu Met Phe Gly Ala Ala Thr Gly Ala Ala Pro
800                 805                 810                 815 gct cat gat gct ctc tcc ctc atc atg ttg acc agg ttc gct gac tgg    2496
Ala His Asp Ala Leu Ser Leu Ile Met Leu Thr Arg Phe Ala Asp Trp
                820                 825                 830 gtc aac gct ctt ggt gag aag gct tcc tct gtc ttg gct gcc ttc gag    2544
Val Asn Ala Leu Gly Glu Lys Ala Ser Ser Val Leu Ala Ala Phe Glu
            835                 840                 845 gcc aac tcc ctc act gct gag caa ctt gct gat gcc atg aac ctt gat    2592
Ala Asn Ser Leu Thr Ala Glu Gln Leu Ala Asp Ala Met Asn Leu Asp
        850                 855                 860 gcc aac ctc ttg ctc caa gct tcc att caa gct cag aac cac caa cac    2640
Ala Asn Leu Leu Leu Gln Ala Ser Ile Gln Ala Gln Asn His Gln His
    865                 870                 875 ctc cca cct gtc act cca gag aac gct ttc tcc tgc tgg acc tcc atc    2688
Leu Pro Pro Val Thr Pro Glu Asn Ala Phe Ser Cys Trp Thr Ser Ile
880                 885                 890                 895 aac acc atc ctc caa tgg gtc aac gtg gct cag caa ctc aac gtg gct    2736
Asn Thr Ile Leu Gln Trp Val Asn Val Ala Gln Gln Leu Asn Val Ala
                900                 905                 910 cca caa ggt gtc tct gct ttg gtc ggt ctt gac tac atc cag tcc atg    2784
Pro Gln Gly Val Ser Ala Leu Val Gly Leu Asp Tyr Ile Gln Ser Met
            915                 920                 925 aag gag aca cca acc tac gct caa tgg gag aac gca gct ggt gtc ttg    2832
Lys Glu Thr Pro Thr Tyr Ala Gln Trp Glu Asn Ala Ala Gly Val Leu
        930                 935                 940 act gct ggt ctc aac tcc caa cag gcc aac acc ctc cat gct ttc ttg    2880
Thr Ala Gly Leu Asn Ser Gln Gln Ala Asn Thr Leu His Ala Phe Leu
    945                 950                 955 gat gag tct cgc tct gct gcc ctc tcc acc tac tac atc agg caa gtc    2928
Asp Glu Ser Arg Ser Ala Ala Leu Ser Thr Tyr Tyr Ile Arg Gln Val
960                 965                 970                 975 gcc aag gca gct gct gcc atc aag tct cgc gat gac ctc tac caa tac    2976
Ala Lys Ala Ala Ala Ala Ile Lys Ser Arg Asp Asp Leu Tyr Gln Tyr
                980                 985                 990 ctc ctc att gac aac cag gtc tct gct gcc atc aag acc acc agg atc    3024
Leu Leu Ile Asp Asn Gln Val Ser Ala Ala Ile Lys Thr Thr Arg Ile
            995                 1000                1005 gct gag gcc atc gct tcc atc caa ctc tac gtc aac cgc gct ctt gag    3072
Ala Glu Ala Ile Ala Ser Ile Gln Leu Tyr Val Asn Arg Ala Leu Glu
        1010                1015                1020 aac gtt gag gag aac gcc aac tct ggt gtc atc tct cgc caa ttc ttc    3120
Asn Val Glu Glu Asn Ala Asn Ser Gly Val Ile Ser Arg Gln Phe Phe
    1025                1030                1035 atc gac tgg gac aag tac aac aag agg tac tcc acc tgg gct ggt gtc    3168
Ile Asp Trp Asp Lys Tyr Asn Lys Arg Tyr Ser Thr Trp Ala Gly Val
1040                1045                1050                1055 tct caa ctt gtc tac tac cca gag aac tac att gac cca acc atg agg    3216
Ser Gln Leu Val Tyr Tyr Pro Glu Asn Tyr Ile Asp Pro Thr Met Arg
                1060                1065                1070 att ggt cag acc aag atg atg gat gct ctc ttg caa tct gtc tcc caa    3264
Ile Gly Gln Thr Lys Met Met Asp Ala Leu Leu Gln Ser Val Ser Gln
            1075                1080                1085 agc caa ctc aac gct gac act gtg gag gat gcc ttc atg agc tac ctc    3312
```

```
                                                                       -continued Ser Gln Leu Asn Ala Asp Thr Val Glu Asp Ala Phe Met Ser Tyr Leu
        1090                1095                1100 acc tcc ttc gag caa gtt gcc aac ctc aag gtc atc tct gct tac cat         3360
Thr Ser Phe Glu Gln Val Ala Asn Leu Lys Val Ile Ser Ala Tyr His
    1105                1110                1115 gac aac atc aac aac gac caa ggt ctc acc tac ttc att ggt ctc tct         3408
Asp Asn Ile Asn Asn Asp Gln Gly Leu Thr Tyr Phe Ile Gly Leu Ser
1120                1125                1130                1135 gag act gat gct ggt gag tac tac tgg aga tcc gtg gac cac agc aag         3456
Glu Thr Asp Ala Gly Glu Tyr Tyr Trp Arg Ser Val Asp His Ser Lys
                1140                1145                1150 ttc aac gat ggc aag ttc gct gca aac gct tgg tct gag tgg cac aag         3504
Phe Asn Asp Gly Lys Phe Ala Ala Asn Ala Trp Ser Glu Trp His Lys
            1155                1160                1165 att gac tgc cct atc aac cca tac aag tcc acc atc aga cct gtc atc         3552
Ile Asp Cys Pro Ile Asn Pro Tyr Lys Ser Thr Ile Arg Pro Val Ile
        1170                1175                1180 tac aag agc cgc ctc tac ttg ctc tgg ctt gag cag aag gag atc acc         3600
Tyr Lys Ser Arg Leu Tyr Leu Leu Trp Leu Glu Gln Lys Glu Ile Thr
    1185                1190                1195 aag caa act ggc aac tcc aag gat ggt tac caa act gag act gac tac         3648
Lys Gln Thr Gly Asn Ser Lys Asp Gly Tyr Gln Thr Glu Thr Asp Tyr
1200                1205                1210                1215 cgc tac gag ttg aag ttg gct cac atc cgc tac gat ggt acc tgg aac         3696
Arg Tyr Glu Leu Lys Leu Ala His Ile Arg Tyr Asp Gly Thr Trp Asn
                1220                1225                1230 act cca atc acc ttc gat gtc aac aag aag atc agc gag ttg aag ttg         3744
Thr Pro Ile Thr Phe Asp Val Asn Lys Lys Ile Ser Glu Leu Lys Leu
            1235                1240                1245 gag aag aac cgt gct cct ggt ctc tac tgc gct ggt tac caa ggt gag         3792
Glu Lys Asn Arg Ala Pro Gly Leu Tyr Cys Ala Gly Tyr Gln Gly Glu
        1250                1255                1260 gac acc ctc ttg gtc atg ttc tac aac cag caa gac acc ctt gac tcc         3840
Asp Thr Leu Leu Val Met Phe Tyr Asn Gln Gln Asp Thr Leu Asp Ser
    1265                1270                1275 tac aag aac gct tcc atg caa ggt ctc tac atc ttc gct gac atg gct         3888
Tyr Lys Asn Ala Ser Met Gln Gly Leu Tyr Ile Phe Ala Asp Met Ala
1280                1285                1290                1295 tcc aag gac atg act cca gag caa agc aac gtc tac cgt gac aac tcc         3936
Ser Lys Asp Met Thr Pro Glu Gln Ser Asn Val Tyr Arg Asp Asn Ser
                1300                1305                1310 tac caa cag ttc gac acc aac aac gtc agg cgt gtc aac aac aga tac         3984
Tyr Gln Gln Phe Asp Thr Asn Asn Val Arg Arg Val Asn Asn Arg Tyr
            1315                1320                1325 gct gag gac tac gag atc cca agc tct gtc agc tct cgc aag gac tac         4032
Ala Glu Asp Tyr Glu Ile Pro Ser Ser Val Ser Ser Arg Lys Asp Tyr
        1330                1335                1340 ggc tgg ggt gac tac tac ctc agc atg gtg tac aac ggt gac atc cca         4080
Gly Trp Gly Asp Tyr Tyr Leu Ser Met Val Tyr Asn Gly Asp Ile Pro
    1345                1350                1355 acc atc aac tac aag gct gcc tct tcc gac ctc aaa atc tac atc agc         4128
Thr Ile Asn Tyr Lys Ala Ala Ser Ser Asp Leu Lys Ile Tyr Ile Ser
1360                1365                1370                1375 cca aag ctc agg atc atc cac aac ggc tac gag ggt cag aag agg aac         4176
Pro Lys Leu Arg Ile Ile His Asn Gly Tyr Glu Gly Gln Lys Arg Asn
                1380                1385                1390 cag tgc aac ttg atg aac aag tac ggc aag ttg ggt gac aag ttc att         4224
Gln Cys Asn Leu Met Asn Lys Tyr Gly Lys Leu Gly Asp Lys Phe Ile
            1395                1400                1405
```

-continued

| | |
|---|---|
| gtc tac acc tct ctt ggt gtc aac cca aac aac agc tcc aac aag ctc<br>Val Tyr Thr Ser Leu Gly Val Asn Pro Asn Asn Ser Ser Asn Lys Leu<br>          1410                     1415                  1420 | 4272 |
| atg ttc tac cca gtc tac caa tac tct ggc aac acc tct ggt ctc aac<br>Met Phe Tyr Pro Val Tyr Gln Tyr Ser Gly Asn Thr Ser Gly Leu Asn<br>1425                  1430                  1435 | 4320 |
| cag ggt aga ctc ttg ttc cac agg gac acc acc tac cca agc aag gtg<br>Gln Gly Arg Leu Leu Phe His Arg Asp Thr Thr Tyr Pro Ser Lys Val<br>1440                  1445                  1450                  1455 | 4368 |
| gag gct tgg att cct ggt gcc aag agg tcc ctc acc aac cag aac gct<br>Glu Ala Trp Ile Pro Gly Ala Lys Arg Ser Leu Thr Asn Gln Asn Ala<br>                1460                  1465                  1470 | 4416 |
| gcc att ggt gat gac tac gcc aca gac tcc ctc aac aag cct gat gac<br>Ala Ile Gly Asp Asp Tyr Ala Thr Asp Ser Leu Asn Lys Pro Asp Asp<br>1475                  1480                  1485 | 4464 |
| ctc aag cag tac atc ttc atg act gac tcc aag ggc aca gcc act gat<br>Leu Lys Gln Tyr Ile Phe Met Thr Asp Ser Lys Gly Thr Ala Thr Asp<br>          1490                  1495                  1500 | 4512 |
| gtc tct ggt cca gtg gag atc aac act gca atc agc cca gcc aag gtc<br>Val Ser Gly Pro Val Glu Ile Asn Thr Ala Ile Ser Pro Ala Lys Val<br>1505                  1510                  1515 | 4560 |
| caa atc att gtc aag gct ggt ggc aag gag caa acc ttc aca gct gac<br>Gln Ile Ile Val Lys Ala Gly Gly Lys Glu Gln Thr Phe Thr Ala Asp<br>1520                  1525                  1530                  1535 | 4608 |
| aag gat gtc tcc atc cag cca agc cca tcc ttc gat gag atg aac tac<br>Lys Asp Val Ser Ile Gln Pro Ser Pro Ser Phe Asp Glu Met Asn Tyr<br>                1540                  1545                  1550 | 4656 |
| caa ttc aac gct ctt gag att gat ggt tct ggc ctc aac ttc atc aac<br>Gln Phe Asn Ala Leu Glu Ile Asp Gly Ser Gly Leu Asn Phe Ile Asn<br>          1555                  1560                  1565 | 4704 |
| aac tct gct tcc att gat gtc acc ttc act gcc ttc gct gag gat ggc<br>Asn Ser Ala Ser Ile Asp Val Thr Phe Thr Ala Phe Ala Glu Asp Gly<br>1570                  1575                  1580 | 4752 |
| cgc aag ttg ggt tac gag agc ttc tcc atc cca gtc acc ctt aag gtt<br>Arg Lys Leu Gly Tyr Glu Ser Phe Ser Ile Pro Val Thr Leu Lys Val<br>          1585                  1590                  1595 | 4800 |
| tcc act gac aac gca ctc acc ctt cat cac aac gag aac ggt gct cag<br>Ser Thr Asp Asn Ala Leu Thr Leu His His Asn Glu Asn Gly Ala Gln<br>1600                  1605                  1610                  1615 | 4848 |
| tac atg caa tgg caa agc tac cgc acc agg ttg aac acc ctc ttc gca<br>Tyr Met Gln Trp Gln Ser Tyr Arg Thr Arg Leu Asn Thr Leu Phe Ala<br>                1620                  1625                  1630 | 4896 |
| agg caa ctt gtg gcc cgt gcc acc aca ggc att gac acc atc ctc agc<br>Arg Gln Leu Val Ala Arg Ala Thr Thr Gly Ile Asp Thr Ile Leu Ser<br>          1635                  1640                  1645 | 4944 |
| atg gag acc cag aac atc caa gag cca cag ttg ggc aag ggt ttc tac<br>Met Glu Thr Gln Asn Ile Gln Glu Pro Gln Leu Gly Lys Gly Phe Tyr<br>1650                  1655                  1660 | 4992 |
| gcc acc ttc gtc atc cca cct tac aac ctc agc act cat ggt gat gag<br>Ala Thr Phe Val Ile Pro Pro Tyr Asn Leu Ser Thr His Gly Asp Glu<br>1665                  1670                  1675 | 5040 |
| agg tgg ttc aag ctc tac atc aag cac gtg gtt gac aac aac tcc cac<br>Arg Trp Phe Lys Leu Tyr Ile Lys His Val Val Asp Asn Asn Ser His<br>1680                  1685                  1690                  1695 | 5088 |
| atc atc tac tct ggt caa ctc act gac acc aac atc aac atc acc ctc<br>Ile Ile Tyr Ser Gly Gln Leu Thr Asp Thr Asn Ile Asn Ile Thr Leu<br>                1700                  1705                  1710 | 5136 |
| ttc atc cca ctt gac gat gtc cca ctc aac cag gac tac cat gcc aag<br>Phe Ile Pro Leu Asp Asp Val Pro Leu Asn Gln Asp Tyr His Ala Lys<br>1715                  1720                  1725 | 5184 |

```
gtc tac atg acc ttc aag aag tct cca tct gat ggc acc tgg tgg ggt      5232
Val Tyr Met Thr Phe Lys Lys Ser Pro Ser Asp Gly Thr Trp Trp Gly
        1730                1735                1740 cca cac ttc gtc cgt gat gac aag ggc atc gtc acc atc aac cca aag      5280
Pro His Phe Val Arg Asp Asp Lys Gly Ile Val Thr Ile Asn Pro Lys
1745                1750                1755 tcc atc ctc acc cac ttc gag tct gtc aac gtt ctc aac aac atc tcc      5328
Ser Ile Leu Thr His Phe Glu Ser Val Asn Val Leu Asn Asn Ile Ser
1760                1765                1770                1775 tct gag cca atg gac ttc tct ggt gcc aac tcc ctc tac ttc tgg gag      5376
Ser Glu Pro Met Asp Phe Ser Gly Ala Asn Ser Leu Tyr Phe Trp Glu
                1780                1785                1790 ttg ttc tac tac aca cca atg ctt gtg gct caa agg ttg ctc cat gag      5424
Leu Phe Tyr Tyr Thr Pro Met Leu Val Ala Gln Arg Leu Leu His Glu
        1795                1800                1805 cag aac ttc gat gag gcc aac agg tgg ctc aag tac gtc tgg agc cca      5472
Gln Asn Phe Asp Glu Ala Asn Arg Trp Leu Lys Tyr Val Trp Ser Pro
                1810                1815                1820 tct ggt tac att gtg cat ggt caa atc cag aac tac caa tgg aac gtc      5520
Ser Gly Tyr Ile Val His Gly Gln Ile Gln Asn Tyr Gln Trp Asn Val
        1825                1830                1835 agg cca ttg ctt gag gac acc tcc tgg aac tct gac cca ctt gac tct      5568
Arg Pro Leu Leu Glu Asp Thr Ser Trp Asn Ser Asp Pro Leu Asp Ser
1840                1845                1850                1855 gtg gac cct gat gct gtg gct caa cat gac cca atg cac tac aag gtc      5616
Val Asp Pro Asp Ala Val Ala Gln His Asp Pro Met His Tyr Lys Val
                1860                1865                1870 tcc acc ttc atg agg acc ttg gac ctc ttg att gcc aga ggt gac cat      5664
Ser Thr Phe Met Arg Thr Leu Asp Leu Leu Ile Ala Arg Gly Asp His
        1875                1880                1885 gct tac cgc caa ttg gag agg gac acc ctc aac gag gca aag atg tgg      5712
Ala Tyr Arg Gln Leu Glu Arg Asp Thr Leu Asn Glu Ala Lys Met Trp
                1890                1895                1900 tac atg caa gct ctc cac ctc ttg ggt gac aag cca tac ctc cca ctc      5760
Tyr Met Gln Ala Leu His Leu Leu Gly Asp Lys Pro Tyr Leu Pro Leu
        1905                1910                1915 agc acc act tgg tcc gac cca agg ttg gac cgt gct gct gac atc acc      5808
Ser Thr Thr Trp Ser Asp Pro Arg Leu Asp Arg Ala Ala Asp Ile Thr
1920                1925                1930                1935 act cag aac gct cat gac tct gcc att gtt gct ctc agg cag aac atc      5856
Thr Gln Asn Ala His Asp Ser Ala Ile Val Ala Leu Arg Gln Asn Ile
                1940                1945                1950 cca act cct gct cca ctc tcc ctc aga tct gct aac acc ctc act gac      5904
Pro Thr Pro Ala Pro Leu Ser Leu Arg Ser Ala Asn Thr Leu Thr Asp
        1955                1960                1965 ttg ttc ctc cca cag atc aac gag gtc atg atg aac tac tgg caa acc      5952
Leu Phe Leu Pro Gln Ile Asn Glu Val Met Met Asn Tyr Trp Gln Thr
                1970                1975                1980 ttg gct caa agg gtc tac aac ctc aga cac aac ctc tcc att gat ggt      6000
Leu Ala Gln Arg Val Tyr Asn Leu Arg His Asn Leu Ser Ile Asp Gly
        1985                1990                1995 caa cca ctc tac ctc cca atc tac gcc aca cca gct gac cca aag gct      6048
Gln Pro Leu Tyr Leu Pro Ile Tyr Ala Thr Pro Ala Asp Pro Lys Ala
2000                2005                2010                2015 ctt ctc tct gct gct gtg gct acc agc caa ggt ggt ggc aag ctc cca      6096
Leu Leu Ser Ala Ala Val Ala Thr Ser Gln Gly Gly Gly Lys Leu Pro
                2020                2025                2030 gag tcc ttc atg tcc ctc tgg agg ttc cca cac atg ttg gag aac gcc      6144
Glu Ser Phe Met Ser Leu Trp Arg Phe Pro His Met Leu Glu Asn Ala
```

-continued

```
                    2035                  2040                   2045
cgt ggc atg gtc tcc caa ctc acc cag ttc ggt tcc acc ctc cag aac        6192
Arg Gly Met Val Ser Gln Leu Thr Gln Phe Gly Ser Thr Leu Gln Asn
        2050                  2055                   2060 atc att gag agg caa gat gct gag gct ctc aac gct ttg ctc cag aac        6240
Ile Ile Glu Arg Gln Asp Ala Glu Ala Leu Asn Ala Leu Leu Gln Asn
    2065                  2070                   2075 cag gca gct gag ttg atc ctc acc aac ttg tcc atc caa gac aag acc        6288
Gln Ala Ala Glu Leu Ile Leu Thr Asn Leu Ser Ile Gln Asp Lys Thr
2080                  2085                   2090                   2095 att gag gag ctt gat gct gag aag aca gtc ctt gag aag agc aag gct        6336
Ile Glu Glu Leu Asp Ala Glu Lys Thr Val Leu Glu Lys Ser Lys Ala
        2100                  2105                   2110 ggt gcc caa tct cgc ttc gac tcc tac ggc aag ctc tac gat gag aac        6384
Gly Ala Gln Ser Arg Phe Asp Ser Tyr Gly Lys Leu Tyr Asp Glu Asn
        2115                  2120                   2125 atc aac gct ggt gag aac cag gcc atg acc ctc agg gct tcc gca gct        6432
Ile Asn Ala Gly Glu Asn Gln Ala Met Thr Leu Arg Ala Ser Ala Ala
        2130                  2135                   2140 ggt ctc acc act gct gtc caa gcc tct cgc ttg gct ggt gca gct gct        6480
Gly Leu Thr Thr Ala Val Gln Ala Ser Arg Leu Ala Gly Ala Ala Ala
        2145                  2150                   2155 gac ctc gtt cca aac atc ttc ggt ttc gct ggt ggt ggc tcc aga tgg        6528
Asp Leu Val Pro Asn Ile Phe Gly Phe Ala Gly Gly Gly Ser Arg Trp
2160                  2165                   2170                   2175 ggt gcc att gct gag gct acc ggt tac gtc atg gag ttc tct gcc aac        6576
Gly Ala Ile Ala Glu Ala Thr Gly Tyr Val Met Glu Phe Ser Ala Asn
        2180                  2185                   2190 gtc atg aac act gag gct gac aag atc agc caa tct gag acc tac aga        6624
Val Met Asn Thr Glu Ala Asp Lys Ile Ser Gln Ser Glu Thr Tyr Arg
        2195                  2200                   2205 agg cgc cgt caa gag tgg gag atc caa agg aac aac gct gag gca gag        6672
Arg Arg Arg Gln Glu Trp Glu Ile Gln Arg Asn Asn Ala Glu Ala Glu
        2210                  2215                   2220 ttg aag caa atc gat gct caa ctc aag tcc ttg gct gtc aga agg gag        6720
Leu Lys Gln Ile Asp Ala Gln Leu Lys Ser Leu Ala Val Arg Arg Glu
        2225                  2230                   2235 gct gct gtc ctc cag aag acc tcc ctc aag acc caa cag gag caa acc        6768
Ala Ala Val Leu Gln Lys Thr Ser Leu Lys Thr Gln Gln Glu Gln Thr
2240                  2245                   2250                   2255 cag tcc cag ttg gct ttc ctc caa agg aag ttc tcc aac cag gct ctc        6816
Gln Ser Gln Leu Ala Phe Leu Gln Arg Lys Phe Ser Asn Gln Ala Leu
        2260                  2265                   2270 tac aac tgg ctc aga ggc cgc ttg gct gcc atc tac ttc caa ttc tac        6864
Tyr Asn Trp Leu Arg Gly Arg Leu Ala Ala Ile Tyr Phe Gln Phe Tyr
        2275                  2280                   2285 gac ctt gct gtg gcc agg tgc ctc atg gct gag caa gcc tac cgc tgg        6912
Asp Leu Ala Val Ala Arg Cys Leu Met Ala Glu Gln Ala Tyr Arg Trp
        2290                  2295                   2300 gag ttg aac gat gac tcc gcc agg ttc atc aag cca ggt gct tgg caa        6960
Glu Leu Asn Asp Asp Ser Ala Arg Phe Ile Lys Pro Gly Ala Trp Gln
        2305                  2310                   2315 ggc acc tac gct ggt ctc ctt gct ggt gag acc ctc atg ctc tcc ttg        7008
Gly Thr Tyr Ala Gly Leu Leu Ala Gly Glu Thr Leu Met Leu Ser Leu
2320                  2325                   2330                   2335 gct caa atg gag gat gct cac ctc aag agg gac aag agg gct ttg gag        7056
Ala Gln Met Glu Asp Ala His Leu Lys Arg Asp Lys Arg Ala Leu Glu
        2340                  2345                   2350 gtg gag agg aca gtc tcc ctt gct gag gtc tac gct ggt ctc cca aag        7104
```

```
                                                                    -continued Val Glu Arg Thr Val Ser Leu Ala Glu Val Tyr Ala Gly Leu Pro Lys
            2355             2360             2365 gac aac ggt cca ttc tcc ctt gct caa gag att gac aag ttg gtc agc     7152
Asp Asn Gly Pro Phe Ser Leu Ala Gln Glu Ile Asp Lys Leu Val Ser
            2370             2375             2380 caa ggt tct ggt tct gct ggt tct ggt aac aac aac ttg gct ttc ggc     7200
Gln Gly Ser Gly Ser Ala Gly Ser Gly Asn Asn Asn Leu Ala Phe Gly
            2385             2390             2395 gct ggt act gac acc aag acc tcc ctc caa gcc tct gtc tcc ttc gct     7248
Ala Gly Thr Asp Thr Lys Thr Ser Leu Gln Ala Ser Val Ser Phe Ala
2400             2405             2410             2415 gac ctc aag atc agg gag gac tac cca gct tcc ctt ggc aag atc agg     7296
Asp Leu Lys Ile Arg Glu Asp Tyr Pro Ala Ser Leu Gly Lys Ile Arg
            2420             2425             2430 cgc atc aag caa atc tct gtc acc ctc cca gct ctc ttg ggt cca tac     7344
Arg Ile Lys Gln Ile Ser Val Thr Leu Pro Ala Leu Leu Gly Pro Tyr
            2435             2440             2445 caa gat gtc caa gca atc ctc tcc tac ggt gac aag gct ggt ttg gcg     7392
Gln Asp Val Gln Ala Ile Leu Ser Tyr Gly Asp Lys Ala Gly Leu Ala
            2450             2455             2460 aac ggt tgc gag gct ctt gct gtc tct cat ggc atg aac gac tct ggt     7440
Asn Gly Cys Glu Ala Leu Ala Val Ser His Gly Met Asn Asp Ser Gly
            2465             2470             2475 caa ttc caa ctt gac ttc aac gat ggc aag ttc ctc cca ttc gag ggc     7488
Gln Phe Gln Leu Asp Phe Asn Asp Gly Lys Phe Leu Pro Phe Glu Gly
2480             2485             2490             2495 att gcc att gac caa ggc acc ctc acc ctc tcc ttc cca aac gct tcc     7536
Ile Ala Ile Asp Gln Gly Thr Leu Thr Leu Ser Phe Pro Asn Ala Ser
            2500             2505             2510 atg cca gag aag gga aag caa gcc acc atg ctc aag acc ctc aac gat     7584
Met Pro Glu Lys Gly Lys Gln Ala Thr Met Leu Lys Thr Leu Asn Asp
            2515             2520             2525 atc atc ctc cac atc agg tac acc atc aag tgagctc                     7621
Ile Ile Leu His Ile Arg Tyr Thr Ile Lys
            2530             2535
```